United States Patent [19]

Harbert et al.

[11] 4,306,097

[45] Dec. 15, 1981

[54] 3-[2-HYDROXY-4-(SUBSTITUTED)PHENYL]-CYCLOALKANOL ANALGESIC AGENTS

[75] Inventors: Charles A. Harbert, Waterford; Michael R. Johnson; Lawrence S. Melvin, Jr., both of Gales Ferry, all of Conn.

[73] Assignee: Pfizer Inc., New York, N.Y.

[21] Appl. No.: 185,082

[22] Filed: Sep. 8, 1980

Related U.S. Application Data

[60] Division of Ser. No. 963,667, Nov. 24, 1978, abandoned, which is a continuation-in-part of Ser. No. 926,687, Jul. 25, 1978, abandoned, which is a continuation-in-part of Ser. No. 833,102, Sep. 13, 1977, abandoned.

[51] Int. Cl.$^3$ ............... C07C 39/15; C07C 39/21; C07C 43/115; C07C 43/168
[52] U.S. Cl. ............... 568/731; 560/194; 560/254; 568/743; 560/138; 568/644; 568/646; 568/329; 424/341; 424/346; 424/311; 424/313; 424/267; 424/274; 568/330; 568/442; 568/377; 568/655; 546/192; 546/238; 544/106; 544/172; 544/399; 260/326.8; 260/326.43; 260/348.17; 260/456 P; 568/662; 568/660; 568/649; 568/648; 568/780; 568/631; 568/308; 568/325; 260/934; 260/963

[58] Field of Search ............... 568/743, 731, 644, 646

[56] References Cited

U.S. PATENT DOCUMENTS

| | | | |
|---|---|---|---|
| 3,273,992 | 9/1966 | Treves et al. | 71/2.3 |
| 3,576,887 | 4/1971 | Hughes et al. | |
| 3,622,588 | 11/1971 | Griot | |
| 3,862,986 | 1/1975 | Hellerbach | 424/258 X |
| 3,974,157 | 8/1976 | Shetty et al. | 424/250 X |

OTHER PUBLICATIONS

Shunsaku et al., Chem. Abs., vol. 78 (1973) 135861m.
Yoichi et al., Chem. Abs., vol. 85 (1976) 176952f.

Primary Examiner—Bernard Helfin
Attorney, Agent, or Firm—Charles J. Knuth; Peter C. Richardson; Albert E. Frost

[57] ABSTRACT

Cycloalkanones, cycloalkanols and unsaturated analogs thereof, each of which has at the 3-position a 2-hydroxy-4-substituted phenyl group wherein the 4-position substituent is alkyl which can have an oxygen atom as part of the chain, or aralkyl which can have an oxygen atom as part of the alkyl chain, their use for pharmacological and medicinal purposes, intermediates therefor and processes for their preparation.

12 Claims, No Drawings

3-[2-HYDROXY-4-(SUBSTITUTED)PHENYL]-CYCLOALKANOL ANALGESIC AGENTS

CROSS REFERENCE TO RELATED APPLICATIONS

This application is a division of U.S. application Ser. No. 963,667, filed Nov. 24, 1978 and now abandoned, which in turn is a continuation-in-part of application Ser. No. 926,687 filed July 25, 1978 and now abandoned, which in turn is a continuation-in-part of application Ser. No. 833,102 filed Sept. 13, 1977 and now abandoned.

BACKGROUND OF THE INVENTION

1. Field of the Invention

This invention relates to certain cycloalkanones, cycloalkanols and unsaturated analogs thereof having from 5 to 8 carbon atoms in the cycloalkyl ring and at the 3-position a 2-hydroxy-4-(Z-W-substituted)phenyl group wherein Z is alkylene having from one to thirteen carbon atoms or $(alk_1)_m$—O—$(alk_2)_n$—wherein each of m and n is 0 or 1 and each of $(alk_1)$ and $(alk_2)$ is alkylene having from one to thirteen carbon atoms with the proviso that summation of carbon atoms in $(alk_1)$ plus $(alk_2)$ is not greater than thirteen; and W is hydrogen, phenyl, chlorophenyl, fluorophenyl or pyridyl; derivatives thereof, intermediates therefor and processes for their preparation. The products are useful as CNS agents, especially as analgesics, tranquilizers, sedatives and antianxiety agents in mammals, including man, and/or as anticonvulsants, diuretics and antidiarrheal agents in mammals, including man.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other analgesic agents such as d-propoxyphene, codeine, and morphine, possess addictive liability. The need for improved and potent analgesic agents is, therefore, evident.

U.S. Pat. No. 3,576,887, issued Apr. 27, 1971, describes a series of 1-(1'-hydroxy)alkyl-2-o-hydroxyphenylcyclohexane or -ene compounds which serve as intermediates for production of 6,6-dialkyltetrahydro- and hexahydro- dibenzo[b,d]pyrans of use as central nervous system depressants.

U.S. Pat. No. 3,974,157 describes 2-phenylcyclohexanones as intermediates for preparation of 1-(aminoalkyl)-2-phenylcyclohexanols useful as analgesics, local anesthetics and antiarrhythmics. The 2-phenylcyclohexanones can be substituted in the phenyl ring with up to two alkyl, hydroxy or alkoxy groups.

Chemical Abstracts 85, 176952f (1976) discloses a number of 3-phenyl- and 3-phenalkylcyclohexanones as intermediates for 2-aminomethyl-3-phenyl (or phenalkyl)-cyclohexanones which exhibit analgesic, sedative, antidepressant and anticonvulsant activities.

SUMMARY OF THE INVENTION

It has now been found that certain cycloalkanones, cycloalkanols, and unsaturated analogs thereof having at the 3-position a 2-hydroxy-4-(substituted)phenyl group (formula I below) are effective as CNS agents, especially as analgesics, tranquilizers, sedatives and antianxiety agents in mammals, including humans, and/or as anticonvulsants, diuretics and antidiarrheal agents in mammals, including man. Also included in this invention are various derivatives of said compounds which are useful as dosage forms of the compounds, intermediates for compounds having formula I, and methods for their preparation. The compounds have the formula:

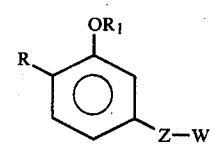

wherein R is selected from the group consisting of saturated and unsaturated cycloalkyl moieties selected from the group consisting of

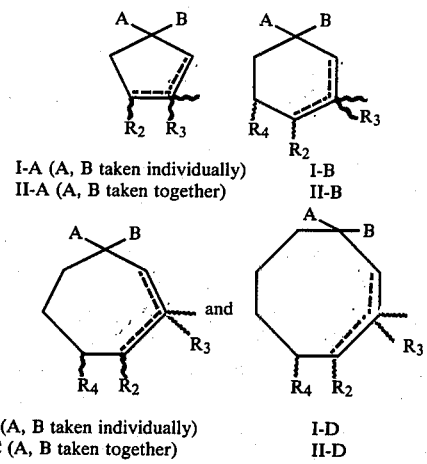

I-A (A, B taken individually)   I-B
II-A (A, B taken together)       II-B

I-C (A, B taken individually)   I-D
II-C (A, B taken together)       II-D wherein
the broken lines represent an optional double bond at one of said locations, in which case, $R_3$ cannot be present;

A when taken alone is hydrogen;

B when taken alone is selected from the group consisting of hydroxy, hydroxymethyl, and alkanoyloxy having from one to five carbon atoms (formula I series of compounds);

A and B when taken together (formula II series of compounds) are selected from the group consisting of oxo, methylene and alkylenedioxy having from two to four carbon atoms;

$R_1$ is selected from the group consisting of hydrogen, alkanoyl having from one to five carbon atoms, benzyl, —P(O)(OH)$_2$ and the mono- and di-sodium and potassium salts thereof, —CO(CH$_2$)$_2$COOH and the sodium and potassium salts thereof, and —CO—(CH$_2$)$_p$—NR$_5$R$_6$ wherein p is an integer from 1 to 4; each of $R_5$ and $R_6$ when taken individually is selected from the group consisting of hydrogen and alkyl having from one to four carbon atoms; $R_5$ and $R_6$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_2$ is selected from the group consisting of hydrogen, alkyl having from one to six carbon atoms, alkenyl having from three to six carbon atoms, phenyl and phenylalkyl having from one to four carbon atoms in the alkyl moiety;

$R_3$ is selected from the group consisting of hydrogen and methyl;

$R_4$ is selected from the group consisting of hydrogen and alkyl having from one to six carbon atoms; provided that when $R_3$ is methyl $R_4$ is hydrogen;

Z is selected from the group consisting of (a) alkylene having from one to thirteen carbon atoms; (b) —(alk$_1$-)$_m$—O—(alk$_2$)$_n$—wherein each of (alk$_1$) and (alk$_2$) is alkylene having from one to thirteen carbon atoms, with the proviso that the summation of carbon atoms in (alk$_1$) plus (alk$_2$) is not greater than thirteen; each of m and n is 0 or 1; and W is selected from the group consisting of hydrogen, pyridyl,

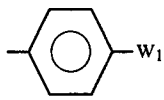

wherein $W_1$ is selected from the group consisting of hydrogen, fluoro and chloro.

The broken lines in formula I compounds, i.e. formulae IA–ID, represent the optional presence of a double bond at one of said locations.

Also included in this invention are the pharmaceutically acceptable acid addition salts of those compounds of formulae I which contain a basic group. Typical of such compounds are those wherein the W variable is pyridyl and/or $OR_1$ represents a basic ester moiety. In compounds having two basic groups present, polyacid addition salts are, of course, possible. Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate, 2-hydroxy-3-naphthoate, lactate, mandelate and methanesulfonate.

Compounds of formulae IA–ID wherein A and B when taken together are oxo and $R_1$ is hydrogen exist, in solution, in equilibrium with their hemiketal forms. The keto and hemiketal forms of said compounds of formula I are included in this invention.

Compounds of formula IA–ID wherein A is hydrogen and B is hydroxy contain asymmetric centers in the 1-, the 3- and the 4-positions and, where the cycloalkyl group is 6-8 membered, at the 5-position, in the cycloalkyl moiety and may, of course, contain additional asymmetric centers in the 4- nd 5-position substituents and in (—Z—W) of the phenyl ring. Cis-relationship between the substituent at the 1-position of the cycloalkyl moiety and the phenolic, or substituted phenolic, moiety at the 3- position is favored, and trans-relationship between the 3- and 4-substituents and the 4- and 5-substituents on the cycloalkyl moiety are favored because of the greater (quantitatively) biological activity. For the same reason, the trans-3,4-relationship is also favored in compounds of formula IA–ID wherein A and B when taken together represent oxo.

For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixture, the diastereomeric mixture as well as of the pure enantiomers and diastereomers is determined by the biological evaluation procedures described below.

In addition to the above formulae, various intermediates useful in the preparation of compounds of formula I are also included in this invention. The intermediates have formulae II–IV below:

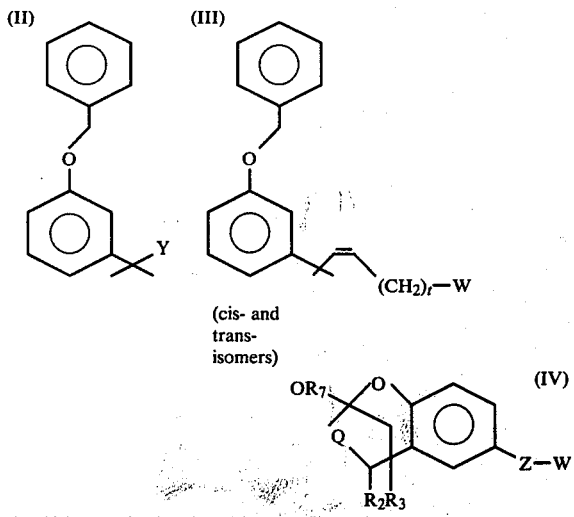

(in which stereochemistry is not represented)

wherein

Z, W, $R_2$ and $R_3$ are as defined above; Y is selected from the group consisting of cyano and formyl;

t is an integer from 1 to 8;

$R_7$ is selected from the group consisting of hydrogen and alkyl having from one to four carbon atoms; and Q is selected from the group consisting of —CH$_2$—, —CH$_2$—CH(R$_4$)—, —CH$_2$—CH$_2$—CH(R$_4$)— and —CH$_2$—CH$_2$—CH$_2$—CH—(R$_4$)—.

Compounds of formula IV represent the hemiketal and ketal forms of the saturated cycloalkyl compounds of formula I (A–D) wherein A and B taken together represent oxo.

Favored because of their greater biological activity relative to that of other compounds described herein are the saturated cycloalkyl and delta$^3$-unsaturated cycloalkyl compounds of formulae IA–ID wherein A and B together are oxo; A and B when taken individually are hydrogen and hydroxy, respectively; $R_2$ is hydrogen, alkenyl or alkyl; $R_1$ is hydrogen or alkanoyl; $R_3$ is hydrogen or methyl; $R_4$ is hydrogen or alkyl; and Z and W have the values shown below:

| Z | m | n | W |
|---|---|---|---|
| alkylene having from 7 to 11 carbon atoms | — | — | H |
| alkylene having from 4 to 7 carbon atoms | — | — | ─⟨O⟩─$W_1$, pyridyl |
| (alk$_1$)$_m$—O—(alk$_2$)$_n$ | 0,1 | 1 | ─⟨O⟩─$W_1$, pyridyl | each of (alk$_1$) and (alk$_2$) is alkylene having from one to seven carbon atoms with the proviso the summation of carbon atoms in (alk$_1$) plus (alk$_2$)

| -continued | | | |
|---|---|---|---|
| Z | m | n | W |
| is not less than four or greater than seven; | | | |
| $(alk_1)_m$—O—$(alk_2)_n$ | 0,1 | 1 | H |
| each of $(alk_1)$ and $(alk_2)$ is alkylene having from one to eleven carbon atoms with the proviso the summation of carbon atoms in $(alk_1)$ plus $(alk_2)$ is not less than seven or greater than eleven; | | | |

Preferred compounds of formula I, and especially of the saturated cycloalkyl compounds of formula I, are those favored compounds wherein:

each of $R_1$ and $R_3$ is hydrogen;

Z is —$C(CH_3)_2(CH_2)_6$ and W is hydrogen;

Z is $C_{4-7}$ alkylene and W is phenyl;

Z is -O-alkylene having 7 to 9 carbon atoms and W is hydrogen;

Z is -O-alkylene having from 4 to 5 carbon atoms and W is phenyl;

A is hydrogen and B is hydroxy (cis- and trans- forms);

A and B taken together are oxo;

$R_2$ = hydrogen, methyl, propyl or propenyl;

$R_3$ = hydrogen; and $R_4$ = hydrogen or methyl.

Especially preferred are the saturated cycloalkyl compounds of formulae IB and IC wherein $R_1$, $R_2$, $R_3$, $R_4$, Z and W are as defined for the preferred compounds and A and B taken individually are hydrogen and hydroxy, respectively.

Also as regards analgesic activity, a specially preferred group of compounds are those preferred compounds mentioned above wherein $R_2$ is methyl, propyl or propenyl and $R_4$ is hydrogen.

Further, the favored and preferred classes of intermediates described herein are those which serve as intermediates for the favored and preferred compounds mentioned above.

DETAILED DESCRIPTION OF THE INVENTION

The saturated cycloalkyl compounds of this invention having formula I wherein $R_3$ is hydrogen are prepared from the appropriate 2-bromo-5-(Z-W substituted)phenol by a series of reactions which comprises as first step protection of the phenolic group. Suitable protecting groups are those which do not interfere with the subsequent reactions and which can be removed under conditions which do not cause undesired reactions at other sites of said compounds or of products produced therefrom. Representative of such protective groups are methyl, ethyl, benzyl or substituted benzyl wherein the substituent is, for example, alkyl having from one to four carbon atoms, halo (Cl, Br, F, I) and alkoxy having from one to four carbon atoms. The ether protecting, or blocking, groups can be removed through the use of hydrobromic acid in acetic acid or hydrobromic acid, 48% aqueous. The reaction is conducted at elevated temperatures nd desirably at the reflux temperature. However, when Z is —$(alk_1)_m$—O—$(alk_2)_n$—, acids such as polyphosphoric acid or trifluoroacetic acid must be used to avoid cleavage of the ether linkage. Other reagents such as hydriodic acid, pyridine hydrochloride or hydrobromide can be used to remove protecting ether groups such as methyl or ethyl groups. When the protecting groups are benzyl or substituted benzyl groups, they can be removed by catalytic hydrogenolysis. Suitable catalysts are palladium or platinum, especially when supported on carbon. Alternatively they can be removed by solvolysis using trifluoroacetic acid. A further procedure comprises treatment with n-butyllithium in a reaction-inert solvent at room temperature.

The exact chemical structure of the protecting group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy groups. Methyl and benzyl are favored protecting groups since they are readily removed.

The protected 2-bromo-5-(Z-W substituted)phenol is then reacted with magnesium in a reaction-inert solvent and generally in the presence of a promoter, e.g., cuprous salts such as the chloride, bromide and iodide (to promote 1,4-addition) with the appropriate 4-$R_2$-2-cycloalken-1-one (e.g., 4-$R_2$-2-cyclohexen-1-one). Suitable reaction-inert solvents are cyclic and acyclic ethers such as, for example, tetrahydrofuran, dioxane and dimethyl ether of ethylene glycol (diglyme). The Grignard reagent is formed in known manner, as, for example, by refluxing a mixture of one molar proportion of the bromo reactant and two molar proportions of magnesium in a reaction-inert solvent, e.g. tetrahydrofuran. The resulting mixture is then cooled to about 0° C. to −20° C., and cuprous iodide added followed by the appropriate 2-cycloalken-1-one at a temperature of from about 0° C. to −20° C. The amount of cuprous iodide used is not critical but can vary widely. Molar proportions ranging from about 0.2 to about 0.2 moles per mole of bromo reactant afford satisfactory yields of the cycloalkanone wherein the phenolic hydroxy group is protected (formulae IA–ID, $R_1$=a protecting group; $R_3$=H; A+B=oxo).

The protected cycloalkanone is then treated with an appropriate reagent to remove the protecting group. The benzyl group is conveniently removed by the method described above. If the protecting group is an alkyl group (methyl or ethyl) it is removed by the above-mentioned methods or by treatment with, for example, pyridine hydrochloride.

When $R_2$ is an alkenyl group, the cycloalkenones thus produced serve as intermediates for preparation of the corresponding cycloalkenones (IA–ID) wherein $R_2$ is alkyl.

The cycloalkanol compounds having formula I are prepared from the protected cycloalkanones by reduction. Sodium borohydride is favored as reducing agent in this step since it not only affords satisfactory yields of the desired product, but retains the protecting group on the phenolic hydroxy group, and reacts slowly enough with hydroxylic solvents (methanol, ethanol, water) to permit their use as solvents. Temperatures of from about −40° C. to about 30° C. are generally used. Lower temperatures, even down to about −70° C., can be used to increase selectivity of the reduction. Higher temperatures cause reaction of the sodium borohydride with the hydroxylic solvent. If higher temperatures are desired, or required for a given reduction, isopropyl alcohol or the dimethyl ether of diethylene glycol are used as solvents. Sometimes favored as reducing agent is potassium tri-sec-butyl borohydride since it favors stereoselective formation of the trans-1,3-phenylcycloalkanol. The reduction is conducted in dry tetrahydrofuran at a temperature below about −50° C. using equimolar quantities of the ketone compound and reducing agent.

Reducing agents such as lithium borohydride, diisobutylaluminum hydride or lithium aluminum hydride which can also be used require anhydrous conditions and non-hydroxylic solvents, such as 1,2-dimethoxyethane, tetrahydrofuran, diethyl ether, dimethyl ether of ethylene glycol.

The cycloalkanols of formula I wherein A is hydrogen and each of B and $OR_1$ is hydroxy can, of course, be obtained directly by catalytic reduction of the protected cycloalkanone over palladium-on-carbon or by catalytic reduction or chemical reduction of the unprotected cycloalkanone (formula I, A+B=oxo, $OR_1$=OH) using the reducing agents described above.

In actual practice it is preferred to produce the unprotected cycloalkanols of formula I (A=H, B=$OR_1$=OH) via reduction of the benzyl protected cycloalkanones (formula I, A+B=oxo, $OR_1$=benzyloxy) as described above, since it permits stereochemical control of the reduction and formation of the cis-hydroxy epimer as the major product and thus facilitates separation and purification of the epimeric alcohols.

Compounds of formulae IA–ID wherein the double bond is at the 2,3-positions are prepared by Grignard reaction of the appropriate protected 2-bromo-5-(Z-W substituted)phenol with a 3-alkoxy-2-cycloalken-1-one (having from one to four carbon atoms in the alkoxy group) in a reaction-inert solvent at a temperature of from about −30° C. to +10° C. The protected cycloalkenone compound thus produced is then deprotected as described above and reduced to the corresponding cycloalkenol. Alternatively, the protected cycloalkenone is reduced chemically, e.g. using sodium borohydride, to the protected cycloalkenol which is then deprotected to regenerate the phenolic hydroxy group.

Compounds of formulae IA–ID wherein the double bond is at the 3,4-position are prepared from compounds of formulae IA–ID wherein A+B is oxo and the double bond is at the 2,3-position. The process comprises ketalization of the appropriate 2,3-unsaturated formulae IA–ID compounds with an alkylene glycol having from two to four carbon atoms in the presence of a dehydrating agent such as p-toluenesulfonic acid in a solvent such as benzene which permits azeotropic removal of by-product water. Isomerization of the double bond to the 3,4-unsaturated ketal derivative occurs. Deketalization by mild acid treatment affords the 3,4-unsaturated compounds of formulae IA–ID wherein A+B represent oxo. Reduction of the oxo group as described above affords the corresponding alcohol.

The protected cycloalk-2-enones (formulae IA–ID, A+B=oxo, $R_1$=protecting group) also serve as intermediates for formula I compounds wherein $R_3$ is methyl. Introduction of the $R_3$ substituent is achieved by conjugate addition of dimethylcopper lithium to the appropriate cycloalk-2-enone. The process comprises reacting the appropriate protected cycloalkenone with dimethylcopper lithium, in a reaction-inert solvent, such as cyclic and acyclic ethers and especially in tetrahydrofuran, at from about 0° C. to −20° C. The organometallic reagent effects 1,4-addition to the protected cycloalkenone with formation of a tertiary carbon. The $R_3$-substituted protected cycloalkanone is then deprotected and reduced, or reduced and then deprotected according to procedures described above. The 1,2-addition product is also formed.

Compounds of formula IB wherein the cycloalkyl moiety is saturated and wherein $R_4$ is other than hydrogen are prepared by reacting the appropriate 2-bromo-5-(Z-W-substituted)phenol, in which the phenolic group is suitably protected as described above, with magnesium to form the Grignard reagent as previously described. The resulting Grignard reagent is then treated, without isolation, at a reduced temperature, e.g., about +10° C. to about −20° C. with N,N-dimethylformamide. The reaction mixture is then allowed to warm to room temperature and the product, a protected 2-hydroxy-4-(Z-W-substituted)benzaldehyde, recovered by known methods. The benzaldehyde derivative is then converted to an ω-(2-hydroxy-4-(Z-W-substituted)phenyl)-3-alken-one via the Wittig reaction with the appropriate 1-triphenylphosphoranylidene-2-alkanone in a reaction-inert solvent at a temperature of from about room temperature to the reflux temperature of the solvent. The 2-propanone derivative mentioned above permits formation of the cyclohexyl moiety. The aryl alken-one thus produced is then reacted with a dialkylmalonate, preferably one in which the alkyl groups have from 1–4 carbon atoms, to cyclize the alken-one. The reaction is conducted in a reaction-inert solvent, such as an alcohol having from 1–4 carbon atoms, at a temperature of from about 25° C. to about the reflux temperature of the solvent.

The carbalkoxy substituted cycloalkanedione compound produced is then decarboxylated by treatment with aqueous sodium or potassium hydroxide at an elevated temperature; that is, from about 50° C. to 100° C., and the cycloalkanedione derivative isolated by standard, known methods. It is then ketalized by reaction with methanol, or other alcohol having up to 4 carbon atoms, or an alkylene glycol having from 2 to 4 carbon atoms, in the presence of a dehydrating acid such as p-toluenesulfonic acid.

In the case of the cyclohexyl derivative, the 3-methoxy-2-cyclohexene-1-one derivative is then reacted with lithium aluminum hydride in a reaction-inert solvent such as diethyl ether, dioxane, tetrahydrofuran or diglyme at a temperature of about −10° C. to 10° C. and worked up with dilute mineral acid. The resulting aryl substituted-2-cyclohexene-1-ones are then treated with the appropriate dialkylcopper lithium in a suitable reaction-inert solvent such as hexane, diethyl ether, or mixtures of these solvents or in cyclic ethers such as tetrahydrofuran at a temperature of from about 0° C. to about −20° C. The protected 3-[4-(Z-W)-substituted-2-hydroxypheny]-5-$R_4$ cycloalkanone is then deprotected and reduced, or reduced and then deprotected, according to procedures previously described.

Alternatively, reaction of the 5-[2-benzyloxy-4-(Z-W)phenyl]-3-alkoxy-2-cyclohexen-1-ones with the appropriate Grignard reagent $R_4MgBr$ followed by acid hydrolysis produces the corresponding 5-[2-benzyloxy-4-(Z-W)phenyl]-3-$R_4$-2-cyclohexen-1-ones which are then catalytically reduced to the corresponding cyclohexanones. Debenzylation, as described above, affords the 5-[2-hydroxy-4-(Z-W)-phenyl]-3-$R_4$-cyclohexanones which are then reduced as described above to the corresponding cyclohexanols.

Compounds of formula I-C wherein the cycloalkyl moiety is saturated and wherein $R_4$ is other than hydrogen are prepared by ring expansion of the cyclohexyl derivative. Reaction of the appropriate 5-[2-benzyloxy-4-(Z-W)-phenyl]-3-$R_4$-cyclohexanone with lithium dibromomethane in a reaction-inert solvent such as diethyl ethers affords the 1-dibromomethyl-5-[2-benzyloxy-4-(Z-W)-phenyl]-3-$R_4$-cyclohexanol. Further reaction of the 1-dibromomethyl cyclohexanol in a reaction-inert solvent such as tetrahydrofuran with n-butyl lithium yields 3-[2-hydroxy-4-(Z-W)-phenyl]-5-$R_4$-cycloheptanones which are then deprotected and reduced, or reduced and deprotected, according to procedures previously described.

Compounds of formula I-D wherein the cycloalkyl moiety is saturated and wherein $R_4$ is other than hydrogen are prepared by ring expansion of the cycloheptyl derivative, according to procedures previously described.

When $R_4$ is hydrogen in structure IA–IC it is possible, according to procedures previously described, to cause ring expansion of these structures to the one methylene larger ring; i.e., to IB–ID, respectively.

The 2-bromo-5-Z-W substituted)phenol reactants are prepared by bromination of the appropriate 3-(Z-W substituted)phenol according to standard procedures as, for example, by treatment with bromine in carbon tetrachloride at a temperature of from about 20° C.–30° C. The necessary 3-(Z-W substituted)phenols, if not known compounds, are prepared by procedures illustrated herein. A convenient method for preparing such reactants wherein the Z moiety if alkylene or (alk$_1$-)$_m$—O—(alk$_2$)$_n$— comprises the Wittig reaction on an appropriate aldehyde such as 2-(3-hydroxyphenyl)-2-methyl propionaldehyde, the hydroxy group of which is protected by benzyl ether formation. The said aldehyde is then treated with the appropriate alkyltriphenylphosphonium bromide, the alkyl group of which extends the propionaldehyde group to the desired length. In a typical procedure, the aldehyde reactant is added to a slurry of sodium dimsyl and alkyl triphenylphosphonium bromide in dimethyl sulfoxide at a temperature below 30° C., e.g. from about 10° C. to 30° C. When reaction is complete, the alkene substituted protected phenol is recovered by known methods. Hydrogenation of the alkene over palladium-on-carbon then affords the desired 3-(Z-W substituted)phenol benzyl ether. Judicious choice of the starting (3-hydroxyphenyl)substituted aldehyde and alkyl triphenylphosphonium bromide reactants affords the required 3-(Z-W substituted)phenol reactants.

Preparation of the appropriate 4-$R_2$-2-cycloalken-1-one allows synthesis of the structures of formulae IA-D wherein $R_4$ is hydrogen, according to procedures previously described. Reaction of the appropriate 1,3-cycloalkan-dione with an alcohol of from one to four carbon atoms and an acid catalyst such as p-toluenesulfonic acid in a reaction-inert solvent such as benzene or toluene, and with an apparatus for water separation at temperatures where the reaction solvent will reflux affords 3-alkoxy-2-cycloalken-1-ones. Reacting the appropriate 3-alkoxy-2-cycloalken-1-one with lithiodiisopropylamide in a reaction-inert solvent such as tetrahydrofuran in the presence of hexamethylphosphoramide and the appropriate $R_2X$, where X is bromide or iodide or some other suitable leaving group, yields 4-$R_2$-3-alkoxy-2-cycloalken-1-ones. The 4-$R_2$-3-alkoxy-2-cycloalken-1-one is then reacted with lithium aluminum hydride in a reaction-inert solvent such as diethyl ether at temperatures of about $-10°$ C. to 10° C. and worked up with dilute mineral acid. The resulting 4-$R_2$-2-cycloalken-1-one is then transformed according to procedures already described.

Compounds of formula IB-ID wherein the cycloalkyl moiety is saturated and wherein each of $R_2$ and $R_4$ is other than hydrogen are prepared by reacting the appropriate 5-[2-benzyloxy-4-(Z-W)phenyl]-3-methoxy-2-cyclohexen-1-one with lithiodiisopropylamide in a reaction-inert solvent at a low temperature, e.g., $-50°$ C. to $-78°$ C. Hexamethylphosphoramide and the appropriate $R_2$ iodide (wherein $R_2$ is other than hydrogen) are then added to produce a 5-[2-benzyloxy-4-(Z-W)-phenyl]-3-methoxy-6-$R_2$-2-cyclohexen-1-one. Further reaction of said compound with the appropriate Grignard reagent $R_4'$MgX (wherein $R_4'$ is alkyl) under usual Grignard reaction conditions affords a 3-[2-benzyloxy-4-(Z-W)phenyl]-4-$R_2$-5-$R_4'$-5-cyclohexen-1-one. Debenzylation and reduction of said compound according to procedures described above provides the desired 3-[2-hydroxy-4-(Z-W)-phenyl]-4-$R_2$-5-$R_4'$-cyclohexanol. Reduction of the double bond of the 3-[2-benzyloxy-4-(Z-W)phenyl]-4-$R_2$-5-$R_4'$-5-cyclohexen-1-one over Pd/C affords the corresponding saturated cyclohexanone derivative. These latter derivatives serve as intermediates for preparation of corresponding cycloheptanone and cyclooctanone derivatives by the ring expansion procedure described above.

A convenient procedure which permits selective alkylation of 3-(2,4-dihydroxyphenyl)cycloalkanones at the 4-hydroxy group comprises, as the first step, conversion of the 3-(2,4-dihydroxyphenyl)cycloalkanone to a ketal. The conversion is accomplished according to well-known procedures for ketalization, such as reaction of the 3-(2,4-dihydroxyphenyl)cycloalkanone with an alcohol, especially an alcohol having from one to four carbon atoms, in the presence of an acid, such as sulfuric acid, p-toluenesulfonic acid, hydrogen chloride, under conditions which remove the by-product water. A favored procedure comprises reaction of the 3-(2,4-dihydroxyphenyl)cycloalkanone with an orthoformic ester in solution in an alcohol corresponding to the alcohol moiety of the orthoformic ester. Trimethyl orthoformate and methanol ae favored reactants along with concentrated sulfuric acid, anhydrous hydrogen chloride, or ammonium chloride as catalyst.

The ketal thus produced is then alkylated by reaction with an appropriate alkylating agent such as W-Z-X wherein W and Z are as defined above, and X is selected from the group consisting of chloro, bromo, mesyloxy ($CH_3$—$SO_2$—O) and tosyloxy (p-$CH_3$—$C_6H_4$—$SO_2$—O—) in the presence of an acid acceptor, e.g. sodium or potassium carbonate. The akylated ketal is then deketalized according to known procedures by treatment with aqueous acid.

A further procedure for making 3-(Z-W substituted)-phenols wherein Z is alkylene or (alk$_1$)—O—(alk$_2$)$_n$— comprises the Wittig reaction on an appropriate phenolic aldehyde or ketone, e.g., 3-hydroxybenzaldehyde or a 3-(hydroxyphenyl)alkyl ketone, in which the phenolic hydroxy group is protected as by conversion to the benzyl, methyl or ethyl ether. By choice of appropriate reactants, compounds having straight or branched alkylene groups (Z) can be produced. When a ketone, e.g. 3-hydroxyacetophenone, is used as reactant, compounds wherein Z has a methyl group on the carbon atom adjacent to the phenyl group are obtained.

Substitution of a methyl or ethyl group at other sites, e.g., the beta-carbon atom of the alkylene group, is achieved by choice of the appropriate carboalkoxy alkylidene triphenylphosphorane, e.g, $(C_6H_5)_3P=C(R')—COOC_2H_5$. The unsaturated ester thus produced is reduced to the corresponding alcohol by reaction with lithium aluminum hydride. Alternatively, when the phenolic protecting group is other than benzyl (e.g. methyl), the alcohol is produced by catalytic reduction of the unsaturated ester using palladium-carbon, followed by treatment of the saturated ester thus produced with lithium aluminum hydride. Conversion of the alcohol thus produced to the corresponding tosylate or mesylate followed by alkylation of the tosylate or mesylate with an alkali metal salt of the appropriate $HO-(alk_2)-W$ reactant, and finally removal of the protecting group affords the desired 3-(Z-W substituted)phenol A variation of the above sequence comprises bromination of the alcohol rather than converting it to a tosylate or mesylate. Phosphorous tribromide is a convenient brominating agent. The bromo derivative is then reacted with the appropriate $HO-(alk_2)-W$ in the presence of a suitable base (Williamson ether synthesis).

The bromo compounds also serve as valuable intermediates for increasing the chain length of the alkylene moiety in the above sequence to give compounds wherein Z is -alkylene-W. The process comprises treating the bromo derivative with triphenylphosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

An alternative method for introducing an alkyl or aralkyl group into the aromatic nucleus, and specifically such a group wherein the carbon atom adjacent the aromatic nucleus is a tertiary carbon atom, comprises acid catalyzed electrophilic aromatic substitution of quaiacol with a tertiary alcohol in the presence of an acid, e.g. methane sulfonic acid. The general procedure consists of reacting a mixture of methane sulfonic acid and equimolar amounts of quaiacol and tertiary alcohol at temperatures of from about 30° C. to about 80° C. until reaction is substantially complete. The product is isolated by pouring the reaction mixture onto ice followed by extraction with a suitable solvent such as methylene chloride. The 2-methoxy-4-alkyl phenol is then converted to the desired 3-alkyl phenol by removal of the phenolic hydroxy group. The process comprises converting the hydroxy group to a dialkyl phosphate group by reaction with a dialkyl chlorophosphonate, e.g. diethyl chlorophosphonate, or with diethyl phosphonate and triethylamine. Treatment of the dialkyl phosphate with lithium/ammonia followed by demethylation of the resulting alkylated methyl ether with boron tribromide or pyridine hydrochloride or other known demethylating agents affords the desired 3-alkylphenol. A convenient method for preparing compounds of this invention wherein $—Z—W$ is $—O—(alk_2)_n—W$ comprises the use of 4-bromo resorcinol as starting material. The process comprises protecting the two hydroxy groups of the resorcinol by benzylation according to standard procedures. The benzyl group is favored as protecting group in this method since it can easily be removed by catalytic hydrogenation without cleaving the ether group $—O—(alk_2)_n—W$. Other protecting groups such as alkyl (e.g., methyl or ethyl) can, of course, also be used. However, the benzyl protecting group is favored since it gives rise to fewer side reactions. The protected 4-bromo resorcinol is then subjected to the Grignard reaction and reacted with the appropriate cycloalkenone in a reaction-inert solvent in the manner described above. The 3-(2,4-dibenzyloxyphenyl)cycloalkanone thus produced is then subjected to catalytic hydrogenation over palladium-on-carbon to produce the corresponding 3-(2,4-dihydroxyphenyl)-cycoalkanone which exists in equilibrium with its hemiketal. The hemiketal is then converted to the corresponding $C_{1-4}$ alkyl, e.g., methyl, ketal by reaction with, for example, a trialkyl orthoformate, such as trimethylorthoformate in a suitable solvent such as a $C_{1-4}$ alcohol, e.g methanol, in the presence of concentrated sulfuric acid. The thus-produced alkyl ketal is then alkylated with the appropriate alkyl or aralkyl methane sulfonate or tosylate in the presence of anhydrous sodium or potassium carbonate in a suitable reaction-inert solvent such as N,N-di-methylformamide at a temperature of from about 75°-100° C. This method has the advantage of permitting the use of simpler compounds throughout the entire sequence of reactions. The O-alkylated or aralkylated ketal is then deketalized by reaction with, for example, hydrochloric acid, to produce the corresponding 3-(2-hydroxy-4-[O-(alk$_2$)$_n$]-phenyl)cycloalkanone which exists in equilibrium with its hemiketal.

Since compounds having formulae IA-ID in which A and B taken together are oxo and $R_1$ is hydrogen exist in solution in equilibrium with the hemiketal form and some, in the crystalline state, exist substantially completely in the hemiketal form, compounds of formulae IA-ID wherein A and B taken together are oxo and $R_1$ is hydrogen are intended to embrace the hemiketal as well as the keto form.

Compounds of this invention wherein A and B taken together are methylene are readily prepared from the corresponding oxo compounds via the Wittig reaction with methylene triphenylphosphorane or other appropriate methylide. The usual procedure comprises generating the Wittig reagent; that is, the methylene, in situ and, immediately following generation of the methylide, reacting it with the appropriate oxo compound. A convenient procedure for generating the methylide comprise reacting sodium hydride with dimethyl sulfoxide (sodium dimsyl) at a temperature of from about 50°-80° C., usually until evolution of hydrogen ceases, followed by reacting the resulting solution of methyl sulfinyl carbanion (dimsyl) with, for example, methyl triphenyl phosphonium bromide at a temperature of from about 10° C. to about 80° C. To the thus-produced solution of the ylide is then added the appropriate oxo compound and the mixture stirred at temperatures ranging from about room temperature to 80° C. The methylene compound thus produced is isolated by known procedures. Hydroboration-oxidation of the methylene compound then affords the hydroxymethyl derivative as is exemplified herein. Borane in tetrahydrofuran is favored for the hydroboration step since it is commercially available and gives satisfactory yields of the desired hydroxymethyl compound. The reaction is generally conducted in tetrahydrofuran or diethylene glycol dimethyl ether (diglyme). The borane product is not isolated but is directly oxidized with alkaline hydrogen peroxide to the hydroxymethyl compound.

Other methods of generating the methylide are, of course, known and can be used in lieu of the above-described procedure. Typical procedures are described by Maercker, *Organic Reactions*, 14, 270 (1965). In the oxo compounds having formulae IA-ID, the phenolic hydroxy group can be protected if desired as, for example, by conversion to an alkanoyloxy derivative. Other protecting groups can, of course, be used. The hydroxyl group can be converted to ethers such as, for example, tetrahydropyranyl ethers. However, protection of the phenolic hydroxy group is not absolutely necessary if sufficient base is present to convert the phenolic hydroxy group to an alkoxide.

Esters of compounds of formulae IA-ID wherein $R_1$ is alkanoyl or $-CO-(CH_2)_pNR_5R_6$ are readily prepared by reacting formulae IA-ID compounds wherein $R_1$ is hydrogen with the appropriate alkanoic acid or acid of formula $HOOC-(CH_2)_pNR_5R_6$ in the presence of a condensing agent such as dicyclohexylcarbodiimide. Alternatively, they are prepared by reaction of a formulae IA-ID compound with the appropriate alkanoic acid chloride or anhydride, e.g., acetyl chloride or acetic anhydride, in the presence of a base such as pyridine.

Esters of compounds of formulae IA-ID wherein A is hydrogen and B is hydroxy or hydroxymethyl and $OR_1$ is hydroxy are prepared by acylation according to the above-described procedures. Compounds in which only the R group (R=OH, CH$_2$CH) is acylated are obtained by mild hydrolysis of the corresponding diacyl derivative, advantage being taken of the greater ease of hydrolysis of the phenolic acyl group. The thus-produced compounds can then be acylated further with a different acylating agent to produce a diesterified compound having different ester groups.

The analgesic properties of the compounds of this invention are determined by tests using nociceptive stimuli.

Tests Using Thermal Nociceptive Stimuli (a) Mouse Hot Plate Analgesic Testing

The method used is modified after Woolfe and MacDonald, *J. Pharmacol. Exp. Ther.*, 80, 300-307 (1944). A controlled heat stimulus is applied to the feet of mice on a ⅛-inch thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½-inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an MPE$_{50}$=4-5.6 mg./kg. (s.c.).

(b) Mouse Tail Flick Analgesic Testing

Tail flick testing in mice is modified after D'Amour and Smith, *J. Pharmacol. Exp. Ther.*, 72, 74-79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing an aluminum flag over the lamp is drawn back, allowing the light beam to pass through the slit and focus onto the end of the tail. A timer is simultaneously activated. The latency of a sudden flick of the tail is ascertained. Untreated mice usually react within 3-4 seconds after exposure to the lamp. The end point for protection is 10 seconds. Each mouse is tested at 0.5 and 2 hours after treatment with morphine and the test compound. Morphine has an MPE$_{50}$ of 3.2-5.6 mg./kg. (s.c.).

(c) Tail Immersion Procedure

The method is a modification of the receptacle procedure developed by Benbasset, et al., *Arch. int. Pharmacodyn.*, 122, 434 (1959). Male albino mice (19-21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 to 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. MPE$_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Deutch Med. Wschr.*, 55, 731-732 (1929) is used to ascertain the effects of the test compound on aggressive attacking responses elicited by a stimulus pinching the tail. Male albino rats (50-60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% MPE = \frac{\text{test time} - \text{control time}}{\text{cutoff time} - \text{control time}} \times 100$$

The compounds of this invention, when used as analgesics via oral or parenteral administration, are conveniently administered in composition form. Such compositions include a pharmaceutical carrier selected on the basis of the chosen route of administration and standard pharmaceutical practices. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixers which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from about 0.1 to about 750 mg. per day in single or divided doses. In many instances, it is not necessary to exceed 100 mg. daily. The favored oral dosage range is from about 1.0 to about 300 mg./day; the preferred dose is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

The compounds (drugs) described herein can be formulated for administration in solid or liquid form for oral or parenteral administration. Capsules containing drugs of this invention are prepared by mixing one part by weight of drug with nine parts of excipient such as starch or milk sugar and then loading the mixture into telescoping gelatin capsules such that each capsule contains 100 parts of the mixture. Tablets containing said compounds are prepared by compounding suitable mixtures of drug and standard ingredients used in preparing tablets, such as starch, binders and lubricants, such that each tablet contains from 0.10 to 100 mg. of drug per tablet.

Suspensions and solutions of these drugs, particularly those wherein $R_1$ (formulae I and II) is hydroxy, are often prepared just prior to use in order to avoid problems of stability of the suspensions or solution (e.g. precipitation) of the drug upon storage. Compositions suitable for such are generally dry solid compositions which are reconstituted for injectable administration.

By means of the above procedures, the analgesic activity of several compounds of this invention is determined. The compounds have the formula shown below:

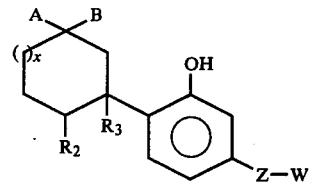

Table I: A=H, B=OH; Table II: A+B=oxo.

The following abbreviations are used in the Tables: PBQ=phenylbenzoquinone-induced writhing; TF=tail flick; HP=hot plate; RTC=rat tail clamp; and FJ=flinch jump.

Single values in the tables are $ED_{50}$'s. A number followed by a second number in parentheses reports the % protection observed at a given dose. Thus, 31(56) indicates 31% protection at a dose of 56 mg./kg. of body weight.

TABLE I

| | | | | Analgesic Activity $ED_{50}$ (mg./kg.) of % Protection (mg./kg.), Subcutaneously | | | | | | |
|---|---|---|---|---|---|---|---|---|---|---|
| x | B | $R_2$ | $R_3$ | Z | W | PBQ | HP | TF | FJ | RTC |
| 1 | cis-OH | H | H | $C(CH_3)_2(CH_2)_6$ | H | 1.1 | | 6.8 | 4.0 | 4.7 |
| 1 | trans-OH | H | H | $C(CH_3)_2(CH_2)_6$ | H | 3.8 | | | | |
| 1 | cis-OH | H | trans-$CH_3$ | $C(CH_3)_2(CH_2)_6$ | H | ≧56 | | | | |
| 1 | trans-OH | H | H | $OCH(CH_3)(CH_2)_3$ | $C_6H_5$ | 28(56) | | | | |
| 1 | cis-OH | H | H | $OCH(CH_3)(CH_2)_3$ | $C_6H_5$ | 38 | | | | |
| 2 | trans-OH | H | H | $C(CH_3)_2(CH_2)_6$ | H | 1.53 | IA@10 | 65(10) | 5.4 | 5.6 |
| 2 | cis-OH | H | H | $C(CH_3)_2(CH_2)_6$ | H | 1.5 | 27(10) | 32(10) | 3.5 | 7.7 |
| 0 | cis-OH | H | H | $C(CH_3)_2(CH_2)_6$ | H | 57(56) | | | | |
| 0 | trans-OH | H | H | $C(CH_3)_2(CH_2)_6$ | H | 36(56) | | | | |
| 1 | trans-OH | trans-$CH_3$ | H | $C(CH_3)_2(CH_2)_6$ | H | 0.5 | | | | |

TABLE I-continued

| x | B | $R_2$ | $R_3$ | Z | W | PBQ | HP | TF | FJ | RTC |
|---|---|---|---|---|---|---|---|---|---|---|
| 1 | trans-OH | H | H | $O(CH_2)_4$ | $C_6H_5$ | $\geq 56$ | | | | |
| 1 | cis-OH | H | H | $O(CH_2)_4$ | $C_6H_5$ | $\leq 56$ | | | | |
| 1 | cis-OH | trans-$CH_3$ | H | $C(CH_3)_2(CH_2)_6$ | H | $\leq 1$ | | | | |

TABLE II

| x | A + B = oxo | $R_2$ | $R_3$ | Z | W | PBQ | HP | TF | FJ | RTC |
|---|---|---|---|---|---|---|---|---|---|---|
| 1 | O | H | H | $C(CH_3)_2(CH_2)_6$ | H | 4.5 | 15.3 | | | |
| 1 | O | H | $CH_3$ | $C(CH_3)_2(CH_2)_6$ | H | 31(56) | | | | |
| 1(a) | O | H | H | $C(CH_3)_2(CH_2)_6$ | H | 20(56) | | | | |
| 1 | O | H | H | $OCH(CH_3)(CH_2)_3$ | $C_6H_5$ | $\geq 56$ | | | | |
| 1 | O | H | (b) | $C(CH_3)_2(CH_2)_6$ | H | 20(56) | | | | |
| 2 | O | H | H | $C(CH_3)_2(CH_2)_6$ | H | 2.15 | 33(10) | 58(10) | 10.8 | 4.4 |
| 0 | O | H | H | $C(CH_3)_2(CH_2)_6$ | H | 15(56) | | | | |
| 1 | O | H | H | O | H | 32(56) | | | | |
| 1 | O(c) | H | H | O | H | 43(56) | | | | |
| 1 | O | cis-$CH_3$ | H | $C(CH_3)_2(CH_2)_6$ | H | 1.51 | | | | |

(a) = benzyl ether of phenolic OH group.
(b) = $\Delta^2$-analog.
(c) = methyl ketal derivative.
IA = inactive.

Their activity as diuretic agents is determined by the procedure of Lipschitz et al., *J. Pharmacol.*, 197, 97 (1943) which utilizes rats as the test animals. The dosage range for this use is the same as that noted above with respect to the use of the herein described compounds as analgesic agents.

Antidiarrheal utility is determined by a modification of the procedure of Neimegeers et al., *Modern Pharmacology-Toxicology*, Willem van Bever and Harbans Lal, Eds., 7, 68–73 (1976). Charles River CD-1 rats (170–200 gms.) are housed in group cages 18 hours before testing. The animals are fasted overnight with water available ad libitum prior to administration of castor oil. The test drug is administered subcutaneously or orally at a constant volume of 5 ml./kg. of body weight in a 5% ethanol, 5% Emulphor EL-620 (a polyoxyethylated vegetable oil emulsifying agent available from Antara Chemicals, New York, N.Y.), and 90% saline vehicle followed one hour later with a challenge of castor oil (one ml., orally). The animals are placed in small individual cages (20.5×16×21 cm.) having suspended wire floors. A disposable cardboard sheet is placed beneath the wire floors and examined one hour after castor oil challenge for the presence or absence of diarrhea. A vehicle/castor oil treatment group serves as control for each day's testing. Results are recorded as the number of animals protected at one hour post challenge. In general, the dosage levels for use of these compounds as antidiarrheal agents parallels those with respect to their use as analgesic agents.

The tranquilizer activity of the compounds of this invention is determined by orally administering them to rats at doses of from about 0.01 to about 50 mg./kg. of body weight and observing the subsequent decreases in spontaneous motor activity. The daily dosage range in mammals is from about 0.01 to about 100 mg.

Anticonvulsant activity is determined by subcutaneously administering the test compound to male Swiss mice (Charles River) weighing 14–23 g. in a vehicle of the type used for antidiarrheal utility. The mice are used in groups of five. The day before use, the mice are fasted overnight but watered ad lib. Treatments are given at volumes of 10 ml. per kg. via a 25 gauge hypodermic needle. Subjects are treated with the test compound and, one hour after challenge, electroconvulsive shock, 50 mA. at 60 Hz. administered transcorneally. Controls are simultaneously run in which the mice are given only the vehicle as control treatment. The electroconvulsive shock treatment produces tonic extensor convulsions in all control mice with a latency of 1.5–3 seconds. Protection is recorded when a mouse exhibits no tonic extensor convulsions for 10 seconds after administration of electroconvulsive shock.

Antianxiety activity is determined in a manner similar to that for evaluating anticonvulsant activity except that the challenge convulsant is pentylenetetrazole, 120 mg./kg. administered intraperitoneally. This treatment produces clonic convulsions in less than one minute in over 95% of control mice treated. Protection is recorded when the latency to convulse is delayed at least 2-fold by a drug pretreatment.

Sedative/depressant activity is determined by treating groups of six mice subcutaneously with various doses of test agents. At 30 and 60 minutes post treatment, the mice are placed on a rotorod for one minute and evaluated for their performance on the rotorod. Inability of the mice to ride the rotorod is taken as evidence of sedative/depressant activity.

EXAMPLE 1

3-[2-Benzyloxy-4-(1,1-dimethylheptyl)-phenyl]cyclohexanone

A solution of 75.0 g. (0.193 mol.) of 2-(3-benzyloxy-4-bromophenyl)-2-methyloctane in 200 ml. of tetrahydrofuran was slowly added to 9.25 g. (0.386 mol.) of 70–80 mesh magnesium metal. The resultant mixture was refluxed for 20 minutes and then cooled to −18° C. Cuprous iodide (1.84 g., 9.7 mmoles) was added and stirring was continued for 10 minutes. To the resultant mixture was slowly added a solution of 18.5 g. (0.193 mol.) of 2-cyclohexen-1-one in 40 ml. of tetrahydrofuran at such a rate that the reaction temperature was maintained below −3° C. with salt-ice cooling. The reaction mixture was stirred 30 minutes longer (t<0° C.) and then added to 500 ml. of 2N hydrochloric acid and 2 liters of ice water. The quenched reaction was extracted three times with 500 ml. portions of ether. The combined extract was washed twice with 100 ml. portions of water, twice with 100 ml. portions of saturated sodium chloride, dried over magnesium sulfate and evaporated to an oil. The oil was purified via column chromatography on 1.6 kg. of silica gel, eluted with 20% ether-cyclohexane to yield 62.5 g. (79.7%) of product as an oil.

PMR: $\delta_{CDCl_3}{}^{TMS}$ 0.84 (m, terminal methyl), 1.27 (s, gem dimethyl), 3.32 (m, benzylic methine), 5.06 (s, benzylic methylene), 6.7–7.3 (m, ArH), and 7.32 (s, PhH).

IR: (CHCl$_3$) 1709, 1613 and 1575 cm$^{-1}$.

MS: m/e 406 (M+), 362, 321, 315 and 91.

The compounds listed below were prepared from appropriate 2-benzyloxy-4-Z-W-bromobenzenes and appropriate cycloalkenones according to the above procedure.

3-[2-Benzyloxy-4-(2-(5-phenylpentyloxy))phenyl]cyclohexanone as an oil (3.6 g., 87%) from 2-benzyloxy-4-[2-(5-phenylpentyloxy)]-bromobenzene (4.0 g., 9.4 mmols.).

PMR: $\delta_{CDCl_3}{}^{TMS}$ 1.10 (d, J=6 Hz, methyl), 3.30 (m, benzylic methine), 4.25 (m, sidechain methine), 4.93 (s, benzyl ether methylene), 6.30 (dd, J=8 and 2 Hz, ArH), 6.37 (bs, ArH), 6.88 (d, J=8 Hz, ArH), 7.23 (s, PhH) and 7.38 (bs, PhH).

IR: (CHCl$_3$) 1712, 1616 and 1592 cm$^{+1}$.

MS: m/e 422 (M+), 351, 323, 296, 278, 253, 205 and 91.

Trans-3-[2-benzyloxy-4(1,1-dimethylheptyl)phenyl]-4-methylcyclohexanone as an oil (5.11 g., 61%) from 2-benzyloxy-4-(1,1-dimethylheptyl)bromobenzene (7.83 g., 0.0201 mole) and 4-methylcyclohex-2enone (2.21 g., 0.0201 mole).

PMR: $\delta_{CDCl_3}{}^{TMS}$ 0.81 (d, J=7 Hz, C-4 methyl), 1.28 (s, gem dimethyl), 5.06 (s, benzyl ether methylene), 6.8–7.2 (m, ArH) and 7.35 (s, PhH).

IR: (CHCl$_3$) 1712, 1613 and 1575 cm$^{-1}$.

MS: m/e 420 (M+), 363, 335, 329, 273, 271 and 91.

3-[2-Benzyloxy-4-(1,1-dimethylheptyl)phenyl]cyclopentanone as an oil (3.5 g., 58%) from 2-benzyloxy-4-(1,1-dimethylheptyl)bromobenzene (6.00 g., 15.4 mmoles); Rf=0.43 (0.25 mm silica gel, eluted with 1:1 ether:hexane).

3-[2-Benzyloxy-4-(1,1-dimethylheptyl)phenyl]cycloheptanone as an oil (2.94 g.; 46%) from 2-benzyloxy-4-(1,1-dimethylheptyl)bromobenzene (6.00 g., 15.4 mmoles) and cycloheptenone (1.69 g., 15.4 mmoles).

3-(2,4-Dibenzyloxyphenyl)cyclohexanone as a solid (17.9 g., 40%), m.p. 108°–109° C.; from 1-bromo-2,4-dibenzyloxybenzene (43 g., 0.116 mole) and cyclohex-2-enone (11.1 g., 0.116 mole). The product was recrystallized from ether-pentane.

PMR: $\delta_{CDCl_3}{}^{TMS}$ 1.47–2.8 (m, methylenes), 3.37 (bm, benzylic methine), 4.98 (s, benzyl ether methylenes), 6.47 (dd, J=8 and 2 Hz, ArH), 6.53 (bs, overlaps δ6.47, ArH), 6.99 (d, J=8 Hz, ArH) and 7.31 (s, PhH).

IR: (CHCl$_3$) 1709, 1618 and 1595 cm$^{-1}$.

MS: m/e 295, 181 and 91.

Analysis: Calc'd for C$_{26}$H$_{26}$O$_3$: C, 80.80; H, 6.78%. Found: C, 80.88; H, 6.80%.

3[2-benzyloxy-4-(1,1-dimethyloctyl)phenyl]cyclohexanone as an oil (5.0 g., 46%) from 2-[3-benzyloxy-4-bromophenyl]-2-methylnonane (10.4 g., 0.0258 mol.) and 2-cyclohexen-1-one (2.48 g., 0.0258 mol.).

PMR: $\delta_{CDCl_3}{}^{TMS}$ 0.83 (m, terminal sidechain methyl), 1.23 (s, gem dimethyl), 3.4 (m, benzylic methine), 5.11 (s, benzyl ether methylene), 6.92 (d, J=8 and 2 Hz, ArH), 6.92 (d, J=2 Hz, ArH), 7.17 (d, J=8 Hz, ArH) and 7.42 (bs, PhH).

IR: (CHCl$_3$) 1715, 1618 and 1577 cm$^{-1}$.

MS: m/e 420 (M+), 377, 329 and 321.

3-[2-benzyloxy-4-t-butylphenyl]cyclohexanone as an oil (27.6 g., 58%) from 2-(3-benzyloxy-4-bromophenyl)-2-methylpropane (45.4 g., 0.142 mole) and 2-cyclohexen-1-one (13.9 g., 0.145 mole).

PMR: $\delta_{CDCl_3}{}^{TMS}$ 1.31 (s, t-butyl), 5.10 (s, benzyl ether methylene) and 6.8–7.4 (m, ArH and PhH).

IR: (CHCl$_3$) 1724, 1623 and 1582 cm$^{-1}$.

MS: 336 (M+), 321, 293, 245 and 91.

3-[2-benzyloxy-4-(1,1-dimethylpropyl)phenyl]cyclohexanone as an oil (15.8 g., 63%) from 2-(3-benzyloxy-4-bromophenyl)-2-methylbutane (24.0 g., 0.0721 mole) and 2-cyclohexen-1-one (7.06 g., 0.0735 mole).

PMR: $\delta_{CDCl_3}{}^{TMS}$ 0.67 (t, J=7 Hz, terminal methyl), 1.23 (s, gem dimethyl), 5.10 (s, benzyl ether methylene), 6.92 (d, J=2 Hz, ArH), 6.92 (dd, J=8 and 2 Hz, ArH), 7.17 (d, J=8 Hz, ArH) and 7.42 (bs, PhH).

IR: (CHCl$_3$) 1718, 1618 and 1575 cm$^{-1}$.

MS: m/e 350 (M+), 335, 321, 307, 259 and 91.

3-[2-benzyloxy-4-(1,1-dimethylbutyl)phenyl]cyclohexanone as an oil (15.1 g., 42%) from 2-(3-benzyloxy-4-bromophenyl)-2-methylpentane (34.8 g., 0.100 mole) and 2-cyclohexen-1-one (10.5 g., 0.110 mole).

PMR: $\delta_{CDCl_3}{}^{TMS}$ 0.80 (m, terminal methyl), 1.22 (s, gem dimethyl), 5.07 (s, benzyl ether methylene), 6.86 (d, J=2 Hz, ArH), 6.86 (dd, J=8 and 2 Hz, ArH), 7.08 (d, J=8 Hz, ArH) and 7.34 (bs, PhH).

IR: (CHCl$_3$) 1736, 1631 and 1592 cm$^{-1}$.

MS: m/e 364 (M+), 321, 273 and 91.

Trans-3[2-Benzyloxy-4-(1,1-dimethylheptyl)phenyl]4-(2-propenyl)cyclohexanone as an oil (58.3 g., 70%) from 1-bromo-2-benzyloxy-4-(1,1-dimethylheptyl)bromobenzene (73.0 g., 0.188 mole) and 4-(2-propenyl)-2-cyclohexen-1-one (25.5 g., 0.188 mole).

IR: (CHCl$_3$) 1712, 1645, 1613 and 1575 cm$^{-1}$.

MS: m/e 446 (M+), 360, 354 and 91.

PMR: $\delta_{CDCl_3}{}^{TMS}$ 0.82 (m, terminal methyl), 1.23 (s, gem dimethyl), 4.7–5.1 (m, vinyl H), 5.02 (s, benzylic methine), 5.3–6.1 (m, vinyl H), 6.79 (d, J=2 Hz, ArH), 6.82 (dd, J=8 and 2 Hz, ArH) and 7.0 (d, J=8 Hz, ArH).

3-[2-Benzyloxy-4-(1,1-dimethylpentyl)phenyl]cyclohexanone as an oil (11.5 g., 37%) from 2-(3-benzyloxy-4bromophenyl)-2-methylhexane (29.6 g., 0.0818 mole) and 2-cyclohexen-1-one (8.63 g., 0.09 mole).

IR: (CHCl$_3$) 1730, 1629 and 1592 cm$^{-1}$.

MS: m/e 378 (M+), 335, 321, 287 and 91.

PMR: $\delta_{CDCl_3}{}^{TMS}$ 0.82 (m, terminal methyl), 1.23 (s, gem dimethyl), 3.35 (m, benzylic methine), 5.10 (s, benzylic methylene), 6.90 (dd, J=8 and 2 Hz, ArH), 6.90 (d, J=2 Hz, ArH), 7.13 (d, J=8 Hz, ArH) and 7.38 (bs, Ph).

3-[2-Benzyloxy-4-(1,1-dimethylhexyl)phenyl]cyclohexanone as an oil (11.0 g., 35%) from 2-(3-benzyloxy-4-bromophenyl)-2-methylheptane (30.2 g., 0.0806 mole) and 2-cyclohexen-1-one (8.5 g., 0.0886 mole).

IR: (CHCl$_3$) 1715, 1623 and 1585 cm$^{-1}$.

MS: m/e 392 (M+), 348, 321, 301, 259 and 91.

PMR: $\delta_{CDCl_3}^{TMS}$ 0.81 (m, terminal methyl), 1.22 (s, gem dimethyl), 3.4 (m, benzylic methine), 5.08 (s, benzylic methylene), 6.88 (dd, J=8 and 2 Hz, ArH), 6.88 (d, J=2 Hz, ArH), 7.10 (d, J=8 Hz, ArH) and 7.37 (bs, ArH).

3-[2-Benzyloxy-4-(1,1-dimethylnonyl)phenyl]cyclohexanone as an oil (13.5 g., 43%) from 2-(3-benzyloxy-4-bromophenyl)-2-methyldecane (30.5 g., 0.073 mole) and 2-cyclohexen-1-one (7.71 g., 0.0803 mole).

IR: (CHCl$_3$) 1715, 1623 and 1582 cm$^{-1}$.
MS: m/e 434 (M+), 342, 321 and 91.
PMR: $\delta_{CDCl_3}^{TMS}$ 0.85 (m, terminal methyl), 1.24 (s, gem dimethyl), 3.4 (m, benzylic methine), 5.09 (s, benzylic methylene), 6.88 (dd, J=8 and 2 Hz, ArH), 6.88 (d, J=2 Hz, ArH), 7.11 (d, J=8 Hz, ArH) and 7.37 (bs, Ph).

3-[2-Benzyloxy-4-(1,1-dimethyldecyl)phenyl]cyclohexanone as an oil (7.0 g., 17%) from 2-(3-benzyloxy-4-bromophenyl)-2-methylundecane (40.0 g., 0.0928 mole) and 2-cyclohexen-1-one (9.8 g., 0.102 mole).

IR: (CHCl$_3$) 1715, 1623 and 1585 cm$^{-1}$.
MS: m/e 448 (M+), 321 and 91.
PMR: $\delta_{CDCl_3}^{TMS}$ 0.84 (m, terminal methyl), 1.23 (s, gem dimethyl), 3.5 (benzylic methine), 5.02 (s, benzylic methylene), 6.77 (dd, J=8 and 2 Hz, ArH), 6.77 (d, J=2 Hz, ArH), 7.13 (d, J=8 Hz, ArH) and 7.38 (bs, Ph).

3-[2-Benzyloxy-4-(1,1-dimethylundecyl)phenyl]cyclohexanone as an oil (11.5 g., 40%) from 2-(3-benzyloxy-4-bromophenyl)-2-methyldodecane (27.5 g., 0.062 mole) and 2-cyclohexen-1-one (6.68 g., 0.0682 mole).

IR: (CHCl$_3$) 1718, 1623 and 1585 cm$^{-1}$.
MS: m/e 462 (M+), 417, 371, 321 and 91.
PMR: $\delta_{CDCl_3}^{TMS}$ 0.89 (m, terminal methyl), 1.26 (s, gem dimethyl), 3.4 (m, benzylic methine), 5.11 (s, benzylic methylene), 6.89 (dd, J=8 and 2 Hz, ArH), 6.89 (d, J=2 Hz, ArH), 7.12 (d, J=8 Hz, ArH) and 7.37 (bs, Ph).

3-[2-Benzyloxy-4-(1,1-dimethylheptyl)phenyl]cyclooctanone as an oil (10.6 g., 63%) from 2-(3-benzyloxy-4-bromophenyl)-2-methyloctane (15.0 g., 38.6 mmole) and 2-cycloocten-1-one (4.78 g., 38.6 mmole).

IR: (CHCl$_3$) 1715, 1629 and 1587 cm$^{-1}$.
MS: m/e 434 (M+), 477, 363, 349, 343, 326 and 91.
PMR: $\delta_{CDCl_3}^{TMS}$ 0.83 (m, terminal methyl), 3.7 (bm, benzylic methine), 5.06 (s, benzylic methylene) and 6.7–7.5 (m, ArH).

EXAMPLE 2

3-[4-(1,1-Dimethylheptyl)-2-hydroxyphenyl]cyclohexanone

A mixture of 19.5 g. (0.0468 mol.) of 3-[2-benzyloxy-4-(1,1-dimethylheptyl)phenyl]cyclohexanone, 12.3 g. of sodium bicarbonate, 3.00 g. of 10% palladium-on-carbon and 250 ml. of ethanol was stirred under one atmosphere of hydrogen pressure for 1.5 hours. The reaction mixture was then filtered through diatomaceous earth with ethyl acetate and the filtrate evaporated to a solid. The crude solid was purified via column chromatography on 280 g. of silica gel eluted with 20% ethercyclohexane to yield a solid. Recrystallization of this solid from aqueous methanol gave 9.1 g. (62%) of the title product, m.p. 87° C., principally in the hemiketal form.

PMR: $\delta_{CDCl_3}^{TMS}$ 0.87 (m, terminal methyl), 1.27 (s, gem dimethyl), 1.0–2.2 (several multiplets), 3.21 (two proton multiplet) and 6.92 (m, ArH).

IR: (KBr) 3226, 1629 and 1580 cm$^{-1}$. (CHCl$_3$) 3571, 3289, 1704, 1623 and 1575 cm$^{-1}$.
MS: m/e 316 (M+), 298, 273 and 231.
Analysis: Calc'd for C$_{21}$H$_{32}$O$_2$: C, 79.70; H, 10.19. Found: C, 79.69; H, 9.89.

The above procedure was repeated but using the appropriate reactants of Example 1 to produce the following products.

3-[4-(1,1-Dimethylheptyl)-2-hydroxyphenyl]-3-methylcyclohexanone as an oil (54 mg., 86%) from 80 mg. (0.19 mmole) of 3-[2-benzyloxy-4-(1,1-dimethylheptyl)phenyl]-3-methylcyclohexanone.

IR: (CHCl$_3$) 3597, 3390, 1623 and 1572 cm$^{-1}$.
MS m/e 330 (M+), 315, 287 and 245.

Trans-3-[4-(1,1-dimethylheptyl)-2-hydroxyphenyl]-4-methylcyclohexanone (825 mg., 99%), m.p. 62°–64° C. (recrystallized from pentane) from trans-3-[2-benzyloxy-4-(1,1-dimethylheptyl)phenyl]-4-methylcyclohexanone (1.05 g., 2.50 mmole).

PMR: $\delta_{CDCl_3}^{TMS}$ 0.84 (m, terminal sidechain methyl), 1.28 (s, gem dimethyl) and 6.75–7.2 (M, ArH).
IR: (CHCl$_3$) 3571, 3333, 1721 (weak), 1626 and 1577 cm$^{-1}$.
MS: m/e 330 (M+), 312, 288, 273, 245, 203 and 161.
Analysis: Calc'd for C$_{22}$H$_{34}$O$_2$: C, 79.97, H, 10.37. Found: C, 80.33; H, 10.30.

3-[4-(1,1-Dimethylheptyl)-2-hydroxyphenyl]cyclopentanone (0.54 g., 46%), m.p. 61°–62° C. (from pentane) from 3-[2-benzyloxy-4-(1,1-dimethylheptyl)phenyl]-cyclopentanone (1.50 g., 3.83 mmole).

PMR: $\delta_{CDCl_3}^{TMS}$ 0.88 (m, sidechain terminal methyl), 1.29 (s, gem dimethyl), 2.0–3.0 (m, C-2, 4, 5 methylenes), 3.7 (m, benzylic methine), 5.90 (s, phenol), 6.82 (bs, overlaps δ6.92, ArH), 6.92 (dd, J=8 and 2 Hz, ArH) and 7.17 (d, J=8 Hz, ArH).
IR: (KBr) 3279, 1739, 1621 and 1577 cm$^{-1}$.
MS: m/e 302 (M+), 283, 217, 189, 175 and 161.
Analysis: Calc'd for C$_{20}$H$_{30}$O$_2$: C, 79.42; H, 10.00. Found: C, 79.65; H, 10.03.

3-[4-(1,1-Dimethylheptyl)-2-hydroxyphenyl]cycloheptanone (795 mg., 63%), m.p. 78°–79° C. (from pentane) from 3-[2-benzyloxy-4-(1,1-dimethylheptyl)phenyl]cycloheptanone (1.60 g., 3.80 mmole).

PMR: $\delta_{CDCl_3}^{TMS}$ 0.84 (m, terminal methyl), 1.25 (s, gem dimethyl), 6.80 (bs, overlaps 6.88, ArH), 6.88 (dd, J=8 and 2 Hz, ArH) and 7.10 (d, J=8 Hz, ArH).
IR: (CHCl$_3$) 3571, 3289, 1701, 1621, 1605 and 1577 cm$^{-1}$.
MS: m/e 330 (M+) and 245.
Analysis: Calc'd for C$_{22}$H$_{34}$O$_2$: C, 79.95; H, 10.37. Found: C, 79.60; H, 10.33.

Quantitative yield of 3-[2-hydroxy-4-(2-(5-phenylpentyloxy))phenyl]cyclohexanone as an oil from 3-[2-benzyloxy-4-(2-(5-phenylpentyloxy))phenyl]cyclohexanone (1.0 g., 2.26 mmol.).

PMR: $\delta_{CDCl_3}^{TMS}$ 1.28 (d, J=6 Hz, methyl), 2.7 (m, two methylenes), 3.12 (m, benzylic methine), 4.30 (m, sidechain methine), 6.32 (d, J=2 Hz, ArH), 6.32 (dd, J=8 and 2 Hz, ArH), 6.80 (d, J=8 Hz, ArH) and 7.18 (s, PhH).
IR: (CHCl$_3$) 3571, 3333, 1709, 1623 and 1587 cm$^{-1}$.
MS: m/e 352 (M+), 206, 188 and 91.

3-(2,4-Dihydroxyphenyl)cyclohexanone as a solid (8.5 g., 94%), m.p. =158° C. (from isopropyl ether) from 3-(2,4-dibenzyloxyphenyl)cyclohexanone (16.9 g., 43.7 mmol.).

PMR: $\delta_{D_6\text{-}DMSO}^{TMS}$ 1.3–3.5 (several m), 6.1–6.8 (several m, ArH and OH), and 6.93 (d, J=8 Hz, ArH).

IR: (KBr) 3195, 1631 and 1603 cm$^{-1}$.

MS: m/e 206 (M$^{30}$), 188, 163, 149 and 136.

Analysis: Cacl'd for $C_{12}H_{14}O_3$: C, 69.88; H, 6.84%. Found: C, 69.94; H, 6.78%.

3-[4-(1,1-dimethyloctyl)-2-hydroxyphenyl]cyclohexanone (0.75 g., 48%) from 2.00 g. (4.76 mmol.) of 3-[2-benzyloxy-4-(1,1-dimethyloctyl)phenyl]cyclohexanone.
M.P.: 78°–80° C. (from pentane).

PMR: $\delta_{CDCl_3}{}^{TMS}$ 0.83 (m, terminal sidechain methyl), 1.22 (s, gem dimethyl) and 6.85 (m, ArH).

IR: (CHCl$_3$) 3571, 3333, 1709(w), 1626 and 1577 cm$^{-1}$.

MS: m/e 330 (M$^+$), 314, 312, 287 and 231.

Analysis: Calc'd for $C_{22}H_{34}O_2$: C, 79.95; H, 10.37%. Found: C, 79.97; H, 9.99%.

3-(4-t-butyl-2-hydroxyphenyl)cyclohexanone (4.22 g., 58%) from 3-(2-benzyloxy-4-t-butylphenyl)cyclohexanone (10.0 g., 0.0298 mole).

M.P.: 177°–178° C. (from isopropyl ether).

PMR: $\delta_{DMSO-D_6}{}^{TMS}$ 1.25 (s, t-butyl), 6.7–6.9 (m, two ArH) and 7.02 (d, J=8 Hz, ArH).

IR: (KBr) 3279, 1639 and 1592 cm$^{-1}$.

MS: m/e 246 (M$^+$), 231, 228, 215, 213, 203, 189, 176 and 161.

3-[4-(1,1-dimethylpropyl)-2-hydroxyphenyl]cyclohexanone (2.52 g., 45%) from 3-[2-benzyloxy-4-(1,1-dimethylpropyl)phenyl]cyclohexanone (7.50 g., 0.0214 mole).

M.P.: 165°–166° C. (from isopropyl ether)

PMR: $\delta_{DMSO-D_6}{}^{TMS}$ 0.63 (t, J=7 Hz, terminal methyl), 1.11 (s, gem dimethyl), 6.8 (m, ArH, OH) and 7.10 (d, J=8 Hz, ArH).

IR: (CHCl$_3$) 3636, 3401, 1724(w), 1634 and 1587 cm$^{-1}$.

MS: m/e 260 (M$^+$), 242, 231, 217, 213 and 161.

Analysis: Calc'd for $C_{17}H_{24}O_2$: C, 78.42; H, 9.29% Found: C, 78.17; H, 9.22%.

3-[4-(1,1-dimethylbutyl)-2-hydroxyphenyl]cyclohexanone (0.6 g., 11%) from 3-[2-benzyloxy-4-(1,1-dimethylbutyl)phenyl]cyclohexanone (7.00g., 0.0192 mole).

M.P.: 101°–102° C. (from isopropyl ether)

PMR: $\delta_{CDCl_3}{}^{TMS}$ 0.82 (m, terminal methyl), 1.25 (s, gem dimethyl) and 6.80 (m, ArH).

IR: (CHCl$_3$) 3636, 3401, 1724(w), 1634 and 1585 cm$^{-1}$.

MS: m/e 274 (M$^{30}$), 256, 231 and 213.

Analysis: Calc'd for $C_{18}H_{26}O_2$: C, 78.79; H, 9.55%. Found: C, 78.78; H, 9.21%.

trans-3-[4-(1,1-Dimethylheptyl)-2-hydroxyphenyl]-4-propylcyclohexanone (1.0 g., 76%) as an oil from trans-3-[2-benzyloxy-4-(1,1-dimethylheptyl)phenyl]-4-(2-propenyl)cyclohexanone (1.65 g., 3.69 mmole).

IR: (CHCl$_3$) 3610, 3390, 1718(weak), 1629 and 1577 cm$^{-1}$.

MS: m/e 358 (M$^+$), 340, 288, 273, 255, 203 and 161.

PMR: $\delta_{CDCl_3}{}^{TMS}$ 0.9 (m, terminal methyls), 1.22 (s, gem dimethyls), 6.70 (dd, J=8 and 2 Hz, ArH), 6.75 (d, J=2 Hz, ArH) and 6.87 (d, J=8 Hz, ArH).

3-[4-(1,1-Dimethylpentyl)-2-hydroxyphenyl]cyclohexanone (4.0 g., 95%) from 3-[2-benzyloxy-4-(1,1-dimethylpentyl)phenyl]cyclohexanone (5.5 g., 0.0146 mole).

M.P.: 124.5°–125.5° C. (from pentane)

IR: (CHCl$_3$) 3623, 3378, 1718(weak), 1634 and 1587 cm$^{-1}$.

M,S: m/e 288(M$^+$), 245 and 231.

Analysis: Calc'd for $C_{19}H_{28}O_2$: C, 79.12; H, 9.79%. Found: C, 79.32; H, 9.53%.

3-[4-(1,1-Dimethylhexyl)-2-hydroxyphenyl]cyclohexanone (quantitative) from 3-[2-benzyloxy-4-(1,1-dimethylhexyl)phenyl]cyclohexanone (2.0 g., 5.1 mmole).

M.P.: 82°–83° C.

IR: (CHCl$_3$) 3636, 1634, 1616 and 1585 cm$^{-1}$.

MS: m/e 302 (M$^+$), 284, 259 and 231.

PMR: $\delta_{CDCl_3}{}^{TMS}$ 0.82 (s, terminal methyl), 1.23 (s, gem dimethyl), 3.10 (m,), 3.55 (m) and 6.83 (m, ArH).

Analysis: Calc'd for $C_{20}H_{30}O_2$: C, 79.42; H, 10.00%. Found: C, 79.16; H, 9.75%.

3-[4-(1,1-Dimethylnonyl)-2-hydroxyphenyl]cyclohexanone (2.4 g., 61%) from 3-[2-benzyloxy-4-(1,1-dimethylnonyl)phenyl]cyclohexanone (5.0 g., 11.5 mmole).

M.P.: 72°–73° C.

IR: (CHCl$_3$) 3650, 3413, 1721(weak), 1639 and 1595 cm$^{-1}$.

HRMS: m/e 344.2691, (M$^+$), $C_{23}H_{36}O_2$), 326.2570 and 301.2168.

PMR: $\delta_{CDCl_3}{}^{TMS}$ 0.87 (m, terminal methyl), 1.28 (s, gem dimethyl), 3.10 (m) and 6.85 (m, ArH).

3-[4-(1,1-Dimethyldecyl)-2-hydroxyphenyl]cyclohexanone (880 mg., 55%) from 3-[2-benzyloxy-3-(1,1-dimethyldecyl)phenyl]cyclohexanone (2.0 g., 4.46 mmole).

M.P.: 78°–79° C.

IR: (CHCl$_3$) 3623, 1629, 1616 and 1587 cm$^{-1}$.

HRMS: m/e 358.2836 (M$^+$, $C_{24}H_{38}O_2$).

PMR: $\delta_{CDCl_3}{}^{TMS}$ 0.88 (m, terminal methyl), 1.27 (s, gem dimethyl), 3.15 (m), and 6.85 (m, ArH).

3-[4-(1,1-Dimethylundecyl)-2-hydroxyphenyl]cyclohexanone (1.49 g., 46%) from 3-[2-benzyloxy-4-(1,1-dimethylundecyl)phenyl]cyclohexanone (4.00 g., 8.66 mmole).

M.P.: 72°–73°C.

IR: (KBr) 3268, 1629 and 1580 cm$^{-1}$.

MS: m/e 372(M$^+$), 354, 329 and 231.

PMR: $\delta_{CDCl_3}{}^{TMS}$ 0.87 (m, terminal methyl), 1.24 (s, gem dimethyl), 3.16 (m), 3.42 (m) and 6.88 (m, ArH).

Analysis: Calc'd for $C_{25}H_{40}C_2$: C, 80.59; H, 10.82%; Found: C, 80.70; H, 10.84%

3-[4-(1,1-Dimethylheptyl)-2-hydroxyphenyl]cyclooctanone (1.92 g., 81%) from 3-[2-benzyloxy-4-(1,1-dimethylheptyl)-phenyl]cyclooctanone (3.02 g., 6.95 mmole).

M.P.: 118° C.

IR: (CHCl$_3$) 3623, 3356, 1709, 1629 and 1587 cm$^{-1}$.

MS: m/e 344 (M$^+$), 329, 326, 283, 273, 259 and 241.

PMR: $\delta_{CDCl_3}{}^{TMS}$ 0.82 (m, terminal methyl), 1.27 (s, gem dimethyl), 3.55 (bm, benzylic methine), 6.76 (d, J=2 Hz, ArH), 6.78 (dd, J=8 and 2 Hz, ArH) and 7.02 (d, J=8 Hz, ArH).

Analysis: Calc'd for $C_{23}H_{36}O_2$: C, 80.18; H, 10.53% Found: C, 79.92; H, 10.37%.

3-[4-(1,1-Dimethylheptyl)-2-hydroxyphenyl]-4-methyl-2-cyclohexen-1-one (1.15 g., 70%) from 3-[2-benzyloxy-4-(1,1-dimethylheptyl)phenyl]-4-methyl-2-cyclohexen-1-one (2.10 g., 5.02 mmole).

M.P.: 111° C. (fom diisopropyl ether-petroleum ether).

IR: (CHCl$_3$) 3534, 3279, 1667, 1623 and 1567 cm$^{-1}$.

MS: m/e 328 (M$^+$), 313 and 243.

PMR: $\delta_{CDCL_3}{}^{TMS}$ 0.83 (m, terminal methyl), 1.10 (d, J=7 Hz, methyl, 1.25 (s, gem dimethyl), 2.6 (m, methylene), 3.2 (m, methine), 6.32 (bs, vinyl H) 6.63 (s, OH), 6.9 (m, ArH) and 7.08 (d, J=8 Hz, ArH).

Analysis: Calc'd for $C_{22}H_{32}O_2$: C, 80.44; H, 9.83%
Found: C, 80.35; H, 9.67%.

EXAMPLE 3 cis-3-[2-Benzyloxy-4-(1,1-dimethylheptyl)- phenyl]-cyclohexanol and the trans isomer To a −40° C. solution of 43.0 g. (0.106 mol) of 3-[2-benzyloxy-4-(1,1-dimethylheptyl)phenyl]cyclohexanone in 500 ml. of methanol and 15 ml. of tetrahydrofuran was added, in three portions, 8.05 g. (0.212 mol.) of sodium borohydride. The reaction mixture was stirred for one hour at −40° C., allowed to warm to −10° C. and was then quenched by the addition of 100 ml. of saturated sodium chloride. The quenched reaction was added to 1500 ml. of water and extracted with three 450 ml. portions of ether. The combined ether extract was washed with three 100 ml. portions of water and two 200 ml. portions of saturated sodium chloride, dried over magnesium sulfate and evaporated to an oil. The oil was purified via column chromatography on 400 g. of silica gel eluted with 20% ether-cyclohexane to yield, in order of elution, 5.0 g. (12%) of trans-3-[2-benzyloxy-4-(1,1-dimethylheptyl)-phenyl]cyclohexanol.

PMR: $\delta_{CDCL_3}^{TMS}$ 0.85 (m, terminal methyl), 1.26(s, gem dimethyl), 3.51 (m, benzylic methine), 4.24 (m, carbinol methine), 5.15 (s, benzylic methylene), 6.85-7.26 (m, ArH) and 7.47 (m, PhH).

IR: ($CHCl_3$) 3636, 3497, 1629 and 1587 $cm^{-1}$.

MS: m/e 408 ($M^+$), 393, 390, 323 and 91.

Analysis: Calc'd for $C_{28}H_{40}O_2$: C, 82,30; H, 9.87%
Found: C, 81.98; H, 9.82%.

22.2 g. (51%) of cis-3-[2-benzyloxy-4-(1,1-dimethylheptyl)phenyl]cyclohexanol.

PMR: $\delta_{CDCl_3}^{TMS}$ 0.85 (m, terminal methyl), 1.28 (s, gem dimethyl), 3.1 (m, benzylic methine), 3.79 (m, carbinol methine), 5.12 (s, benzylic methylene), 6.83-7.22 (m, ArH) and 7.42 (s, PhH).

M.P.: 75.5°-76.5° C.

IR: ($CHCl_3$) 3636, 3497, 1629 and 1587 $cm^{-1}$.

MS: m/e 408 ($M^+$), 393, 390, 323 and 91.

Analysis: Calc'd for $C_{28}H_{40}O_2$: C, 82,30; H, 9.87%
Found: C 81.95; H, 9.74%

The following compounds were similarly prepared from appropriate ketones of Example 1.

A quantitative yield of Z-b 3-[2-benzyloxy-4-(1,1-dimethylheptyl)phenyl]-3-methylcyclohexanol as an oil from 3-[2-benzyloxy-4-(1,1-dimethylheptyl)phenyl]-3-methylcyclohexanone (200 mg., 0.476 mmole).

PMR: $\delta_{CDCl_3}^{TMS}$ 0.81 (m, terminal sidechain methyl), 1.23 (s, gem dimethyl), 1.30 (s, C-3 methyl), 3.65 (m, carbinol methine), 5.00 (s, benzyl ether methylene), 6.6-7.3 (m, ArH) and 7.25 (m, PhH).

IR: ($CHCl_3$) 3546, 3378, 1603 and 1555 $cm^{-1}$.

MS: m/e 422 ($M^+$), 337, 314, 299, 271 and 229.

trans, trans-3[2benzyloxy-4-(1,1-dimethylheptyl) phenyl]-b 4-methylcyclohexanol (0.225 g., 14%) as an oil, and 1.19 g. (74%) of the cis, trans-isomer from trans-3-[2-benzyloxy-4-(1,1-dimethylheptyl)phenyl]-4-methylcyclohexanone (1.6 g., 3.8 mmoles).

trans,trans:

PMR: $\delta_{CDCl_3}^{TMS}$ 0.80 (m, terminal sidechain methyl and C-4 methyl), 1.27 (s, gem dimethyl), 3.12 (m, benzylic methine), 4.20 (m, carbinol methine), 5.13 (s, benzyl ether methylene), 6.95 (m, ArH), 7.15 (d, J=8 Hz, ArH) and 7.48 (bs, PhH).

IR: ($CHCl_3$) 3413, 1616 and 1575 $cm^{-1}$.

MS: m/e 422 ($M^+$), 407, 337, 314, 272, 229 and 91.

cis,trans:

PMR: $\delta_{CDCl_3}^{TMS}$ 0.70 (d, J=6 Hz, C-4 methyl), 0.85 (m, terminal sidechain methyl), 1.29 (s, gem dimethyl), 2.81 (m, benzylic methine), 3.75 (m, carbinol methine), 5.13 (s, benzyl ether methylene), 6.93 (m, ArH), 7.15 (d, J=8 Hz, ArH) and 7.43 (bs, PhH).

IR: ($CHCl_3$) 3571, 3390, 1618 and 1577 $cm^{-1}$.

MS: m/e 422 ($M^+$), 337, 314, 272, 229 and 91.

A mixture of cis and trans 3-[2-benzyloxy-4-(1,1-dimethylheptyl)phenyl]cyclopentanol (1.1 g., 85%) as an oil from 3-[2-benzyloxy-4-(1,1-dimethylheptyl)-phenyl]cyclopentanone (1.32 g., 3.37 mmoles).

MS: m/e 394 ($M^+$), 379, 376, 309 and 91.

trans-3-[2-Benzyloxy-4-(1,1-dimethylheptyl)phenyl]-cycloheptanol (695 mg., 49%) and 380 mg. (27%) of the cis isomer as oils from 3-[2-benzyloxy-4-(1,1-dimethylheptyl)phenyl]cycloheptanone (1.40 g., 3.33 mmole).

Cis:

PMR: $\delta_{CDCl_3}^{TMS}$ 0.85 (m, sidechain terminal methyl), 1.30 (s, gem dimethyl), 3.15 (m, benzylic methine), 3.90 (m, carbinol methine), 5.15 (s, benzyl ether methylene), 6.8-7.4 (m, ArH) and 7.45 (bs, PhH).

IR: ($CHCl_3$) 3571, 3448, 1613 and 1572 $cm^{-1}$.

MS: m/e 422 ($M^+$), 337, 314, 229 and 91.

Trans:

PMR: $\delta_{CDCl_3}^{TMS}$ 0.86 (m, terminal methyl), 1.26 (s, gem dimethyl), 3.41 (m, benzylic methine), 4.10 (m, carbinol methine), 5.17 (s, benzylic methylene), 6.8-7.2 (m, ArH), 7.18 (d, J=8 Hz, ArH), and 7.45 (bs, PhH).

IR: ($CHCl_3$) 3534, 3390, 1613 and 1572 $cm^{-1}$.

MS: m/e 422 ($M^+$), 337, 331, 314, 246, 229 and 91.

cis-3-[2-benzyloxy-4-(2-5-phenylpentyloxy)phenyl]-cyclohexanol (1.51 g., 76%) and the transisomer (0.379 g., 19%) as oils from 3-[2-Benzyloxy-4-(2-(5-phenylpentyloxy))phenyl]cyclohexanone (2.0 g., 4.52 mmoles).

trans:

PMR: $\delta_{CDCl_3}^{TMS}$ 1.28 (d, J=6 Hz, methyl), 2.68 (m, benzylic methylene), 3.45 (m, benzylic methine), 4.22 (m, carbinol methine), 4.30 (m, sidechain methine), 5.09 (s, benzyl ether methylene), 6.45 (dd, J=8 and 2 Hz, ArH), 6.55 (bs, ArH), 7.10 (d, J=8 Hz, ArH), 7.25 (s, PhH) and 7.45 (bs, PhH).

IR: ($CHCl_3$) 3571, 3448, 1613 and 1590 $cm^{-1}$.

MS: m/e 444 ($M^+$), 298, 280, 190 and 91.

cis:

PMR: $\delta_{CDCl_3}^{TMS}$ 1.25 (d, J=6 Hz, methyl), 3.0 (m, benzylic methine), 3.77 (m, carbinol methine), 4.38 (m, sidechain methine), 5.10 (s, benzyl ether methine), 6.50 (dd, J=8 and 2 Hz, ArH), 6.58 (bs, ArH), 7.12 (d, J=8 Hz, ArH), 7.32 (s, PhH) and 7.43 (s, PhH).

IR: ($CHCl_3$) 3571, 3390, 1613 and 1587 $cm^{-1}$.

MS: m/e 444 ($M^+$), 298, 190 and 91.

cis-3-[2-Benzyloxy-4-(1,1-dimethyloctyl)phenyl]cyclohexanol (1.35 g., 45%) and the trans-isomer (0.34 g., 11%) from 3.00 g. (7.14 mmol.) of 3-[2-benzyloxy-4-(1,1-dimethyloctyl)phenyl]cyclohexanone and 0.90 g. (30%) of a cis-trans mixture.

trans:

PMR: $\delta_{CDCl_3}^{TMS}$ 0.87 (m, terminal sidechain methyl), 1.25 (s, gem dimethyl), 3.50 (m, benzylic methine), 4.22 (m, carbinol methine), 5.15 (s, benzyl ether methylene) and 6.8-7.6 (m, ArH and PhH).

IR: ($CHCl_3$) 3497, 1623 and 1582 $cm^{-1}$.

MS: m/e 422 ($M^+$) and 323.

cis.

PMR: $\delta_{CDCl_3}^{TMS}$ 0.85 (m, terminal sidechain methyl), 1.25 (s, gem dimethyl), 3.10 (m, benzylic methine), 3.75 (m, carbinol methine), 5.12 (s, benzyl ether methylene)

6.91 (dd, J=8 and 2 Hz, ArH), 6.91 (d, J=2 Hz, ArH), 7.17 (d, J=8 Hz, ArH) and 7.42 (bs, PhH).

IR: (CHCl$_3$) 3571, 3425, 1618 and 1577 cm$^{-1}$.

MS: m/e 422 (M+) and 323.

cis-3-(2-Benzyloxy-4-t-butylphenyl)cyclohexanol (7.18 g., 59%) and the trans-isomer (1.33 g., 11%), and 1.5 g. (12%) of a mixture of cis and trans-isomers from 12.0 g. (0.0357 mole) of 3-(2-benzyloxy-4-t-butylphenyl)cyclohexanone.

cis:

M.P.: 78°–79° C. (from hexane)

PMR: $\delta_{CDCl_3}^{TMS}$ 1.30 (s, t-butyl), 3.10 (m, benzylic methine), 3.72 (m, carbinol methine), 5.12 (s, benzyl ether methylene), 6.97 (d, J=2 Hz, ArH), 6.97 (dd, J=8 and 2 Hz, ArH), 7.17 (d, J=8 Hz, ArH) and 7.40 (bs, PhH).

IR: (CHCl$_3$) 3636, 3472, 1621 and 1582 cm$^{-1}$.

MS: m/e 338 (M+), 323, 320, 230, 215 and 91.

Analysis: Calc'd for C$_{23}$H$_{30}$O$_2$: C, 81.61; H, 8.93% Found: C, 81.79; H, 8.77% trans:

PMR: $\delta_{CDCl_3}^{TMS}$ 1.23 (s, t-butyl), 3.50 (m, benzylic methine), 4.20 (m, carbinol methine), 5.02 (s, benzyl ether methylene) and 6.8–7.4 (m, ArH and PhH).

IR: (CHCl$_3$) 3650, 3472, 1626 and 1587 cm$^{-1}$.

MS: m/e 338 (M+), 323, 320, 230 and 91.

cis-3-[2-Benzyloxy-4-(1,1-dimethylpropyl)phenyl]cyclohexanol (6.3 g., 78%) and the trans-isomer (1.0 g., 12%) as oils from 8.0 g. (0.0229 mole) of 3-[2-benzyloxy-4-(1,1-dimethylpropyl)phenyl]cyclohexanone.

cis:

PMR: $\delta_{CDCl_3}^{TMS}$ 0.67 (t, J=7 Hz, terminal methyl), 1.26 (s, gem dimethyl), 3.05 (m, benzylic methine), 3.75 (m, carbinol methine), 5.15 (s, benzyl ether methylene), 6.92 (d, J=2, ArH), 6.92 (dd, J=8 and 2 Hz, ArH), 7.17 (d, J=8 Hz, ArH) and 7.42 (bs, PhH).

IR: (CHCl$_3$) 3636, 3344, 1626 and 1587 cm$^{-1}$.

MS: m/e 352 (M+), 337, 334, 323, 244, 215 and 91.

trans:

IR: (CHCl$_3$) 3636, 1626 and 1587 cm$^{-1}$.

MS: m/e 352 (M+), 337, 334, 323, 244, 215 and 91.

cis-3-[2-Benzyloxy-4-(1,1-dimethylbutyl)phenyl]cyclohexanol (4.16 g., 52%) and the trans-isomer (0.88 g., 11%), and 0.49 g. (6.1%) of a mixture of cis and trans-isomers as oils from 8.0 g. (0.022 mole) of 3-[2-benzyloxy-4-(1,1-dimethylbutyl)phenyl]cyclohexanone.

cis:

PMR: $\delta_{CDCl_3}^{TMS}$ 0.80 (m, terminal methyl), 1.23 (s, gem dimethyl), 3.05 (m, benzylic methine), 3.70 (m, carbinol methine), 5.08 (s, benzyl ether methylene), 6.86 (d, J=2 Hz, ArH), 6.86 (dd, J=8 and 2 Hz, ArH), 7.11 (d, J=8 Hz, ArH) and 7.35 (bs, PhH).

IR: (CHCl$_3$) 3623, 3448, 1621 and 1582 cm$^{-1}$.

MS: m/e 366 (M+), 351, 348, 323, 258, 215 and 91.

trans:

PMR: $\delta_{CDCl_3}^{TMS}$ 0.83 (m, terminal methyl), 1.22 (s, gem dimethyl), 3.40 (m, benzylic methine), 4.18 (m, carbinol methine), 5.09 (s, benzyl ether methylene), 6.86 (d, J=2 Hz, ArH), 6.86 (dd, J=8 and 2 Hz, ArH), 7.11 (d, J=8 Hz, ArH) and 7.39 (m, PhH).

IR: (CHCl$_3$) 3623, 3472, 1623 and 1585 cm$^{-1}$.

MS: m/e 366 (M+), 351, 348, 323, 258, 215 and 91.

trans-3-[2-Benzyloxy-4-(1,1-dimethylheptyl)phenyl]-cis-4-(2-propenyl)cyclohexanol (1.9 g., 13%) and the cis-3,trans-4 isomer (7.3 g., 51%) as oils from trans-3-[2-benzyloxy-4-(1,1-dimethylheptyl)phenyl]-4-(2-propenyl)cyclohexanone (14.3 g., 32.1 mmole). The order of elution from silica gel with 2:1 pentane:ether was the trans-3, cis-4 isomer of the title compound as an oil followed by the cis-3, trans-4 isomer.

trans-3,cis-4 isomer:

IR: (CHCl$_3$) 3559, 3401, 1639, 1608 and 1567 cm$^{-1}$.

MS: m/e 448 (M+), 433, 430, 363, 406 and 91.

PMR: $\delta_{CDCl_3}^{TMS}$ 0.82 (m, terminal methyl), 1.25 (s, gem dimethyl), 3.30 (m, benzylic methine), 4.12 (m, carbinol methine), 4.6–5.0 (m, vinyl H), 5.06 (s, benzylic methylene), 5.2–6.1 (m, vinyl H), 6.82 (d, J=2 Hz, ArH), 6.82 (dd, J=8 and 2 Hz, ArH), 7.07 (d, J=8 Hz, ArH) and 7.38 (bs, Ph).

cis-3,trans-4 isomer:

IR: (CHCl$_3$) 3571, 3401, 1639, 1610 and 1572 cm$^{-1}$.

MS: m/e 448 (M+), 406, 363 and 91.

PMR: $\delta_{CDCl_3}^{TMS}$ 0.82 (m, terminal methyl), 1.22 (s, gem dimethyl), 2.90 (m, benzylic methine), 3.73 (m, carbinol methine), 4.6–5.1 (m, vinyl H), 5.02 (s, benzylic methylene), 5.3–6.3 (m, vinyl H), 6.75 (d, J=2 Hz, ArH), 6.75 (dd, J=8 and 2 Hz, ArH), 6.99 (d, J=8 Hz, ArH) and 7.25 (bs, Ph).

cis-3-[2-Benzyloxy-4-(1,1-dimethylheptyl)phenyl]-trans-4-(2-butenyl)cyclohexanol (495 mg., 82%) and the trans-3,cis-4 isomer (105 mg., 18%, from trans-3-[2-benzyloxy-4-(1,1-dimethylheptyl)phenyl]-(2-butenyl)cyclohexanone (600 mg., 1.30 mmole). The trans-3,cis-4 isomer was eluted first.

trans-3,cis-4 isomer:

MS: m/e 462 (M+), 447, 444, 377 and 91.

cis-3,trans-4 isomer:

IR: (CHCl$_3$) 3610, 3448, 1618 and 1577 cm$^{-1}$.

MS: m/e 462 (M+), 447, 444, 377 and 91.

cis-3-[2-Benzyloxy-4-(1,1-dimethylheptyl)phenyl]-trans-4-(2-pentenyl)cyclohexanol and the trans-3,cis-4 isomer from trans-3-(2-benzyloxy-4-(1,1-dimethylheptyl)phenyl)-4-(2-pentenyl)cyclohexanone (497 mg., 1.04 mmole). In order of elution was obtained 84 mg. (17%) of the trans-3,cis-4 isomer (RF=0.26, silica gel, 33% ether-pentane) and 363 mg. (73%) of the cis-3,trans-4 isomer (Rf=0.13, silica gel, 33% ether-pentane).

cis-3-[2-Benzyloxy-4-(1,1-dimethylpentyl)phenyl]cyclohexanol (5.0 g., 83%) and the trans-isomer (0.60 g., 10%) as oils from 3-[2-benzyloxy-4-(1,1-dimethylpentyl)phenyl]cyclohexanone (6.0 g., 58 mmole).

trans:

IR: (CHCl$_3$) 3636, 3497, 1623 and 1582 cm$^{-1}$.

MS: m/e 380 (M+).

PMR: $\delta_{CDCl_3}^{TMS}$ 0.83 (m, terminal methyl), 1.24 (s, gem dimethyl), 3.5 (m, benzylic methine), 4.20 (m, carbinol methine), 5.09 (s, benzylic methylene) and 6.8–7.6 (m, ArH).

cis:

IR: (CHCl$_3$) 3636, 1621 and 1580 cm$^{-1}$.

MS: m/e 380 (M+).

PMR: $\delta_{CDCl_3}^{TMS}$ 0.75 (m, terminal methyl), 1.14 (s, gem dimethyl), 2.90 (m, benzylic methine), 3.52 (m, carbinol methine), 4.80 (s, benzylic methylene), 6.49 (dd, J=8 and 2 Hz, ArH), 6.49 (d, J=2 Hz, ArH), 6.72 (d, J=8 Hz, ArH) and 6.96 (bs, Ph).

cis-3-[2-Benzyloxy-4-(1,1-dimethylhexyl)phenyl]cyclohexanol (3.0 g., 43%) and the trans-isomer (660 mg., 9%) as oils from 3-[2-benzyloxy-4-(1,1-dimethylhexyl)phenyl]cyclohexanone (7.0 g., 17.9 mmole).

cis:

IR: (CHCl$_3$) 3623, 3448, 1618 and 1575 cm$^{-1}$.

MS: m/e 394 (M+).

PMR: $\delta_{CDCl_3}^{TMS}$ 0.82 (m, terminal methyl), 1.22 (s, gem dimethyl), 3.07 (m, benzylic methine), 3.0 (m, carbinol methine), 5.08 (s, benzylic methylene), 6.88 (dd, J=8 and 2 Hz, ArH), 6.88 (d, J=2 Hz, ArH), 7.12 (d, J=8 Hz, ArH) and 7.37 (bs, Ph).

trans:

IR: (CHCl$_3$) 3623, 7448, 1618 and 1577 cm$^{-1}$.

MS: m/e 394 (M+).

PMR: $\delta_{CDCl_3}^{TMS}$ 0.80 (m, terminal methyl), 1.27 (s, gem dimethyl), 3.42 (m, benzylic methine), 4.12 (m, carbinol methine), 5.02 (s, benzylic methylene), 6.83 (m, ArH), 7.04 (d, J=8 Hz, ArH) and 7.34 (bs, ArH).

cis-3-[2-Benzyloxy-4-(1,1-dimethylnonyl)phenyl]cyclohexanol (5.0 g., 59%) and the trans-isomer (1.0 g., 12%) as oils from 3-[2-benzyloxy-4-(1,1-dimethylnonyl)phenyl]cyclohexanone (8.5 g., 19.6 mmole).

cis:

IR: (CHCl$_3$) 3623, 3448, 1618 and 1577 cm$^{-1}$.

MS: m/e 436 (M+).

PMR: $\delta_{CDCl_3}^{TMS}$ 0.83 (m, terminal methyl), 1.22 (s, gem dimethyl), 3.04 (m, benzylic methine), 3.67 (m, carbinol methine), 5.08 (s, benzylic methylene), 6.87 (dd, J=8 and 2 Hz, ArH), 6.87 (d, J=2 Hz, ArH) and 7.05-7.45 (m, ArH and Ph).

trans:

IR: (CHCl$_3$) 3610, 3448, 1618 and 1575 cm$^{-1}$.

MS: m/e 436 (M+)

PMR: $\delta_{CDCl_3}^{TMS}$ 0.82 (m, terminal methyl), 1.22 (s, gem dimethyl), 3.42 (m, benzylic methine), 4.16 (m, carbinol methine), 5.02 (s, benzylic methylene) and 6.7-7.5 (m, ArH and Ph).

cis-3-[2-Benzyloxy-4-(1,1-dimethylundecyl)phenyl]cyclohexanol (3.5 g., 50%) and the trans-isomer (1.0 g., 14%) as oils from 3-[2-benzyloxy-4-(1,1-dimethylundecyl)phenyl]cyclohexanone (7.00 g., 15.0 mmole).

cis:

IR: (CHCl$_3$) 3636, 3448, 1621 and 1582 cm$^{-1}$.

MS: m/e 464 (M+).

PMR: $\delta_{CDCl_3}^{TMS}$ 0.95 (m, terminal methyl), 1.33 (s, gem dimethyl), 3.09 (m, benzylic methine), 3.70 (m, carbinol methine), 5.20 (s, benzylic methylene), 6.99 (dd, J=8 and 2 Hz, ArH), 6.99 (dd, J=8 and 2 Hz, ArH), 7.22 (d, J=8 Hz, ArH) and 7.50 (bs, PhH).

trans:

IR: (CHCl$_3$) 3534(broad), 1618 and 1577 cm$^{-1}$.

MS: m/e 464 (M+).

PMR: $\delta_{DCDl_3}^{TMS}$ 0.85 (m, terminal methyl), 1.22 (s, gem dimethyl), 3.48 (m, benzylic methine), 4.17 (m, benzylic methine), 5.08 (s, benzylic methylene) and 6.75-7.55 (m, ArH and Ph).

cis-3-[2-Benzyloxy-4-(1,1-dimethyldecyl)phenyl]cyclohexanol (2.66 g., 59%) and the trans-isomer (0.36 g., 8%) as oils from 3-[2-benzyloxy-4-(1,1-dimethyldecyl)phenyl]cyclohexanone (4.5 g., 10.0 mmole).

cis:

IR: (CHCl$_3$) 3704, 3571, 1639 and 1597 cm$^{-1}$.

MS: m/e 450 (M+).

PMR: $\delta_{CDCl_3}^{TMS}$ 0.86 (m, terminal methyl), 1.25 (s, gem dimthyl), 3.08 (m, benzylic methine), 3.74 (m, carbinol methine), 5.08 (s, benzylic methylene), 6.88 (dd, J=8 and 2 Hz, ArH), 6.88 (d, J=2 Hz, ArH), 7.12 (d, J=8 Hz, ArH) and 7.37 (bs, Ph).

trans:

IR: (CHCl$_3$) 3623, 3448, 1616 and 1577 cm$^{-1}$.

MS: m/e 450 (M+).

PMR: $\delta_{CDCl_3}^{TMS}$ 0.82 (m, terminal methyl), 1.22 (s, gem dimethyl), 3.53 (m, benzylic methine), 4.22 (m, carbinol methine), 5.02 (s, benzylic methylene) and 6.8-7.6 (m, ArH and Ph).

cis-3-[2-Benzyloxy-4-(1,1-dimethylheptyl)phenyl]clooctanol (1.36 g., 19%) and the trans-isomer (4.12 g., 59%) as oils from 3-[2-benzyloxy-4-(1,1-dimethylheptyl)phenyl]cyclooctanone (7.0 g., 16.1 mmole).

MS: m/e 436 (M+), 421, 418, 351, 328, 300, 243 and 91.

PMR: $\delta_{CDCl_3}^{TMS}$ 0.83 (m, terminal methyl), 1.28 (s, gem dimethyl), 3.19 (bm, benzylic methine), 3.89 (bm, carbinol methine), 5.10 (s, benzylic methylene), 6.83 (m, ArH), 7.08 (d, J=8 Hz, ArH) and 7.38 (m, Ph).

trans:

MS: m/e 436 (M+), 421, 418, 351, 328, 243 and 91.

PMR: $\delta_{CDCl_3}^{TMS}$ 0.83 (m, terminal methyl), 1.28 (s, gem dimethyl), 3.4 (bm, benzylic methine), 3.9 (m, carbinol methine, 5.10 (s, benzylic methylene), 6.85 (m, ArH), 7.08 (d, J=8 Hz, ArH) and 7.36 (m, Ph).

EXAMPLE 4 cis-3-[4-(1,1-dimethylheptyl)-2-hydroxyphenyl]cyclohexanol

A mixture of 22.0 g. (0.0539 mol.) of cis-3-[2-benzyloxy-4-(1,1-dimethylheptyl)phenyl]cyclohexanol, 12.0 g. of sodium bicarbonate and 2.0 g. of 10% palladium on carbon was stirred under one atmosphere of hydrogen for 2 hours. The reaction mixture was filtered through diatomaceous earth with ethyl acetate and the filtrate evaporated to a solid. The solid was recrystallized from hexane to yield 13.2 g. (77%) of the title product, m.p. 109°-110° C.

PMR: $\delta_{CDCl_3}^{TMS}$ 0.81 (m, terminal methyl), 1.25 (s, gem dimethyl), 2.80 (bm, benzylic methine), 3.80 (bm, carbinol methine), 5.4 (broad, OH), 6.63 (bs, ArH), 6.77 (dd, J=8 and 2 Hz) and 6.87 (d, J=8 Hz, ArH).

IR: (CHCl$_3$) 3610, 3356, 1626 and 1582 cm$^{-1}$.

MS: m/e 318 (M+), 300 233 and 215.

Analysis: Calc'd for $C_{21}H_{34}O_2$: C, 79.19; H, 10.76. Found: C, 78.96; H, 10.59.

Following the above procedure, the compounds listed below were prepared from appropriate reactants of Example 3.

trans-3-[4-(1,1-Dimethylheptyl)-2-hydroxyphenyl]cyclohexanol (2.47 g., 71%), m.p. 124°-125° C. (from pentane) from trans-3-[2-benzyloxy-4-(1,1-dimethylheptyl)phenyl]cyclohexanol (4.50 g., 0.011 mol.).

PMR: $\delta_{CDCl_3}^{TMS}$ 0.81 (m, terminal methyl), 1.25 (s, gem dimethyl), 3.25 (m, benzylic methine), 4.22 (m, carbinol methine), 6.81 (d, J=2 Hz, ArH); 6.81 (dd, J=8 and 2 Hz), and 7.08 (d, J=8 Hz, ArH).

IR: (CHCl$_3$) 3610, 3390, 1626 and 1575 cm$^{-1}$. MS

MS: m/e 318 (M+), 300, 233 and 215.

Analysis: Calc'd for $C_{21}H_{34}O_2$; C, 79.19; H, 10.76. Found: C, 78.82; H, 10.43.

A quantitative yield of Z-3-[4-(1,1-dimethylheptyl)-2-hydroxyphenyl]-3-methylcyclohexanol, m.p. 90°-91° C. (recrystallized from petroleum ether) from Z-3-[2-benzyloxy-4-(1,1-dimethylheptyl)phenyl]-3-methylcyclohexanol (180 mg., 0.246 mmole).

PMR: $\delta_{CDCl_3}^{TMS}$ 0.85 (m, terminal sidechain methyl), 1.25 (s, gem dimethyl), 1.33 (s, C-3 methyl), 3.65 (m, carbinol methine), 5.48 (bs, OH), 6.63 (d, J=2 Hz. ArH), 6.82 (dd, J=8 and 2 Hz, ArH), and 7.19 (d, J=8 Hz, ArH).

IR: (CHCl$_3$) 3597, 3333, 1605 and 1570 cm$^{-1}$.

MS: m/e 332 (M+), 314, 299, 286, 271, 247 and 229.

Analysis: Calc'd for $C_{22}H_{36}O_2$: C, 79.45; H, 10.92. Found: C, 79.24; H, 10.64.

A quantitative yield of trans,trans-3-[4-(1,1-dimethylheptyl)-2-hydroxyphenyl]-4-methylcyclohexanol, m.p. 134°-135° C. (from pentane) from trans,trans-3-[2-benzyloxy-4-(1,1-dimethylheptyl)phenyl]-4-methylcyclohexanol (190 mg., 0.450 mmole).

PMR: $\delta_{CDCl_3}{}^{TMS}$ 0.7–0.9 (m, C-4 and terminal sidechain methyls), 1.24 (s, gem dimethyl), 3.00 (m, benzylic methine), 4.22 (m, carbinol methine), 6.78 (d, J=2 Hz, ArH), 6.88 (dd, J=8 and 2 Hz, ArH) and 7.02 (d, J=8 Hz, ArH).

IR: (CHCl₃) 3571, 3333, 1626 and 1575 cm⁻¹.

MS: m/e 332 (M+), 317, 314, 247, 233 and 229.

Analysis: Calc'd for $C_{22}H_{36}O_2$: C, 79.46; H, 10.92% Found: C, 79.13; H, 10.68%.

A quantitative yield of cis,trans-3-[4-(1,1-dimethylheptyl)-2-hydroxyphenyl]-4-methylcyclohexanol, m.p. 150°–151° C. (from pentane) from cis,trans-3-[2-benzyloxy-4-(1,1-dimethylheptyl)phenyl]-4-methylcyclohexanol (1.15 g., 2.72 mmoles).

PMR: $\delta_{CDCl_3}{}^{TMS}$ 0.72 (d, J=6 Hz, C-4 methyl), 0.86 (m, terminal sidechain methyl), 1.24 (s, gem dimethyl), 2.62 (m, benzylic methine), 3.77 (m, carbinol methine), 6.70 (d, J=2 Hz, ArH), 6.83 (dd, J=8 and 2 Hz, ArH) and 7.04 (d, J=8 Hz, ArH).

IR: (CHCl₃) 3571, 3333, 1621, 1605 and 1580 cm⁻¹.

MS: m/e 332 (M+), 314, 272, 247, 233 and 229.

Analysis: Calc'd for $C_{22}H_{36}O_2$: C, 79.46; H, 10.92. Found: C, 79.15; H, 10.72.

cis-3-[4-(1,1-Dimethylheptyl)-2-hydroxyphenyl]cyclopentanol (464 mg., 55%) and 228 mg. (27%) of the trans-isomer as oils from a mixture of cis and trans-3-[2-benzyloxy-4-(1,1-dimethylheptyl)phenyl]cyclopentanol (1.10 g., 2.79 mmoles).

cis:

PMR: $\delta_{CDCl_3}{}^{TMS}$ 0.83 (m, sidechain terminal methyl), 1.24 (s, gem dimethyl), 3.2 (m, benzylic methine), 4.52 (m, carbinol methine), 6.75 (dd, J=8 and 2 Hz, ArH), 6.81 (bs, overlaps δ6.75, ArH) and 6.97 (d, J=8 Hz, ArH).

IR: (CHCl₃) 3571, 3300, 1623 and 1567 cm⁻¹.

MS: m/e 304 (M+), 286, 219, 201 and 159.

trans:

PMR: $\delta_{CDCl_3}{}^{TMS}$ 0.83 (m, sidechain terminal methyl), 1.27 (s, gem dimethyl), 3.60 (m, benzylic methine), 4.55 (m, carbinol methine), 6.78 (bs, overlaps δ6.88, ArH), 6.88 (dd, J=8 and 2 Hz, ArH) and 7.10 (d, J=8 Hz, ArH).

IR: (CHCl₃) 3571, 3333, 1621 and 1575 cm⁻¹.

MS: m/e 304 (M+), 286, 219 and 201.

A quantitative yield of trans-3-[4-(1,1-dimethylheptyl)-2-hydroxyphenyl]cycloheptanol, m.p. 55°–57° C. from trans-3-[2-benzyloxy-4-(1,1-dimethylheptyl)phenyl]cycloheptanol (695 mg., 1.64 mmole).

PMR: $\delta_{CDCl_3}{}^{TMS}$ 0.88 (m, terminal methyl), 1.22 (s, gem dimethyl), 3.20 (m, benzylic methine), 4.22 (m, carbinol methine), 6.85 (dd, J=8 and 2 Hz, ArH), 6.90 (bs, overlaps δ6.85, ArH) and 7.13 (d, J=8 Hz, ArH).

IR: (CHCl₃) 3333, 1621, and 1570 cm⁻¹.

MS: m/e 332 (M+), 314, 247 and 229.

Analysis: Calc'd for $C_{22}H_{36}O_2$: C, 79.46; H, 10.92. Found: C, 79.68; H, 10.62.

A quantitative yield of cis-3-[4-(1,1-dimethylheptyl)2-hydroxyphenyl]cycloheptanol, m.p. 103°–104° C. (recrystallized from pentane) from cis-3-[2-benzyloxy-4-(1,1-dimethylheptyl)phenyl]cycloheptanol (380 mg., 0.900 mmole).

PMR: $\delta_{CDCl_3}{}^{TMS}$ 0.82 (m, terminal methyl), 1.20 (s, gem dimethyl), 3.0 (m, benzylic methine), 4.0 (m, carbinol methine), 6.72 (bs. overlaps δ6.81, ArH), 6.81 (dd, J=8 and 2 Hz, ArH) and 7.08 (d, J=8 Hz, ArH).

IR: (CHCl₃) 3571, 3311, 1621, 1605 and 1580 cm⁻¹.

MS: m/e 332 (M+), 314, 247 and 229.

Analysis: Calc'd for $C_{22}H_{36}O_2$: C, 79.46; H, 10.92. Found: C, 79.39; H, 10.72.

A quantitative yield of cis-3-[2-hydroxy-4-(2-(5-phenylpentyloxy)phenyl]cyclohexanol, m.p. 80°–84° C. (pentane) from cis-3-[2-benzyloxy-4-(2-(5-phenylpentyloxy))phenyl]cyclohexanol (1.45 g., 3.27 mmol.).

PMR: $\delta_{CDCl_3}{}^{TMS}$ 1.25 (d, J=6 Hz, methyl), 3.75 (m, carbinol methine), 4.20 (m, sidechain methine), 6.23 (bs, ArH), 6.40 (dd, J=8 and 2 Hz, ArH), 6.98 (d, J=8 Hz, ArH) and 7.13 (s, PhH).

IR: (CHCl₃) 3597, 3333, 1623 and 1597 cm⁻¹.

MS: m/e 354 (M+), 336, 208, 190 and 91.

Analysis: Calc'd for $C_{23}H_{30}O_3$: C, 77.93; H, 8.53% Found: C, 77.95; H, 8.31%.

trans-3-[2-hydroxy-4-(2-(5-phenylpentyloxy))-phenyl]cyclohexanol (241 mg., 90%), m.p. 65°–70° C. (pentane) from trans-3-[2-benzyloxy-4-(2-(5-phenylpentyloxy))phenyl]cyclohexanol (0.355 g., 0.754 mmol.).

PMR: $\delta_{CDCl_3}{}^{TMS}$ 1.25 (d, J=6 Hz, sidechain methyl), 4.13 (m, carbinol and sidechain methines), 6.26 (d, J=2 Hz, ArH), 6.26 (dd, J=8 and 2 Hz, ArH), 6.82 (d, J=8 Hz, ArH) and 7.05 (s, PhH).

IR: (CHCl₃) 3597, 3378, 1629, and 1587 cm⁻¹.

MS: m/e 354 (M+), 336, 208, 190 and 91.

Analysis: Calc'd for $C_{23}H_{30}O_3$: C, 77.93; H, 8.53% Found: C, 77.53; H, 8.40%.

cis-3-[4-(1,1-dimethyloctyl)-2-hydroxyphenyl]cyclohexanol (0.725 g., 68%) from 1.36 g. (3.22 mmol.) of cis-3-[2-benzyloxy-4-(1,1-dimethyloctyl)phenyl]cyclohexanol.

M.P.: 100°–101° C. (recrystallized from hexane).

PMR: $\delta_{CDCl_3}{}^{TMS}$ 0.82 (m, terminal sidechain methyl), 1.22 (s, gem dimethyl), 2.90 (m, benzylic methine), 3.12 (bs, OH), 3.70 (m, carbinol methine), 6.62 (d, J=2 Hz, ArH), 6.75 (dd, J=8 and 2 Hz, ArH) and 7.00 (d, J=8 Hz, ArH).

IR: (CHCl₃) 3571, 3333, 1626 and 1582 cm⁻¹.

MS: m/e 332 (M+), 314, 233 and 215.

Analysis: Calc'd for $C_{22}H_{36}O_2$: C, 79.46; H, 10.92% Found: C, 79.85; H, 11.03%.

trans-3-[4-(1,1-dimethyloctyl)-2-hydroxyphenyl]cyclohexanol (0.195 g., 100%) as an oil from 246 mg. (0.582 mmol.) of trans-3-[2-benzyloxy-4-(1,1-dimethyloctyl)phenyl]cyclohexanol.

M.P.: 94°–95° C. (from petroleum ether).

PMR: $\delta_{CDCl_3}{}^{TMS}$ 0.82 (m, terminal sidechain methyl), 1.24 (s, gem dimethyl), 3.28 (m, benzylic methine), 4.20 (m, carbinol methine and OH), 6.83 (dd, J=8 and 2 Hz, ArH), 6.83 (d, J=2 Hz, ArH) and 7.10 (d, J=8 Hz, ArH).

IR: (CHCl₃) 3650, 3436, 1639 and 1582 cm⁻¹.

MS: m/e 332 (M+), 314, 233 and 215.

Analysis: Calc'd for $C_{22}H_{36}O_2$: C, 79.46; H, 10.92% Found: C, 79.34; H, 10.55%.

cis-3-(4-t-butyl-2-hydroxyphenyl)cyclohexanol (3.99 g., 77%) from cis-3-(2-benzyloxy-4-t-butylphenyl)cyclohexanol (7.1 g., 0.021 mole).

M.P.: 177°–178° C. (from isopropyl ether).

PMR: $\delta_{CDCl_3}{}^{TMS}$ 1.23 (s, t-butyl), 2.88 (m, benzylic methine), 3.55 (m, carbinol methine), 6.75 (m, two ArH) and 6.92 (d, J=8 Hz, ArH).

IR: (KBr) 3484, 3268, 1634 and 1592 cm⁻¹.

MS: m/e 248 (M+), 233, 230, 215, 187, 176, 173 and 161.

Analysis: Calc'd for $C_{16}H_{25}O_2$: C, 77.37; H, 9.74% Found: C, 77.00; H, 9.54%.

trans-3-(4-t-butyl-2-hydroxyphenyl)cyclohexanol (0.725 g., 99%) from trans-3-(2-benzyloxy-4-t-butylphenyl)cyclohexanol (1.25 g., 2.96 mmoles).

M.P.: 136°–137° C. (from isopropyl ether).

PMR: $\delta_{CDCl_3}{}^{TMS}$ 1.27 (s, t-butyl), 3.35 (m, benzylic methine), 4.32 (m, carbinol methine), 6.95 (d, J=2 Hz, ArH), 6.96 (dd, J=8 and 2 Hz, ArH) and 7.15 (d, J=8 Hz, ArH).

IR: (CHCl$_3$) 3623, 3401, 1626 and 1575 cm$^{-1}$.

MS: m/e 248 (M+), 233, 230, 215, 187 and 173.

Analysis: Calc'd for C$_{16}$H$_{24}$O$_2$: C, 77.37; H, 9.74% Found: C, 77.34; H, 9.49%.

cis-3-[4-(1,1-dimethylpropyl)-2-hydroxyphenyl]cyclohexanol (1.45 g., 32%) from cis-3-[2-benzyloxy-4-(1,1-dimethylpropyl)phenyl]cyclohexanol (6.1 g., 0.0173 mole).

M.P.: 166°–167° C. (from isopropyl ether).

PMR: $\delta_{CDCl_3}{}^{TMS}$-DMSO-D$_6$ 0.65 (t, J=7 Hz, terminal methyl), 1.20 (s, gem dimethyl), 2.91 (m, benzylic methine), 3.62 (m, carbinol methine), 6.75 (m, two ArH), 7.02 (d, J=8 Hz, ArH) and 7.55 (s, OH).

IR: (KBr) 3509, 3279, 1629 and 1592 cm$^{-1}$.

MS: m/e 262 (M+), 247, 244, 233 and 215.

trans-3-[4-(1,1-dimethylpropyl)-2-hydroxyphenyl]cyclohexanol (0.50 g., 68%) from trans-3-[2-benzyloxy-4-(1,1-dimethylpropyl)phenyl]cyclohexanol (1.00 g., 2.84 mmoles).

M.P.: 124°–125° C. (from isopropyl ether).

PMR: $\delta_{CDCl_3}{}^{TMS}$ 0.67 (t, J=7 Hz, terminal methyl), 1.23 (gem dimethyl), 3.30 (m, benzylic methine), 4.05 (m, carbinol methine), 6.76 (m, two ArH) and 6.93 (d, J=8 Hz, ArH).

IR: (CHCl$_3$) 3636, 3413, 1639 and 1585 cm$^{-1}$.

MS: m/e 262 (M+), 247, 244, 233 and 215.

Analysis: Calc'd for C$_{17}$H$_{26}$O$_2$: C, 77.82; H, 9.99% Found: C, 77.51; H, 9.87%.

cis-3-[4-(1,1-dimethylbutyl)-2-hydroxyphenyl]cyclohexanol (1.9 g., 74%) from cis-3-[2-benzyloxy-4-(1,1-dimethylbutyl)phenyl]cyclohexanol (3.39 g., 9.26 mmoles).

M.P.: 138°–139° C. (from pentane).

PMR: $\delta_{CDCl_3}{}^{TMS}$ 0.82 (m, terminal methyl), 1.25 (s, gem dimethyl), 2.90 (m, benzylic methine), 3.78 (m, carbinol methine), 6.8 (m, ArH) and 7.11 (d, J=8 Hz, ArH).

IR: (KBr) 3509, 3279, 1629 and 1592 cm$^{-1}$. MS: m/e 276 (M+), 261, 258, 233 and 215.

trans-3-[4-(1,1-dimethylbutyl)-2-hydroxyphenyl]cyclohexanol (0.45 g., 87%) as an oil from trans-3-[2-benzyloxy-4-(1,1-dimethylbutyl)phenyl]cyclohexanol (0.700 g., 1.91 mmoles).

PMR: $\delta_{CDCl_3}{}^{TMS}$ 0.80 (m, terminal methyl), 1.22 (s, gem dimethyl), 3.25 (m, benzylic methine), 4.22 (m, carbinol methine), 6.81 (d, J=2 Hz, ArH), 6.81 (dd, J=8 and 2 Hz, ArH) and 7.06 (d, J=8 Hz, ArH).

IR: (CHCl$_3$) 3636, 3390, 1629 and 1575 cm$^{-1}$.

MS: m/e 276 (M+), 261, 258, 233 and 215.

trans-3-[4-(1,1-Dimethylheptyl)-2-hydroxyphenyl]-cis-4-propylcyclohexanol (626 mg., 78%) from trans-3-[2-benzyloxy-4-(1,1-dimethylheptyl)phenyl]-cis-4-(2-propenyl)cyclohexanol (1.0 g., 2.23 mmole).

M.P.: 92°–94° C.

PMR: $\delta_{CDCl_3}{}^{TMS}$ 0.85 (m, terminal methyls), 1.25 (s, gem dimethyl), 3.05 (m, benzylic methine), 4.22 (m, carbinol methine), 6.55–6.9 (m, ArH) and 7.01 (d, J=8 Hz, ArH).

IR: (CHCl$_3$) 3623, 3390, 1629 and 1578 cm$^{-1}$.

Analysis: Calc'd for C$_{24}$H$_{40}$O$_2$: C, 79.94; H, 11.18% Found: C, 80.10; H, 10.89%.

cis-3-[4-(1,1-Dimethylheptyl)-2-hydroxyphenyl]-trans-4-propylcyclohexanol (550 mg., 74%) from cis-3-[2-benzyloxy-4-(1,1-dimethylheptyl)phenyl]-trans-4-(2-propenyl)cyclohexanol (930 mg., 2.07 mmole).

M.P.: 126° C. (from pentane).

IR: (CHCl$_3$) 3597, 3390, 1629 and 1575 cm$^{-1}$.

MS: m/e 360 (M+), 345, 342, 275 and 257.

PMR: $\delta_{CDCl_3}{}^{TMS}$ 0.82 (m, terminal methyls), 1.27 (s, gem dimethyl), 2.65 (m, benzylic methine), 3.75 (m, carbinol methine), 0.75 (m, ArH) and 7.07 (d, J=8 Hz, ArH).

Analysis: Calc'd for C$_{24}$H$_{40}$O$_2$: C, 79.94; H, 11.18% Found: C, 79.85; H, 10.95%.

trans-4-Butyl-cis-3-[4-(1,1-dimethylheptyl)-2-hydroxyphenyl]cyclohexanol (322 mg., 80%) from cis-3-[2-benzyloxy-4-(1,1-dimethylheptyl)phenyl-trans-4-(2-butenyl)cyclohexanol (500 mg., 1.08 mmole).

M.P.: 131° C. (from pentane).

IR: (CHCl$_3$) 3636, 3356, 1629 and 1587 cm$^{-1}$.

MS: m/e 374 (M+), 356, 302, 289, 272, 271, 257, 247, 233, 217, 187 and 161.

PMR: $\delta_{CDCl_3}{}^{TMS}$ 0.8 (m, terminal methyls), 1.28 (s, gem dimethyl), 2.67 (m, benzylic methine), 3.70 (m, carbinol methine), 6.69 (d, J=2 Hz, ArH), 6.82 (dd, J=8 and 2 Hz, ArH) and 7.07 (d, J=8 Hz, ArH).

trans-4-Pentyl-cis-3-[4-(1,1-dimethylheptyl)-2-hydroxyphenyl]cyclohexanol (225 mg., 76%) from cis-3-[2-benzyloxy-4-(1,1-dimethylheptyl)phenyl]-trans-4-(2-pentenyl)cyclohexanol (363 mg., 0.762 mmole).

M.P.: 135°–136° C.

PMR: $\delta_{CDCl_3}{}^{TMS}$ 0.8 (m, terminal methyls), 1.23 (s, gem dimethyl), 2.65 (m, benzylic methine), 3.75 (m, carbinol methine), 4.88 (s, OH), 6.78 (m, ArH) and 7.02 (d, J=8 Hz, ArH).

cis-3-[4-(1,1-Dimethylpentyl)-2-hydroxyphenyl]cyclohexanol (2.5 g., 60%) from cis-3-[2-benzyloxy-4-(1,1-dimethylpentyl)phenyl]cyclohexanol (5.5 g., 0.0144 mole).

M.P.: 112°–113° C. (from pentane, isopropyl ether).

IR: (CHCl$_3$) 3636, 3390, 1631 and 1592 cm$^{-1}$.

MS: m/e 290 (M+), 272, 233 and 215.

PMR: $\delta_{CDCl_3}{}^{TMS}$ 0.80 (m, terminal methyl), 1.20 (s, gem dimethyl), 2.90 (m, benzylic methylene), 3.61 (m, carbinol methine) and 6.4–7.1 (m, ArH).

Analysis: Calc'd for C$_{19}$H$_{30}$O$_2$: C, 78.57; H, 10.41% Found: C, 78.76; H, 10.11%.

trans-3-[4-(1,1-Dimethylphenyl)-2-hydroxyphenyl]cyclohexanol (385 mg., 78%) from trans-3-[2-benzyloxy-4-(1,1-dimethylpentyl)phenyl]cyclohexanol (640 mg., 1.68 mmole).

M.P.: 114°–115° C. (from pentane).

IR: (CHCl$_3$) 3636, 3390, 1631 and 1577 cm$^{-1}$.

MS: m/e 290 (M+), 272, 233 and 215.

PMR: $\delta_{CDCl_3}{}^{TMS}$ 0.80 (m, terminal methyl), 1.27 (s, gem dimethyl), 3.30 (m, benzylic methine), 4.28 (m, carbinol methine), 4.72 (bs, OH), 6.81 (dd, J=8 and 2 Hz, ArH), 6.81 (d, J=2 Hz, ArH) and 7.03 (d, J=8 Hz, ArH).

Analysis: Calc'd for C$_{19}$H$_{30}$O$_2$: C, 78.57; H, 10.41% Found: C, 78.38; H, 10.10%.

cis-3-[4-(1,1-Dimethylhexyl)-2-hydroxyphenyl]cyclohexanol (2.3 g., 99%) from cis-3-[2-benzyloxy-4-(1,1-dimethylhexyl)phenyl]cyclohexanol (3.00 g., 7.61 mmole).

M.P.: 98°–100° C. (pentane).

IR: (CHCl$_3$) 3636, 3367, 1626 and 1587 cm$^{-1}$.

MS: m/e 304 (M+), 286, 233 and 215.

PMR: $\delta_{CDCl_3}{}^{TMS}$ 0.82 (m, terminal methyl), 1.20 (s, gem dimethyl), 2.92 (m, benzylic methine), 3.76 (m, carbinol methine) and 6.65–7.4 (m, ArH).

Analysis: Calc'd for $C_{20}H_{32}O_2$: C, 78.89; H, 10.59%
Found: C, 78.57; H, 10.46%.

trans-3-[4-(1,1-Dimethylhexyl)-2-hydroxyphenyl]cyclohexanol (440 mg., 86%) from trans-3-[2-benzyloxy-4-(1,1-dimethylhexyl)phenyl]cyclohexanol (660 mg., 1.68 mmole).

M.P.: 113°–114° C. (pentane).
IR: (CHCl$_3$) 3636, 3390, 1631, 1616 and 1580 cm$^{-1}$.
MS: m/e 304 (M+), 286, 233 and 215.
HRMS: 304.2419 ($C_{20}H_{32}O_2$)

cis-3-[4-(1,1-Dimethylnonyl)-2-hydroxyphenyl]cyclohexanol (4.0 g., 100%) from cis-3-[2-benzyloxy-4-(1,1-dimethylnonyl)phenyl]cyclohexanol (5.0 g., 1.15 mmole).

M.P.: 82°–83° C. (pentane).
IR: (CHCl$_3$) 3650, 3390, 1637 and 1597 cm$^{-1}$.
MS: m/e 346 (M+), 328, 233 and 215.

Analysis: Calc'd for $C_{23}H_{38}O_2$: C, 79.71; H, 11.05%
Found: C, 79.71; H, 11.14%.

trans-3-[4-(1,1-Dimethylnonyl)-2-hydroxyphenyl]cyclohexanol (709 mg., 89%) from trans-3-[2-benzyloxy-4-(1,1-dimethylnonyl)phenyl]cyclohexanol (1.00 g., 2.29 mmole).

M.P.: 69°–70° C. (pentane).
IR: (CHCl$_3$) 3636, 3413, 1631, 1618 and 1582 cm$^{-1}$.
MS: m/e 346 (M+), 328, 233 and 215.
PMR: $\delta_{CDCl_3}{}^{TMS}$ 0.87 (m, terminal methyl), 1.22 (s, gem dimethyl), 3.30 (m, benzylic methine), 4.22 (m, carbinol methine), 4.98 (bs, OH) and 6.7–7.3 (m, ArH).

Analysis: Calc'd for $C_{23}H_{38}O_2$: C, 79.71; H, 11.05%
Found: C, 79.11; H, 10.86%.

cis-3-[4-(1,1-Dimethyldecyl)-2-hydroxyphenyl]cyclohexanol (2.02 g., 98%) from cis-3-[2-benzyloxy-4-(1,1-dimethyldecyl)phenyl]cyclohexanol (2.6 g., 5.78 mmole).

M.P.: 93°–94° C. (pentane).
IR: (CHCl$_3$) 3636, 3390, 1629 and 1587 cm$^{-1}$.
MS: m/e 360 (M+), 342, 288, 233 and 215.
PMR: $\delta_{CDCl_3}{}^{TMS}$ 0.83 (m, terminal methyl), 1.20 (s, gem dimethyl), 2.85 (m, benzylic methine), 3.75 (m, carbinol methine), 4.4 (broad, OH) and 6.4–7.2 (m, ArH).

Analysis: Calc'd for $C_{24}H_{40}O_2$: C, 79.94; H, 11.18%
Found: C, 80.12; H, 11.39%.

trans-3-[4-(1,1-Dimethyldecyl)-2-hydroxyphenyl]cyclohexanol (130 mg., 45%) from trans-3-[2-benzyloxy-4-(1,1-dimethyldecyl)phenyl]cyclohexanol (360 mg., 0.80 mmole).

M.P.: 76°–77° C.
IR: (CHCl$_3$) 3636, 3425, 1631, 1616 and 1580 cm$^{-1}$.
MS: m/e 360 (M+), 342, 233 and 215.
PMR: $\delta_{CDCl_3}{}^{TMS}$ 0.86 (m, terminal methyl), 1.22 (s, gem dimethyl), 3.2 (m, benzylic methine), 4.17 (m, carbinol methine and OH) and 6.6–7.2 (m, ArH).

Analysis: Calc'd for $C_{24}H_{40}O_2$: C, 79.94; H, 11.18%
Found: C, 80.20; H, 11.27% cis-3-[4(1,1-Dimethylundecyl]-2-hydroxyphenyl]cyclohexanol (2.39 g., 85%) from cis-3-[2-benzyloxy-4-(1,1-dimethylundecyl)phenyl]cyclohexanol (3.5 g., 7.54 mmole).

M.P.: 85°–86° C.
IR: (CHCl$_3$) 3636, 3390, 1634 and 1592 cm$^{-1}$.
MS: m/e 374 (M+), 356, 233 and 215.

PMR: $\delta_{CDCl_3}{}^{TMS}$ 0.89 (m, terminal methyl), 1.22 (s, gem dimethyl), 2.98 (m, benzylic methine), 3.95 (m, carbinol methine), 6.83 (m, ArH) and 7.09 (d, J=8 Hz, ArH).

Analysis: Calc'd for $C_{25}H_{42}O_2$: C, 80.15; H, 11.30%
Found: C, 80.00; H, 11.48%.

trans-3-[4-(1,1-Dimethylundecyl)-2-hydroxyphenyl]cyclohexanol (487 mg., 60%) from trans-3-[2-benzyloxy-4-(1,1-dimethylundecyl)phenyl]cyclohexanol (1.00 g., 2.16 mmole).

M.P.: 73°–74° C.
IR: (CHCl$_3$) 3636, 3413, 1637 and 1585 cm$^{-1}$.
MS: m/e 374 (M+), 356, 233 and 215.
PMR: $\delta_{CDCl_3}{}^{TMS}$ 0.89 (m, terminal methyl), 1.27 (s, gem dimethyl), 3.25 (m, benzylic methine), 4.31 (m, carbinol methine), 5.07 (bs, OH) and 6.7–7.3 (m, ArH).

Analysis: Calc'd for $C_{25}H_{42}O_2$: C, 80.15; H, 11.30%
Found: C, 80.11; H, 11.16% cis-3-[4-(1,1-Dimethylheptyl)-2-hydroxyphenyl]cyclooctanol (0.793 g., 73%) from cis-3-[2-benzyloxy-4-(1,1-dimethylheptyl)phenyl]cyclooctanol (1.36 g., 3.11 mmole).

M.P.: 89°–90° C. (from pentane).
MS: m/e 346 (M+), 328, 261 and 243.
PMR: $\delta_{CDCl_3}{}^{TMS}$ 0.83 (m, terminal methyl), 1.22 (s, gem dimethyl), 3.0 (bm, benzylic methine), 3.98 (bm, carbinol methine), 6.75 (m, ArH) and 7.00 (d, J=8 Hz, ArH).

Analysis: Calc'd for $C_{23}H_{38}O_2$: C, 79.71; H, 11.05%
Found: C, 79.90; H, 10.89% trans-3-[4-(1,1-Dimethylheptyl)-2-hydroxyphenyl]cyclooctanol (2.62 g., 83%) from trans-3-[2-benzyloxy-4-(1,1-dimethylheptyl)phenyl]cyclooctanol (4.0 g., 9.17 mmole).

M.P.: 76°–77° C., (from pentane).
MS: m/e 346 (M+), 328, 261 and 243.
PMR: $\delta_{CDCl_3}{}^{TMS}$ 0.83 (m, terminal methyl), 1.24 (s, gem dimethyl), 3.15 (bm, benzylic methine), 4.05 (m, carbinol methine), 6.78 (m, ArH) and 7.02 (d, J=8 Hz, ArH).

Analysis: Calc'd for $C_{23}H_{38}O_2$: C, 79.71; H, 11.05%
Found: C, 79.81; H, 10.86%

EXAMPLE 5

3-[2-Benzyloxy-4-(1,1-Dimethylheptyl)phenyl]cyclohex-2-enone

A solution of 3.89 g. (10 mmoles) of 2-(3-benzyloxy-4-bromophenyl)-2-methyloctane in 10 ml. of tetrahydrofuran was slowly added to 360 mg. (14.4 mmoles) of 70–80 mesh magnesium metal. The resulting mixture was refluxed for 30 minutes and then cooled to 0° C. To this solution was slowly added a solution of 1.40 g. (10 mmoles) of 3-ethoxy-2-cyclohexen-1-one in 3 ml. of tetrahydrofuran. The reaction mixture was stirred for 30 minutes at 0° C. and then quenched by the addition of 20 ml. of 1N sulfuric acid and heating on the steam bath for 30 minutes. It was then cooled and added to 200 ml. of ether-200 ml. of water. The organic extract was washed successively with 200 ml. of saturated sodium bicarbonate and 200 ml. of saturated sodium chloride, dried over magnesium sulfate and evaporated to an oil. The crude product was purified via column chromatography on 170 g. of silica gel eluted with 1:1 ether:pentane to yield 2.5 g. (54%) of the title compound as an oil.

PMR: $\delta_{CDCl_3}{}^{TMS}$ 0.87 (m, sidechain terminal methyl), 1.30 (s, gem dimethyl), 2.05 (dt, J=6&6 Hz, C-5 methylene), 2.50 (t, J=6 Hz, C-4 methylene), 2.80 (t, J=6 Hz, C-6 methylene), 5.19 (s, benzyl ether methylene), 6.30 (t, J=1 Hz, vinyl proton), 7.00 (dd, J=8&2 Hz, ArH), 7.02 (d, J=2 Hz, ArH), 7.25 (d, J=8 Hz, ArH) and 7.45 (s, PhH).

IR: (CHCl$_3$) 1667, 1610 and 1558 cm$^{-1}$.

MS: m/e 404 (M+), 319, 313 and 91.

Similarly, 3-[2-benzyloxy-4-(1,1-dimethylheptyl)-phenyl]-4-methylcyclohex-2-enone was prepared as an oil (4.12 g., 77%) using 3-ethoxy-6-methyl-2-cyclohexen-1-one (1.98 g., 12.9 mmoles), magnesium (0.61 g., 25.7 mmoles) and 12.9 mmoles (5.0 g.) of 2-(3-benzyloxy-4-bromophenyl)-2-methyloctane.

IR: (CHCl$_3$) 1667, 1613, and 1565 cm$^{-1}$.

MS: m/e 418 (M+), 400, 385, 333, 327, 299, 291 and 91.

PMR: $\delta_{CDCl_3}{}^{TMS}$ 0.85 (m, terminal methyl, 1.02 (d, J=7 Hz, methyl), 2.45 (m, methylene), 3.2 (m, allylic methine), 5.10 (s, benzylic methylene), 6.01 (d, J=1 Hz, vinyl H), 6.90 (m, ArH) and 7.37 (s, Ph).

The following compounds are prepared in like manner from appropriate 3-alkoxy-2-cycloalken-1-ones and 2-bromo-5-(Z-W substituted)phenol benzyl ethers:

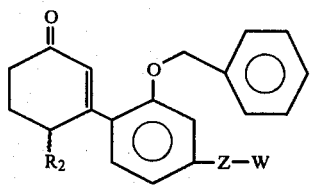

| R$_2$ | Z | W |
|---|---|---|
| H | OCH(CH$_3$)(CH$_2$)$_3$ | C$_6$H$_5$ |
| H | OCH$_2$ | C$_6$H$_5$ |
| H | O(CH$_2$)$_8$ | C$_6$H$_5$ |
| H | O(CH$_2$)$_4$ | 4-FC$_6$H$_4$ |
| H | O(CH$_2$)$_{10}$ | 4-ClC$_6$H$_5$ |
| H | O(CH$_2$)$_{13}$ | C$_6$H$_5$ |
| H | O(CH$_2$)$_{13}$ | H |
| H | OC(CH$_3$)$_2$(CH$_2$)$_5$ | H |
| H | O | C$_6$H$_5$ |
| H | CH(CH$_3$)(CH$_2$)$_3$ | C$_6$H$_5$ |
| H | (CH$_2$)$_4$ | C$_6$H$_5$ |
| H | (CH$_2$)$_9$ | H |
| H | (CH$_2$)$_3$ | 2-pyridyl |
| H | (CH$_2$)$_{10}$ | 4-pyridyl |
| H | CH(c$_2$H$_5$)(CH$_2$)$_2$ | 4-pyridyl |
| H | CH(CH$_3$)CH(CH$_3$)CH$_2$ | 3-pyridyl |
| H | O(CH$_2$)$_2$ | 4-pyridyl |
| H | O(CH$_2$)$_{10}$ | 2-pyridyl |
| H | (CH$_2$)$_3$O(CH$_2$)$_3$ | H |
| H | (CH$_2$)$_2$O(CH$_2$)$_{10}$ | H |
| H | (CH$_2$)$_4$OCH$_2$ | C$_6$H$_5$ |
| H | (CH$_2$)$_6$OCH$_2$ | 4-ClC$_6$H$_4$ |
| H | CH(CH$_3$)CH(CH$_3$)(CH$_2$)$_5$ | H |
| H | C(CH$_3$)$_2$(CH$_2$)$_7$ | H |

EXAMPLE 6

3-[2-Benzyloxy-4-(1,1-dimethylheptyl)phenyl]-3-methylcyclohexanone

To a −10° C. to −5° C. solution of 4.17 mmoles of dimethylcopper lithium in 10 ml. of tetrahydrofuran was slowly added 5.60 g. (1.39 mmoles) of 3-[2-benzyloxy-4-(1,1-dimethylheptyl)phenyl]cyclohex-2-enone in 5 ml. of tetrahydrofuran. The reaction mixture was stirred for 30 minutes longer and was then added to 100 ml. of saturated ammonium chloride and 100 ml of ether. After stirring for 10 minutes the quenched reaction was extracted with 200 ml. of ether. The ether extract was washed with 100 ml. of saturated sodium chloride, dried over magnesium sulfate and evaporated to an oil. The oil was purified via preparative layer chromatography on three 20 cm.×20 cm.×2 mm. silica gel plates eluted with 2:1 cyclohexane:ether to yield 282 mg. (48%) (higher Rf) of the title compound, as an oil, and 211 mg. (36%) (lower Rf) of 3-[2-benzyloxy-4-(1,1-dimethylheptyl)phenyl]-1-methylcyclohex-2-en-1-ol, as an oil.

Title compound:

PMR: $\delta_{CDCl_3}{}^{TMS}$ 0.82 (m, terminal sidechain methyl), 1.22 (s, gem dimethyl), 1.40 (s, C-3 methyl), 2.30 and 3.05 (AB quartet, J=14 Hz, C-2 methylene), 5.02 (s, benzyl ether methylene), 6.6–7.3 (m, ArH) and 7.25 (s, PhH).

IR: (CHCl$_3$) 1704, 1610, 1565 cm$^{-1}$.

MS: m/e 420 (M+), 405, 377, 335 and 329.

3-[2-Benzyloxy-4-(1,1-dimethylheptyl)phenyl]-1-methylcyclohex-2-en-1-ol:

PMR: $\delta_{CDCl_3}{}^{TMS}$ 0.82 (m, terminal sidechain methyl), 1.25 (s, gem dimethyl), 1.30 (s, C-1 methyl), 2.34 (m, C-4 methylene), 5.00 (s, benzyl ether methylene), 5.65 (bt, J=1 Hz, vinyl proton), 6.7–6.9 (M, ArH), 7.00 (d, J=8 Hz, ArH) and 7.30 (s, PhH).

IR: (CHCl$_3$) 3571, 3401, 1661, 1608 and 1585 cm$^{-1}$.

MS: m/e 420 (M+), 402, 335 and 317.

Repetition of this procedure but using the appropriate cyclohex-2-enones of Example 5 affords compounds having the following formula wherein Z and W are as defined in Example 5.

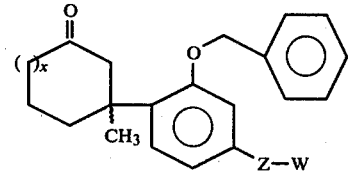

EXAMPLE 7

3-[4-(1,1-Dimethylheptyl)-2-hydroxyphenyl]cyclohex-2-enone

A mixture of 400 mg. (0.988 mmole) of 3-[2-benzyloxy-4-(1,1-dimethylheptyl)phenyl]cyclohex-2-enone and 20 mg. of 5% palladium-on-carbon was stirred under one atmosphere of hydrogen pressure for 30 minutes. The reaction mixture was then filtered through diatomaceous earth with ether and the filtrate evaporated to a solid. The crude solid was recrystallized from petroleum ether to yield 110 mg. (35%) of the title compound, M.P. 122°–123° C.

PMR: $\delta_{CDCl_3}{}^{TMS}$ 0.82 (m, sidechain terminal methyl), 1.30 (s, gem dimethyl), 2.19 (dt, J=6&6 Hz, C-5 methylene), 2.52 (t, J=6 Hz, C-4 methylene), 2.80 (t, J=6 Hz, C-6 methyl), 6.7–7.4 (m, ArH and vinyl proton) and 8.16 (s, phenol.)

IR: (KBr) 3448, 1634, 1608 and 1565 cm$^{-1}$.

MS: m/e 314 (M+), 299 and 229.

Analysis: Calc'd for C$_{21}$H$_{30}$O$_2$: C, 80.21; H, 9.62%
Found: C, 80.23; H, 9.46%.

In like manner the remaining 3-[2-benzyloxy-4-(Z-W)phenyl]cycloalk-2-enones of Example 5 are converted to the corresponding 3-[4-(Z-W)-2-hydroxyphenyl]-cycloalk-2-enones.

EXAMPLE 8

3-(2,4-Dihydroxyphenyl)cyclohexanone Methyl Ketal

To a 0° C. solution of 7.0 g. (33.0 mmol.) of 3-(2,4-dihydroxyphenyl)cyclohexanone in 100 ml. of methanol and 15 ml. of trimethyl orthoformate was added 10 drops of concentrated sulfuric acid. The reaction mixture was then stirred for 3 hours with no cooling, the temperature being allowed to rise to room temperature, and was then quenched by the addition of excess solid sodium bicarbonate. The reaction mixture was evaporated under reduced pressure and the residue dissolved in 200 ml. of water-250 ml. of ether. The ether extract was washed once with 150 ml. of saturated sodium bicarbonate, dried over magnesium sulfate and evaporated. The oily residue was crystallized from ether-pentane to yield 5.74 g. (77%) of the title compound, m.p. 129°-130° C.

PMR: $\delta_{CDCl_3}^{TMS}$ 1.4–2.5 (m, methylenes), 3.20 (m, methine), 3.50 (s, OMe), 5.58 (s, OH), 6.38 (dd, J=8 and 2 Hz, ArH), 6.48 (s, overlaps δ6.38) and 6.87 (d, J=8 Hz).

IR: (KBr) 3289, 1629, 1613 and 1597 cm$^{-1}$.

MS: 220 (M+), 205, 203, 188, 177, 161 and 136.

Analysis: Calc'd for $C_{13}H_{16}O_3$: C, 70.89; H, 7.32% Found: C, 70.79; H, 7.34%.

Repetition of this procedure but using triethyl, tri-n-propyl or tri-n-butyl orthoformate in place of trimethyl orthoformate and ethyl, n-propyl or n-butyl alcohol in place of methanol produces the corresponding ethyl, n-propyl and n-butyl ketals.

EXAMPLE 9

3-[2-Hydroxy-4-(4-phenylbutyloxy)phenyl]cyclohexanone Methyl Ketal

A mixture of 5.03 g. (22.8 mmol.) of 3-(2,4-dihydroxyphenyl)cyclohexanone methyl ketal, 10.1 g. (73.2 mmol.) of anhydrous potassium carbonate and 6.12 g. (26.8 mmol.) of 4-phenylbutyl methanesulfonate in 25 ml. of N,N-dimethylformamide was heated at 85°–100° C. for 4 hours. The reaction mixture was cooled and added to 200 ml. of water-200 ml. of ether. The ether extract was washed twice with 200 ml. of water, dried over magnesium sulfate and evaporated to an oil. The oil was purified via column chromatography on 400 g. of silica gel eluted with 2:1 pentane:ether to yield 7.4 g. (92%) of the title compound as an oil.

PMR: $\delta_{CDCl_3}^{TMS}$ 2.63 (m, benzylic methylene), 3.33 (s, OCH$_3$), 3.85 (bt, J=6 Hz, OCH$_2$), 6.42 (dd, J=8 and 2 Hz, ArH), 6.50 (bs, overlaps δ6.42, ArH), 6.92 (d, J=8 Hz, ArH) and 7.30 (s, PhH).

IR: (CHCl$_3$) 1623 and 1590 cm$^{-1}$.

MS: m/e 352 (M+) and 91.

Analysis: Calc'd for $C_{23}H_{28}O_3$: C, 78.37; H, 8.01% Found: C, 78.34; H, 8.07%.

The following compounds were similarly prepared but using the appropriate mesylate derivative in place of 4-phenylbutyl methanesulfonate:

3-[2-hydroxy-4-(2-heptyloxy)phenyl]cyclohexanone methyl ketal (6.13 g., 75%) as an oil from 5.7 g. (25.9 mmole) of 3-(2,4-dihydroxyphenyl)cyclohexanone methyl ketal and (2-heptyl)methanesulfonate (6.2 g., 32.3 mmole).

IR: (CHCl$_3$) 1637 and 1600 cm$^{-1}$.

MS: m/e 318 (M+), 286, 274, 220, 204 and 178.

PMR: $\delta_{CHCl_3}^{TMS}$ 0.90 (m, methyl), 1.18 (d, J=7 Hz, methyl), 3.03 (m, methine), 3.35 (s, MeO), 4.14 (m, methine), 6.35 (m, ArH) and 6.68 (d, J=8 Hz, ArH).

3-[2-hydroxy-4-(2-octyloxy)phenyl]cyclohexanone methyl ketal as an oil (5.03 g., 58%) from 3-(2,4-dihydroxyphenyl)cyclohexanone methyl ketal (5.7 g., 25.9 mmole) and (2-octyl)methanesulfonate (7.3 g., 35.1 mmole).

IR: (CHCl$_3$) 1639 and 1600 cm$^{-1}$.

MS: m/e 332 (M+), 300, 289, 272 and 220.

PMR: $\delta_{CDCl_3}^{TMS}$ 0.87 (m, methyl), 3.09 (m, methine), 3.36 (s, OMe), 4.20 (m, methyl), 6.30 (m, ArH) and 6.80 (d, J=8 Hz, ArH).

3-[2-hydroxy-4-(2-nonyloxy)phenyl]cyclohexanone methyl ketal (5.23 g., 59%) as an oil from 3-(2,4-dihydroxyphenyl)cyclohexanone methyl ketal (5.7 g., 25.9 mmole) and (2-nonyl)methanesulfonate (7.9 g., 35.5 mmole).

IR: (CHCl$_3$) 1634 and 1590 cm$^{-1}$.

MS: m/e 346 (M+), 314, 220, 188 and 161.

PMR: $\delta_{CDCl_3}^{TMS}$ 0.87 (m, methyl), 3.10 (m, methine), 3.39 (s, OMe), 4.22 (m, methine), 6.36 (m, ArH) and 6.80 (d, J=8 Hz, ArH).

3-[2-hydroxy-4-(2-(4-phenyl)butoxy)phenyl]cyclohexanone methyl ketal as an oil (5.1 g., 56%) from 3-(2,4-dihydroxyphenyl)cyclohexanone methyl ketal (5.7 g., 25.9 mmole) and 2-(4-phenylbutyl)methanesulfonate (8.0 g., 35.0 mmole).

IR: (CHCl$_3$) 1639 and 1603 cm$^{-1}$.

MS: m/e 352 (M+), 320, 220 and 188.

PMR: $\delta_{CDCl_3}^{TMS}$ 1.29 (d, J=6 Hz, methyl), 3.07 (m, methine), 3.38 (s, OMe), 4.26 (m, methine), 6.30 (m, ArH), 6.80 (d, J=9 Hz, ArH) and 7.16 (s, Ph).

3-[2-hydroxy-4-(2-(6-phenyl)hexyloxy)phenyl]cyclohexanone methyl ketal (5.3 g., 54%) as an oil from 3-(2,4-dihydroxyphenyl)cyclohexanone methyl ketal (5.7 g., 25.9 mmole) and 2-(6-phenylhexyl)methanesulfonate (9.0 g., 35.5 mmole).

IR: (CHCl$_3$) 1634 and 1597 cm$^{-1}$.

MS: m/e 380.2342 (M+, $C_{25}H_{32}O_3$), 220.1088, 188.0986 and 177.0550.

PMR: $\delta_{CDCl_3}^{TMS}$ 1.26 (d, J=6 Hz, methyl), 3.10 (m, methine), 3.40 (s, OMe), 4.22 (m, methine), 6.30 (m, ArH), 6.83 (d, J=9 Hz, ArH) and 7.18 (s, Ph).

EXAMPLE 10

3-[2-Hydroxy-4-(4-phenylbutyloxy)phenyl]cyclohexanone

A mixture of 6.8 g. (19.3 mmol.) of 3-[2-hydroxy-4-(4-phenylbutyloxy)phenyl]cyclohexanone methyl ketal, 100 ml. of 2N hydrochloric acid and 60 ml. of dioxane was heated at reflux for one hour. The reaction mixture was cooled and added to 300 ml. of ether-500 ml. of saturated sodium chloride. The ether extract was washed once each with 500 ml. of saturated sodium chloride and 500 ml. of saturated sodium bicarbonate, dried over magnesium sulfate and evaporated to an oil. The oil was purified via column chromatography on 400 g. of silica gel eluted with 1:1 ether:cyclohexane to yield 6.4 g. (98%) of the title compound as an oil.

PMR: $\delta_{CDCl_3}^{TMS}$ 2.69 (m, benzylic methylene), 3.90 (bt, J=6 Hz, —OCH$_2$—), 6.25–6.5 (m, ArH), 6.82 (d, J=8 Hz, ArH) and 7.20 (s, PhH).

IR: (CHCl$_3$) 3571, 3333, 1718(w), 1626 and 1595 cm$^{-1}$.

MS: m/e 388 (M+), 320, 310, 295, 268 and 91.

The following compounds were prepared in like manner from appropriate ketals of Example 9:

3-[4-(2-Heptyloxy)-2-hydroxyphenyl]cyclohexanone (4.7 g. 82%) as an oil from 6.0 g. (18.8 mmole) of the corresponding methyl ketal.

IR: (CHCl$_3$) 3636, 3390, 1724(weak), 1639 and 1600 cm$^{-1}$.

MS: m/e 304 (M+), 206, 188, 171, 163 and 137.

PMR: $\delta_{CDCl_3}{}^{TMS}$ 0.82 (m, methyl), 1.25 (d, J=6 Hz, methyl), 4.15 (m, sidechain methine), 6.35 (dd, J=8 and 2 Hz, ArH), 6.35 (d, J=2 Hz, ArH) and 6.81 (d, J=8 Hz, ArH).

3-[4-(2-Octyloxy)-2-hydroxyphenyl]cyclohexanone (4.1 g., 85%) as an oil from 5.0 g. (15.0 mmole) of the corresponding methyl ketal.

IR: (CHCl$_3$) 3636, 3378, 1721(weak), 1631 and 1595 cm$^{-1}$.

MS: m/e 318 (M+), 206, 188, 178 and 163.

PMR: $\delta_{CDCl_3}{}^{TMS}$ 0.84 (m, methyl), 4.20 (m, sidechain methine), 6.39 (dd, J=8 and 2 Hz, ArH), 6.39 (d, J=2 Hz, ArH) and 6.83 (d, J=8 Hz, ArH).

3-[4-(2-Nonyloxy)-2-hydroxyphenyl]cyclohexanone (4.35 g., 89%) as an oil from 5.1 g. (14.7 mmole) of the corresponding methyl ketal.

IR: (CHCl$_3$) 3584, 3367, 1709(weak), 1626 and 1587 cm$^{-1}$.

MS: m/e 332 (M+), 206, 187 and 171.

PMR: $\delta_{CDCl_3}{}^{TMS}$ 0.85 (m, methyl), 4.26 (m, sidechain methine), 6.39 (dd, J=9 and 2 Hz, ArH), 6.39 (d, J=2 Hz, ArH) and 6.84 (d, J=8 Hz, ArH).

3-[4-(2-(4-Phenyl)butyloxy)-2-hydroxyphenyl]cyclohexanone (3.8 g., 79%) from 5.0 g. (14.2 mmole) of the corresponding methyl ketal, as an oil.

IR: (CHCl$_3$) 3636, 3425, 1724(weak), 1637 and 1600 cm$^{-1}$.

MS: m/e 338 (M+), 206, 188, 132, 117 and 91.

PMR: $\delta_{CDCl_3}{}^{TMS}$ 1.19 and 1.27 (d, J=6 Hz, methyl), 3.02 (m, methine in hemiketal form), 3.73 and 4.22 (m, methines), 6.30 (dd, J=8 and 2 Hz, ArH), 6.30 (d, J=2 Hz, ArH), 6.81 (d, J=2 Hz, ArH) and 7.18 (s, Ph).

3-[4-(2-(6-Phenyl)hexyloxy)-2-hydroxyphenyl]cyclohexanone (4.45 g., 89%) as an oil from 5.2 g. (13.6 mmole) of the corresponding methyl ketal.

IR: (CHCl$_3$) 3636, 3390, 1718, 1637 and 1600 cm$^{-1}$.

MS: m/e 366 (M+), 206, 188 and 91.

PMR: $\delta_{CDCl_3}{}^{TMS}$ 1.25 (d, J=6 Hz, methyl), 3.07 (m, methine), 4.19 (m, methine), 6.32 (dd, J=9 and 2 Hz, ArH), 6.32 (d, J=2 Hz, ArH), 6.78 (d, J=9 Hz, ArH) and 7.14 (s, Ph).

EXAMPLE 11 cis-3-[2-Hydroxy-4-(4-phenylbutyloxy)phenyl]cyclohexanol and the trans isomer

To a −18° C. solution of 4.8 g. (14.2 mmole) of 3-[2-hydroxy-4-(4-phenylbutyloxy)phenyl]cyclohexanone in 25 ml. of methanol was added 0.539 g. (14.2 mmol.) of sodium borohydride. The reaction mixture was stirred for 40 minutes and then added to 250 ml. of saturated sodium chloride-250 ml. of ether. The ether extract was washed once with 150 ml. of saturated sodium chloride, dried over magnesium sulfate and evaporated to an oil. The oil was purified via column chromatography on 400 g. of silica gel eluted with 2.5:1 dichloromethane:ether to yield 3.37 g. (70%) of the cis-isomer, crystallized from cyclohexane, and 0.68 g. (14%) of the trans-isomer, crystallized from cyclohexane and 0.69 g. (14%) of mixed material.

cis-isomer:

M.P.: 79°–80° C.

PMR: $\delta_{CDCl_3}{}^{TMS}$ 2.70 (m, benzylic methylene), 3.26 (m, benzylic methine), 3.93 (bt, J=6 Hz, —OCH$_2$—), 4.28 (m, OH, carbinol methine, with D$_2$O $\delta$4.25, M, carbinol methine), 6.42 (dd, J=8 and 2 Hz, ArH), 6.45 (d, J=2 Hz, ArH), 7.03 (d, J=8 Hz, ArH) and 7.22 (s, PhH).

IR: (CHCl$_3$) 3610, 3333, 1631 and 1603 cm$^{-1}$.

MS: m/e 340 (M+), 322, 190 and 91.

Analysis: Calc'd for C$_{22}$H$_{28}$O$_3$: C, 77.61; H, 8.29% Found: C, 77.46; H, 8.25%.

trans-isomer:

M.P.: 112°–114° C.

PMR: $\delta_{CDCl_3}{}^{TMS}$ 2.68 (m, benzylic methylene), 3.80 (m, OH, —OCH$_2$—, carbinol methine, with D$_2$O $\delta$3.63, m, carbinol methine and $\delta$3.90, bt, J=6 Hz, —OCH$_2$—), 6.32 (bs, overlaps $\delta$6.40), 6.40 (dd, J=8 and 2 Hz, ArH), 7.00 (d, J=8 Hz, ArH) and 7.20 (s, PhH).

IR: (CHCl$_3$) 3610, 3390, 1631 and 1595 cm$^{-1}$.

MS: m/e 340 (M+), 322, 190 and 91.

Analysis: Calc'd for C$_{22}$H$_{28}$O$_3$: C, 77.61; H, 8.29% Found: C, 77.40; H, 8.31%.

In like manner, the following compounds were prepared:

cis-3-[4-(2-Heptyloxy)-2-hydroxyphenyl]cyclohexanol and the trans-isomer as oils from 3-[4-(2-heptyloxy)-2-hydroxyphenyl]cyclohexanone (5.2 g., 13.6 mmole). In order of elution from silica gel, 854 mg. (36%) of the cis-3 and 107 mg. (3%) of the trans-3 isomers are obtained.

cis:

IR: (CHCl$_3$) 3597, 3333, 1629 and 1600 cm$^{-1}$.

MS: m/e 306 (M$^{30}$), 208, 190, 173 and 162.

PMR: $\delta_{CDCl_3}{}^{TMS}$ 0.82 (m, methyl), 2.8 (m, benzylic methine), 3.7 (m, carbinol methine and OH), 4.1 (m, methine), 6.38 (m, ArH) and 6.93 (d, J=8 Hz, ArH).

trans:

MS: m/e 306 (M+), 208 and 190.

PMR: $\delta_{CDCl_3}{}^{TMS}$ 0.82 (m, methyl), 3.25 (m, benzylic methine), 4.3 (m, carbinol methine and OH), 6.33 (m, ArH) and 6.94 (d, J=8 Hz, ArH).

cis-3-[4-(2-Octyloxy)-2-hydroxyphenyl]cyclohexanol and the trans-isomer from 3-[4-(2-octyloxy)-2-hydroxyphenyl]cyclohexanone (2.92 g., 9.18 mmole). In order of elution from silica gel, 1.58 g. (54%) of the cis-3 and 0.57 g. (19%) of the trans-3 isomers are obtained.

cis:

IR: (CHCl$_3$) 3663, 3390, 1637 and 1608 cm$^{-1}$.

MS: m/e 320 (M+), 319, 208 and 190.

PMR: $\delta_{CDCl_3}{}^{TMS}$ 0.83 (m, methyl), 2.81 (m, benzylic methine), 3.8 (m, carbinol methine), 4.1 (m, sidechain methine and OH), 6.35 (m, ArH) and 6.96 (d, J=8 Hz, ArH).

trans:

IR: (CHCl$_3$) 3636, 3390, 1634 and 1595 cm$^{-1}$.

MS: m/e 320 (M+), 235, 208, 190 and 173.

PMR: $\delta_{CDCl_3}{}^{TMS}$ 0.82 (m, methyl), 3.25 (m, benzylic methine), 4.1–4.9 (m, carbinol and sidechain methines and OH), 6.35 (m, ArH) and 6.96 (d, J=8 Hz, ArH).

cis-3-[4-(2-Nonyloxy)-2-hydroxyphenyl]cyclohexanol and the trans-isomer from 3-[4-(2-nonyloxy)-2-hydroxyphenyl]cyclohexanone (3.15 g., 19.48 mmole). In order of elution from silica gel, 2.11 g. (67%) of the cis-3 and 0.32 g. (10%) of the trans-3 isomers as oils are obtained.

Cis:

IR: (CHCl$_3$) 3663, 3390, 1639 and 1610 cm$^{-1}$.

MS: m/e 334 (M+), 316, 208 and 190.

PMR: $\delta_{CDCl_3}^{TMS}$ 0.88 (m, methyl), 2.85 (m, benzylic methine), 3.5-4.1 (m, carbinol methine and OH), 4.22 (m, sidechain methine), 6.38 (m, ArH) and 6.97 (d, J=8 Hz, ArH).

trans:

IR: (CHCl₃) 3636, 3413, 1637 and 1592 cm⁻¹.

MS: m/e 334 (M+), 316, 208, 206 and 190.

PMR: $\delta_{CDCl_3}^{TMS}$ 0.88 (m, methyl), 3.23 (m, benzylic methine), 3.9-4.6 (m, carbinol and sidechain methines and OH), 6.36 (m, ArH) and 6.96 (d, J=8 Hz, ArH).

cis-3-[4-(2-(4-Phenyl)butyloxy)-2-hydroxyphenyl]cyclohexanol and the trans-isomer from 3-[4-(2-(4-phenyl)butyloxy)-2-hydroxyphenyl]cyclohexanone (2.9 g., 8.23 mmole). In order of elution from silica gel, 1.29 g. (44%) of the cis-3 and 241 mg. (8%) of the trans-3 isomers are obtained.

cis:

M.P.: 96°-105° C. (from pentane).

IR: (CHCl₃) 3636, 3390, 1634 and 1608 cm⁻¹.

MS: m/e 340 (M+), 322, 208, 190, 162, 147, 136 and 91.

PMR: $\delta_{CDCl_3}^{TMS}$ 1.30 (d, J=6 Hz, methyl), 3.75 (m, carbinol methine), 4.23 (m, sidechain methine), 6.21 (d, J=2 Hz, ArH), 6.38 (dd, J=8 and 2 Hz, ArH), 6.98 (d, J=8 Hz, ArH) and 7.20 (s, Ph).

Analysis: Calc'd for C₂₂H₂₈O₃: C, 77.61; H, 8.29% Found: C, 77.59; H, 8.18%.

trans:

IR: (CHCl₃) 3623, 3390, 1637 and 1595 cm⁻¹.

MS: m/e 340 (M+), 342, 208, 190, 162, 147, 136 and 91.

PMR: $\delta_{CDCl_3}^{TMS}$ 1.30 (d, J=6 Hz, methyl), 3.3 (m, benzylic methine), 4.23 (m, carbinol and sidechain methines), 6.38 (m, ArH), 6.94 (d, J=8 Hz, ArH) and 7.18 (s, Ph).

cis-3-[4-(2-(6-Phenyl)hexyloxy)-2-hydroxyphenyl]cyclohexanol and the trans-isomer from 3-[4-(2-(6-phenyl)hexyloxy)-2-hydroxyphenyl]cyclohexanone (3.3 g., 9.01 mmole). In order of elution from silica gel, 1.54 g. (46%) of the cis-3 and 274 mg. (8%) of the trans-3 isomers are obtained.

cis:

M.P.: 99°-113° C. (from pentane).

IR: (CHCl₃) 3636, 3367, 1631 and 1592 cm⁻¹.

MS: m/e 368 (M+), 350, 208, 190, 162, 147, 136 and 91.

PMR: $\delta_{CDCl_3}^{TMS}$ 1.30 (d, J=6 Hz, methyl), 3.6 (m, carbinol methine), 4.2 (m, sidechain methine), 6.37 (m, ArH), 6.98 (d, J=8 Hz, ArH) and 7.18 (s, PhH).

Analysis: Calc'd for C₂₄H₃₂O₃: C, 78.22; H, 8.75% Found: C, 78.05; H, 8.56%.

trans:

IR: (CHCl₃) 3636, 3413, 1634 and 1597 cm⁻¹.

MS: m/e 368 (M+), 350, 208, 190, 162, 147, 136 and 91.

PMR: $\delta_{CDCl_3}^{TMS}$ 1.25 (d, J=6 Hz, methyl), 4.21 (m, carbinol and sidechain methines), 6.37 (m, ArH), 6.95 (d, J=8 Hz, ArH) and 7.15 (s, PhH).

EXAMPLE 12

The procedure of Example 1 is repeated but using the appropriate 2-bromo-5-(Z-W-substituted phenol benzyl ether and 2-cycloalken-1-ones as reactants. The following compounds are thus produced:

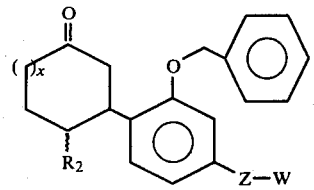

| x | R₂ | Z | W |
|---|----|----|---|
| 0 | H | OCH(CH₃)(CH₂)₃ | C₆H₅ |
| 2 | H | OCH(CH₃)(CH₂)₃ | C₆H₅ |
| 3 | H | OCH(CH₃)(CH₂)₃ | C₆H₅ |
| 0 | H | O(CH₂)₄ | 4-FC₆H₄ |
| 1 | H | O(CH₂)₄ | C₆H₅ |
| 1 | H | O(CH₂)₁₀ | 4-ClC₆H₄ |
| 0 | H | OCH(CH₃)(CH₂)₈ | C₆H₅ |
| 2 | H | OCH(CH₃)CH₂ | 4-FC₆H₄ |
| 1 | H | OC(CH₃)₂(CH₂)₃ | C₆H₅ |
| 3 | H | OCH₂CH(CH₃)CH₂ | C₆H₅ |
| 1 | H | OCH(CH₃)(CH₂)₁₀ | H |
| 0 | H | OC(CH₃)₂(CH₂)₅ | H |
| 3 | H | OC(CH₃)₂(CH₂)₇ | H |
| 1 | H | O(CH₂)₁₃ | H |
| 1 | H | O(CH₂)₁₃ | C₆H₅ |
| 1 | CH₃ | OCH(CH₃)(CH₂)₃ | C₆H₅ |
| 1 | n-C₃H₇ | OCH(CH₃)(CH₂)₃ | C₆H₅ |
| 1 | n-C₆H₁₃ | OCH(CH₃)(CH₂)₃ | C₆H₅ |
| 1 | CH₂C₆H₅ | OCH(CH₃)(CH₂)₃ | C₆H₅ |
| 1 | (CH₂)₄C₆H₅ | OCH(CH₃)(CH₂)₃ | C₆H₅ |
| 0 | C₂H₅ | OCH(CH₃)(CH₂)₆ | 4-FC₆H₄ |
| 0 | (CH₂)₃C₆H₅ | OC(CH₃)₂(CH₂)₁₀ | 4-FC₆H₄ |
| 2 | H | O(CH₂)₄ | C₆H₅ |
| 0 | n-C₄H₉ | O(CH₂)₁₂ | C₆H₅ |
| 2 | CH₃ | OCH(C₂H₅)(CH₂)₃ | 4-ClC₆H₄ |
| 2 | n-C₆H₁₃ | OC(CH₃)₂(CH₂)₆ | H |
| 3 | CH₃ | O(CH₂)₂C(CH₃)₂(CH₂)₂ | H |
| 3 | (CH₂)₂C₆H₅ | O(CH₂)₆ | C₆H₅ |
| 3 | n-C₆H₁₃ | O(CH₂)₁₂ | H |
| 0 | CH₃ | C(CH₃)₂(CH₂)₆ | H |
| 0 | n-C₃H₇ | C(CH₃)₂(CH₂)₆ | H |
| 1 | C₂H₅ | C(CH₃)₂(CH₂)₆ | H |
| 1 | n-C₄H₉ | C(CH₃)₂(CH₂)₆ | H |
| 1 | n-C₆H₁₃ | C(CH₃)₂(CH₂)₆ | H |
| 1 | CH₂C₆H₅ | C(CH₃)₂(CH₂)₆ | H |
| 2 | CH₃ | C(CH₃)₂(CH₂)₆ | H |
| 2 | i-C₃H₇ | C(CH₃)₂(CH₂)₆ | H |
| 2 | CH₂C₆H₅ | C(CH₃)₂(CH₂)₆ | H |
| 2 | (CH₂)₃C₆H₅ | C(CH₃)₂(CH₂)₆ | H |
| 3 | C₂H₅ | C(CH₃)₂(CH₂)₆ | H |
| 3 | n-C₅H₁₁ | C(CH₃)₂(CH₂)₆ | H |
| 3 | (CH₂)₃X₆H₅ | C(CH₃)₂(CH₂)₆ | H |
| 0 | CH₃ | (CH₂)₅ | H |
| 2 | CH₃ | (CH₂)₅ | H |
| 0 | H | (CH₂)₁₃ | H |
| 0 | H | CH₂ | H |
| 0 | CH₃ | (CH₂)₈ | H |
| 1 | CH₃ | (CH₂)₅ | H |
| 1 | n-C₆H₁₃ | (CH₂)₅ | H |
| 2 | CH₂C₆H₅ | (CH₂)₉ | H |
| 3 | i-C₃H₇ | (CH₂)₁₁ | H |
| 0 | CH₃ | (CH₂)₄ | C₆H₅ |
| 0 | H | (CH₂)₅ | C₆H₅ |
| 1 | H | CH(CH₃)(CH₂)₃ | C₆H₅ |
| 1 | CH₃ | CH(CH₃)(CH₂)₃ | C₆H₅ |
| 1 | n-C₄H₉ | CH(CH₃)(CH₂)₃ | C₆H₅ |
| 1 | CH₂C₆H₅ | CH(CH₃)(CH₂)₃ | C₆H₅ |
| 1 | CH₃ | CH(CH₃)(CH₂)₂ | C₆H₅ |
| 3 | CH₃ | CH(CH₃)(CH₂)₂ | C₆H₅ |
| 1 | H | CH(CH₃)CH(CH₃)(CH₂)₅ | H |
| 1 | n-C₆H₁₃ | CH(CH₃)(CH₂)₂ | C₆H₅ |
| 1 | H | CH(CH₃)(CH₂)₃ | 4-FC₆H₄ |
| 2 | H | CH(C₂H₅)(CH₂)₂ | 4-ClC₆H₄ |
| 3 | H | CH(C₂H₅)(CH₂)₄ | 4-FC₆H₄ |
| 0 | H | C(CH₃)₂(CH₂)₂ | H |
| 3 | H | C(CH₃)₂(CH₂)₂ | H |
| 0 | C₂H₅ | C(CH₃)₂(CH₂)₂ | H |
| 0 | H | C(CH₃)₂(CH₂)₁₀ | H |
| 1 | H | C(CH₃)₂(CH₂)₁₀ | C₆H₅ |
| 1 | CH₃ | C(CH₃)₂(CH₂)₁₀ | H |
| 1 | n-C₆H₁₃ | C(CH₃)₂(CH₂)₁₀ | H |
| 1 | CH₂C₆H₅ | C(CH₃)₂(CH₂)₁₀ | H |

-continued

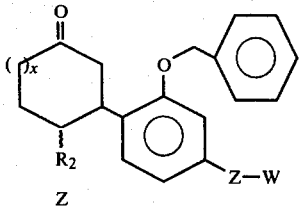

| x | R$_2$ | Z | W |
|---|---|---|---|
| 2 | CH$_3$ | C(CH$_3$)$_2$(CH$_2$)$_{10}$ | H |
| 3 | H | C(CH$_3$)$_2$(CH$_2$)$_{10}$ | H |
| 0 | H | (CH$_2$)$_3$O(CH$_2$)$_3$ | H |
| 1 | H | (CH$_2$)$_3$O(CH$_3$)$_3$ | H |
| 2 | H | (CH$_2$)$_3$O(CH$_2$)$_5$ | H |
| 3 | H | (CH$_2$)$_2$O(CH$_2$)$_8$ | H |
| 1 | H | (CH$_2$)$_6$O(CH$_2$)$_7$ | H |
| 1 | CH$_3$ | (CH$_2$)$_3$O(CH$_2$)$_3$ | H |
| 1 | n-C$_4$H$_9$ | CH$_2$O(CH$_2$)$_7$ | H |
| 1 | CH$_2$C$_6$H$_5$ | (CH$_2$)$_2$O(CH$_2$)$_{10}$ | H |
| 1 | CH$_2$C$_6$H$_5$ | (CH$_2$)$_{10}$O(CH$_2$)$_2$ | H |
| 1 | H | (CH$_2$)$_2$O(CH$_2$)$_{10}$ | H |
| 1 | H | C(CH$_3$)$_2$(CH$_2$)$_2$O(CH$_2$)$_4$ | H |
| 3 | H | (CH$_2$)$_{10}$O(CH$_2$)$_2$ | H |
| 2 | CH$_3$ | (CH$_2$)$_4$OCH$_2$ | C$_6$H$_5$ |
| 0 | CH$_3$ | (CH$_2$)$_6$O | C$_6$H$_5$ |
| 1 | CH$_3$ | (CH$_2$)$_6$O | C$_6$H$_5$ |
| 3 | CH$_3$ | (CH$_2$)$_6$O | C$_6$H$_5$ |
| 0 | CH$_3$ | (CH$_2$)$_6$O | H |
| 1 | CH$_3$ | (CH$_2$)$_6$O | H |
| 2 | CH$_3$ | (CH$_2$)$_6$O | C$_6$H$_5$ |
| 1 | n-C$_6$H$_{13}$ | (CH$_2$)$_6$O | C$_6$H$_5$ |
| 1 | CH$_2$C$_6$H$_5$ | (CH$_2$)$_{13}$O | H |
| 1 | (CH$_2$)$_4$C$_6$H$_5$ | (CH$_2$)$_{13}$O | H |
| 1 | H | (CH$_2$)$_6$O | C$_6$H$_5$ |
| 1 | H | (CH$_2$)$_{13}$O | C$_6$H$_5$ |
| 1 | H | (CH$_2$)$_6$O | 4-FC$_6$H$_4$ |
| 1 | C$_2$H$_5$ | (CH$_2$)$_6$O | 4-FC$_6$H$_4$ |
| 3 | CH$_3$ | (CH$_2$)$_6$O | 4-ClC$_6$H$_4$ |
| 0 | CH$_3$ | (CH$_2$)$_{13}$O | 4-FC$_6$H$_4$ |
| 1 | CH$_3$ | CH(CH$_3$)(CH$_2$)$_2$O | C$_6$H$_5$ |
| 1 | CH$_3$ | CH(CH$_3$)(CH$_2$)$_2$O | C$_6$H$_5$ |
| 1 | (CH$_2$)$_2$C$_6$H$_5$ | CH(CH$_3$)(CH$_2$)$_3$O | C$_6$H$_5$ |
| 0 | C$_2$H$_5$ | CH(CH$_3$)(CH$_2$)$_6$O | H |
| 1 | CH$_3$ | (CH$_2$)$_2$CH(CH$_3$)$_2$CH$_2$ | H |
| 1 | CH$_3$ | CH$_2$C(CH$_3$)$_2$CH$_2$ | H |
| 1 | H | C(CH$_3$)$_2$(CH$_2$)$_4$ | C$_6$H$_5$ |
| 1 | H | CH(CH$_3$)(CH$_2$)$_3$ | 4-pyridyl |
| 0 | H | CH(CH$_3$)(CH$_2$)$_3$ | 4-pyridyl |
| 3 | H | CH(CH$_3$)(CH$_2$)$_3$ | 4-pyridyl |
| 1 | CH$_3$ | (CH$_2$)$_3$ | 2-pyridyl |
| 3 | CH$_3$ | (CH$_2$)$_3$ | 2-pyridyl |
| 0 | C$_2$H$_5$ | (CH$_2$)$_4$ | 4-pyridyl |
| 1 | H | CH(CH$_3$)CH(CH$_3$)CH$_2$ | 3-pyridyl |
| 1 | H | CH(CH$_3$)CH(CH$_3$)CH$_2$ | 4-pyridyl |
| 0 | CH$_3$ | CH(C$_2$H$_5$)(CH$_2$)$_2$ | 4-pyridyl |
| 2 | n-C$_4$H$_9$ | CH(C$_2$H$_5$)(CH$_2$)$_2$ | 4-pyridyl |
| 1 | CH$_2$C$_6$H$_5$ | CH(C$_2$H$_5$)(CH$_2$)$_2$ | 4-pyridyl |
| 3 | H | CH(C$_2$H$_5$)(CH$_2$)$_2$ | 4-pyridyl |
| 1 | CH$_3$ | (CH$_2$)$_{10}$ | 4-pyridyl |
| 3 | H | (CH$_2$)$_{10}$ | 4-pyridyl |
| 1 | t-C$_4$H$_9$ | CH(CH$_3$)(CH$_2$)$_3$ | 4-pyridyl |
| 0 | CH$_3$ | (CH$_2$)$_3$O | 4-pyridyl |
| 2 | H | (CH$_2$)$_3$O | 4-pyridyl |
| 1 | i-C$_3$H$_7$ | (CH$_2$)$_3$O | 4-pyridyl |
| 2 | CH$_2$C$_6$H$_5$ | (CH$_2$)$_3$O | 3-pyridyl |
| 1 | H | (CH$_2$)$_3$OCH(CH$_3$) | 2-pyridyl |
| 1 | n-C$_3$H$_7$ | (CH$_2$)$_3$OCH(CH$_3$) | 2-pyridyl |
| 1 | (CH$_2$)$_3$C$_6$H$_5$ | (CH$_2$)$_3$OCH(CH$_3$) | 2-pyridyl |
| 0 | C$_2$H$_5$ | CH(CH$_3$)(CH$_2$)$_2$O(CH$_2$)$_4$ | 4-pyridyl |
| 0 | CH$_2$C$_6$H$_5$ | CH(CH$_3$)(CH$_2$)$_2$O(CH$_2$)$_4$ | 4-pyridyl |
| 2 | C$_2$H$_5$ | CH(CH$_3$)(CH$_2$)$_2$O(CH$_2$)$_4$ | 4-pyridyl |
| 3 | H | CH(CH$_3$)(CH$_2$)$_2$O(CH$_2$)$_4$ | 4-pyridyl |
| 0 | CH$_3$ | CH(C$_2$H$_5$)(CH$_2$)$_2$OCH(CH$_3$) | 2-pyridyl |
| 1 | H | (CH$_2$)$_4$O(CH$_2$)$_5$ | 4-pyridyl |
| 3 | H | (CH$_2$)$_4$O(CH$_2$)$_5$ | 4-pyridyl |
| 1 | CH$_3$ | (CH$_2$)$_8$O(CH$_2$)$_5$ | 4-pyridyl |
| 2 | H | (CH$_2$)$_8$O(CH$_2$)$_5$ | 4-pyridyl |
| 0 | CH$_3$ | (CH$_2$)$_8$O(CH$_2$)$_5$ | 4-pyridyl |
| 3 | H | (CH$_2$)$_8$O(CH$_2$)$_5$ | 4-pyridyl |
| 0 | H | OCH(CH$_3$)(CH$_2$)$_3$ | 4-pyridyl |
| 1 | CH$_3$ | OCH(CH$_3$)(CH$_2$)$_3$ | 4-pyridyl |

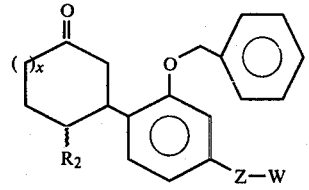

| x | R$_2$ | Z | W |
|---|---|---|---|
| 3 | H | OCH(CH$_3$)(CH$_2$)$_3$ | 4-pyridyl |
| 2 | C$_2$H$_5$ | OCH(CH$_3$)(CH$_2$)$_2$ | 2-pyridyl |
| 1 | n-C$_6$H$_{13}$ | O(CH$_2$)$_2$ | 4-pyridyl |
| 2 | (CH$_2$)$_4$C$_6$H$_5$ | O(CH$_2$)$_2$ | 4-pyridyl |
| 3 | CH$_3$ | O(CH$_2$)$_5$ | 3-pyridyl |
| 1 | n-C$_5$H$_{11}$ | O(CH$_2$)$_5$ | 3-pyridyl |
| 2 | H | OCH(C$_2$H$_5$)(CH$_2$)$_2$ | 4-pyridyl |
| 1 | H | O(CH$_2$)$_{10}$ | 2-pyridyl |
| 2 | H | CH(CH$_3$)CH(CH$_3$)(CH$_2$)$_5$ | H |
| 1 | CH$_3$ | CH(CH$_3$)CH(CH$_3$)(CH$_2$)$_5$ | H |
| 1 | n-C$_3$H$_7$ | CH(CH$_3$)CH(CH$_3$)(CH$_2$)$_5$ | H |
| 2 | CH$_3$ | CH(CH$_3$)CH(CH$_3$)(CH$_2$)$_5$ | H |
| 1 | H | CH(CH$_3$)CH(CH$_3$)(CH$_2$)$_6$ | H |
| 2 | H | CH(CH$_3$)CH(CH$_3$)(CH$_2$)$_6$ | H |
| 1 | H | CH$_2$O(CH$_2$)$_3$ | H |
| 1 | H | CH$_2$O(CH$_2$)$_{12}$ | H |
| 2 | H | CH$_2$O(CH$_2$)$_2$CH(CH$_3$) | C$_6$H$_5$ |
| 0 | H | CH$_2$O(CH$_2$)$_2$ | H |
| 3 | H | CH$_2$O | C$_6$H$_5$ |
| 1 | CH$_3$ | CH$_2$O(CH$_2$)$_5$ | 4-FC$_6$H$_4$ |
| 1 | H | CH(CH$_3$)CH$_2$O(CH$_2$)$_7$ | H |
| 1 | H | CH(CH$_3$)CH$_2$OCH(CH$_3$)CH$_2$ | H |
| 1 | CH$_3$ | CH(CH$_3$)CH$_2$O(CH$_2$)$_6$ | C$_6$H$_5$ |
| 1 | n-C$_3$H$_7$ | CH(CH$_3$)CH$_2$O(CH$_2$) | 4-ClC$_6$H$_4$ |
| 0 | H | CH(CH$_3$)CH$_2$OCH$_2$ | C$_6$H$_5$ |
| 0 | CH$_3$ | CH(CH$_3$)CH$_2$O(CH$_2$)$_{10}$ | H |
| 2 | CH$_3$ | CH(CH$_3$)CH$_2$OCH(CH$_3$)(CH$_2$)$_5$ | H |
| 3 | H | CH(CH$_3$)CH$_2$O(CH$_2$)$_7$ | H |
| 1 | H | CH$_2$CH(CH$_3$)O(CH$_2$)$_7$ | H |
| 3 | H | CH$_2$CH(CH$_3$)O(CH$_2$)$_2$ | 4-pyridyl |
| 2 | H | CH$_2$CH(CH$_3$)OCH(CH$_3$)CH$_2$ | C$_6$H$_5$ |
| 1 | CH$_3$ | CH$_2$CH(CH$_3$)OCH(CH$_3$)(CH$_2$)$_2$ | H |
| 1 | C$_6$H$_5$ | CH(CH$_3$)(CH$_2$)$_3$ | C$_6$H$_5$ |
| 1 | C$_6$H$_5$ | C(CH$_3$)$_2$(CH$_2$)$_6$ | H |
| 0 | C$_6$H$_5$ | CH(CH$_3$)CH(CH$_3$)(CH$_2$)$_5$ | H |
| 2 | C$_2$H$_5$ | C(CH$_3$)$_2$(CH$_2$)$_6$ | H |
| 3 | C$_6$H$_5$ | OCH(CH$_3$)(CH$_2$)$_3$ | C$_6$H$_5$ |
| 1 | C$_6$H$_5$ | (CH$_2$)$_8$O(CH$_2$)$_5$ | 4-pyridyl |
| 1 | CH$_3$ | C(CH$_3$)$_2$(CH$_2$)$_7$ | H |
| 1 | CH$_3$ | CH(CH$_3$)(CH$_2$)$_3$ | C$_6$H$_5$ |
| 1 | n-C$_3$H$_7$ | OCH(CH$_3$)(CH$_2$)$_2$ | 4-FC$_6$H$_4$ |
| 1 | n-C$_6$H$_{13}$ | C(CH$_3$)$_2$CH$_2$ | H |
| 1 | CH$_2$—CH=CH$_2$ | C(CH$_3$)$_2$(CH$_2$)$_7$ | H |
| 1 | CH$_2$CH=CH$_2$ | CH(CH$_3$)(CH$_2$)$_7$ | C$_6$H$_5$ |
| 1 | (CH$_2$)$_4$CH= | OCH$_2$CH$_2$ | C$_6$H$_5$ |
| 1 | CH$_2$CH=CH— | (CH$_2$)$_3$OCH(CH$_3$)CH$_3$ | C$_6$H$_5$ |
| 1 | CH$_2$CH=CH$_2$ | CH(CH$_3$)CH(CH$_3$)CH$_2$ | 4-pyridyl |
| 2 | CH$_2$CH=CH$_2$ | CH(CH$_3$)(CH$_2$)$_3$ | 4-ClC$_6$H$_5$ |
| 2 | (CH$_2$)$_4$CH=CH$_2$ | O(CH$_2$)$_6$ | H |
| 2 | (CH$_2$)$_2$CH=CH$_2$ | (CH$_2$)$_3$O(CH$_2$)$_3$ | H |
| 3 | CH$_2$CH=CH$_2$ | (CH$_2$)$_5$ | H |
| 3 | CH$_2$CH=CH$_2$ | OCH(CH$_3$)(CH$_2$)$_2$ | C$_6$H$_5$ |
| 3 | CH$_2$CH=CH$_2$ | (CH$_2$)$_3$ | 2-pyridyl |

EXAMPLE 13

The benzyl ethers of Example 12 are catalytically hydrogenated according to the procedure of Example 2 to give compounds having the formula shown below wherein each of X, R$_2$, Z and W are as defined in Example 12.

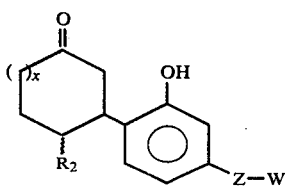

EXAMPLE 14

Chemical, followed by catalytic, reduction of the compounds of Example 12 by the procedure of Example 3 and 4 affords compounds having the formula shown below wherein the variables X, $R_2$, Z and W are as defined in Example 12. The cis- and trans-isomers are produced in each instance.

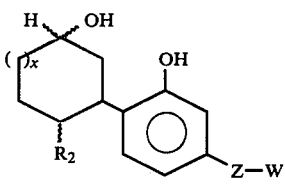

EXAMPLE 15

The compounds listed below are prepared according to the procedure of Example 5 from appropriate 3-alkoxy-2-cycloalkene-1-ones and appropriate 2-benzyloxy-4-(Z-W)-bromobenzenes.

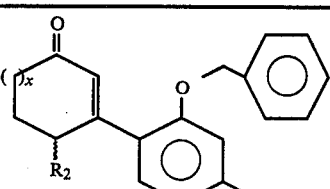

| X | $R_2$ | Z | W |
|---|---|---|---|
| 1 | $C_2H_5$ | $C(CH_3)_2(CH_2)_6$ | H |
| 1 | $i\text{-}C_3H_7$ | $C(CH_3)_2(CH_2)_6$ | H |
| 1 | $n\text{-}C_4H_9$ | $C(CH_3)_2(CH_2)_6$ | H |
| 1 | H | $OCH(CH_3)(CH_2)_3$ | $C_6H_5$ |
| 1 | H | $(CH_2)_5$ | H |
| 1 | $CH_3$ | $(CH_2)_{13}$ | H |
| 1 | $CH_2C_6H_5$ | $O(CH_2)_4$ | $4\text{-}FC_6H_4$ |
| 1 | $(CH_2)_4C_6H_5$ | $O(CH_2)_{10}$ | $4\text{-}ClC_6H_4$ |
| 1 | $n\text{-}C_6H_{13}$ | $OCH(CH_3)(CH_2)_3$ | $4\text{-}FC_6H_4$ |
| 1 | $t\text{-}C_4H_9$ | $(CH_2)_3O(CH_2)_8$ | H |
| 0 | H | $C(CH_3)_2(CH_2)_6$ | H |
| 0 | $CH_3$ | $OCH(CH_3)(CH_2)_3$ | $C_6H_5$ |
| 0 | $n\text{-}C_3H_7$ | $C(CH_3)_2(CH_2)_6$ | H |
| 0 | $n\text{-}C_6H_{13}$ | $(CH_2)_6O$ | $C_6H_5$ |
| 0 | $(CH_2)_2C_6H_5$ | $C(CH_3)_2(CH_2)_2O(CH_2)_4$ | H |
| 0 | $i\text{-}C_3H_7$ | $O(CH_2)_{10}$ | $4\text{-}ClC_6H_4$ |
| 2 | H | $(CH_2)_5$ | H |
| 2 | H | $(CH_2)_{11}$ | H |
| 2 | $CH_3$ | $O(CH_2)_{13}$ | $C_6H_5$ |
| 2 | $C_2H_5$ | $CH(CH_3)(CH_2)_2O$ | $C_6H_5$ |
| 2 | $n\text{-}C_4H_9$ | $OC(CH_3)_2(CH_2)_5$ | H |
| 2 | $CH_2C_6H_5$ | $(CH_2)_6O(CH_2)_7$ | H |
| 2 | $(CH_2)_4C_6H_5$ | $CH(C_2H_5)(CH_2)_2$ | $4\text{-}ClC_6H_4$ |
| 3 | H | $CH(CH_3)(CH_2)_4$ | $C_6H_5$ |
| 3 | $CH_3$ | $OCH(CH_3)(CH_2)_6$ | $4\text{-}FC_6H_4$ |
| 3 | $i\text{-}C_3H_7$ | $(CH_2)_{13}O$ | $C_6H_5$ |
| 3 | $n\text{-}C_5H_{11}$ | $C(CH_3)_2(CH_2)_2$ | H |
| 3 | $(CH_2)_3C_6H_5$ | $(CH_2)_{10}O(CH_2)_2$ | H |
| 1 | $n\text{-}C_5H_{11}$ | $CH(CH_3)(CH_2)_3$ | 4-pyridyl |
| 1 | H | $OCH(CH_3)(CH_2)_3$ | 4-pyridyl |
| 1 | $n\text{-}C_6H_{13}$ | $(CH_2)_{13}$ | 4-pyridyl |

-continued

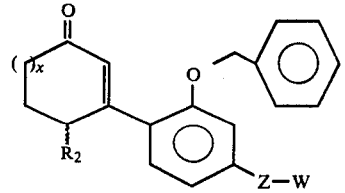

| X | $R_2$ | Z | W |
|---|---|---|---|
| 0 | H | $(CH_2)_6O(CH_2)_7$ | 2-pyridyl |
| 0 | $i\text{-}C_3H_7$ | $CH(CH_3)(CH_2)_3$ | 3-pyridyl |
| 0 | $CH_2C_6H_5$ | $(CH_2)_7$ | 4-pyridyl |
| 2 | H | $(CH_2)_{13}O$ | 4-pyridyl |
| 2 | $(CH_2)_3C_6H_5$ | $(CH_2)_2$ | 4-pyridyl |
| 2 | $i\text{-}C_3H_7$ | $O(CH_2)_8$ | 2-pyridyl |
| 2 | $CH_3$ | $(CH_2)_3O(CH_2)_3$ | 4-pyridyl |
| 3 | H | $(CH_2)_4O$ | 3-pyridyl |
| 3 | $C_2H_5$ | $CH(CH_3)(CH_2)_3$ | 3-pyridyl |
| 3 | $n\text{-}C_6H_{13}$ | $(CH_2)_{13}$ | 4-pyridyl |
| 1 | $CH_2C_6H_5$ | $C(CH_3)_2(CH_2)_6$ | H |
| 1 | $CH_2C_6H_5$ | $OCH(CH_3)(CH_2)_3$ | $C_6H_5$ |
| 1 | $C_6H_5$ | $C(CH_3)_2_2)_6$ | H |
| 0 | $C_6H_5$ | $(CH_2)_5$ | H |
| 1 | $C_6H_5$ | $OCH(CH_3)(CH_2)_3$ | $C_6H_5$ |
| 2 | $C_6H_5$ | $CH(CH_3)(CH_2)_3$ | 4-pyridyl |
| 3 | $C_6H_5$ | $(CH_2)_{13}$ | H |
| 1 | $n\text{-}C_3H_7$ | $C(CH_3)_2(CH_2)_7$ | H |
| 1 | $i\text{-}C_3H_7$ | $C(CH_3)_2(CH_2)_7$ | H |
| 1 | $n\text{-}C_4H_9$ | $CH(CH_3)(CH_2)_3$ | $C_6H_5$ |
| 1 | $i\text{-}C_4H_9$ | $CH(CH_3)(CH_2)_3$ | $4\text{-}FC_6H_4$ |
| 1 | $n\text{-}C_4H_9$ | $(CH_2)_5$ | H |
| 1 | $n\text{-}C_6H_{13}$ | $C(CH_3)_2(CH_2)_6$ | H |
| 1 | $CH_2CH=CH_2$ | $C(CH_3)_2(CH_2)_7$ | H |
| 1 | $CH_2CH=CH_2$ | $CH(CH_3)(CH_2)_3$ | $4\text{-}ClC_6H_4$ |
| 1 | $(CH_2)_3CH=CH_2$ | $OCH(CH_3)(CH_2)_3$ | $C_6H_5$ |
| 1 | $(CH_2)_4CH=CH_2$ | $O(CH_2)_{10}$ | 2-pyridyl |
| 1 | $CH_2CH=CH\text{-}CH_3$ | $O(CH_2)_{13}$ | H |
| 1 | $(CH_2)_2CH=CH\text{-}CH_2CH_3$ | $(CH_2)_5$ | H |
| 1 | $CH_2CH=CH_2$ | $(CH_2)_3OCH_2$ | $C_6H_5$ |
| 1 | $CH_2C_6H_5$ | $C(CH_3)_2(CH_2)_6$ | H |
| 1 | $(CH_2)_4C_6H_5$ | $CH(CH_3)(CH_2)_2$ | $4\text{-}ClC_6H_4$ |
| 2 | $CH_3$ | $C(CH_3)_2(CH_2)_7$ | H |
| 2 | $n\text{-}C_3H_7$ | $CH(CH_3)(CH_2)_3$ | $C_6H_5$ |
| 2 | $n\text{-}C_6H_{13}$ | $C(CH_3)_2(CH_2)_6$ | H |
| 2 | $CH_2CH=CH_2$ | $OCH(CH_3)(CH_2)_3$ | $C_6H_5$ |
| 2 | $(CH_2)_4CH=CH_2$ | $(CH_2)_5$ | H |
| 2 | $CH_2CH=CH_2$ | $(CH_2)_{12}$ | H |
| 2 | $CH_2C_6H_5$ | $CH(CH_3)CH(CH_3)CH_2$ | 3-pyridyl |
| 2 | $(CH_2)_3C_6H_5$ | $(CH_2)_3$ | 2-pyridyl |
| 2 | $n\text{-}C_3H_7$ | $O(CH_2)_2$ | 4-pyridyl |
| 3 | $CH_3$ | $CH(CH_3)(CH_2)_3$ | $C_6H_5$ |
| 3 | $n\text{-}C_3H_7$ | $(CH_2)_6OCH_2$ | $4\text{-}ClC_6H_4$ |
| 3 | $n\text{-}C_5H_{11}$ | $CH(CH_3)CH(CH_3)(CH_2)_5$ | H |
| 3 | $CH_2CH=C(CH_3)_2$ | $OCH_2$ | $C_6H_5$ |
| 3 | $(CH_2)_2C_6H_5$ | $OC(CH_3)_2(CH_2)_5$ | H |

Catalytic hydrogenation of the above compounds according to the procedure of Example 2 affords the corresponding phenolic compounds.

EXAMPLE 16

The procedure of Example 6 is followed but using the appropriate 3-[2-benzyloxy-4-(Z-W)phenyl]cycloalk-2-enone and $(CH_3)_2CuLi$ to produce the following compounds and the corresponding 1,2-addition product.

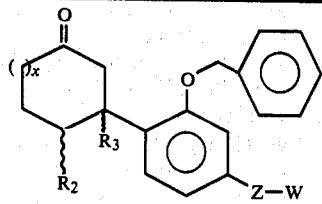

| X | R₂ | R₃ | Z | W |
|---|---|---|---|---|
| 1 | CH₃ | CH₃ | C(CH₃)₂(CH₂)₆ | H |
| 1 | i-C₃H₇ | CH₃ | C(CH₃)₂(CH₂)₆ | H |
| 1 | CH₂C₆H₅ | CH₃ | C(CH₃)₂(CH₂)₆ | H |
| 1 | CH₃ | CH₃ | (CH₂)₁₃ | H |
| 1 | n-C₄H₉ | CH₃ | C(CH₃)₂(CH₂)₆ | H |
| 1 | CH₂C₆H₅ | CH₃ | O(CH₂)₄ | 4-FC₆H₄ |
| 1 | (CH₂)₄C₆H₅ | CH₃ | O(CH₂)₁₀ | 4-ClC₆H₄ |
| 1 | t-C₄H₉ | CH₃ | (CH₂)₃O(CH₂)₈ | H |
| 1 | H | CH₃ | OCH(CH₃)(CH₂)₃ | C₆H₅ |
| 0 | H | CH₃ | C(CH₃)₂(CH₂)₆ | H |
| 0 | CH₃ | CH₃ | OCH(CH₃)(CH₂)₃ | C₆H₅ |
| 0 | n-C₃H₇ | CH₃ | C(CH₃)₂(CH₂)₆ | H |
| 0 | n-C₆H₁₃ | CH₃ | (CH₂)₆ | C₆H₅ |
| 0 | (CH₂)₂C₆H₅ | CH₃ | C(CH₃)₂(CH₂)₂O(CH₂)₄ | H |
| 2 | H | CH₃ | (CH₂)₅ | H |
| 2 | H | CH₃ | (CH₂)₁₁ | H |
| 2 | CH₃ | CH₃ | O(CH₂)₁₃ | C₆H₅ |
| 2 | n-C₄H₉ | CH₃ | OC(CH₃)₂(CH₂)₅ | H |
| 2 | CH₂C₆H₅ | CH₃ | (CH₂)₆O(CH₂)₇ | H |
| 2 | (CH₂)₄C₆H₅ | CH₃ | CH(C₂H₅)(CH₂)₂ | 4-ClC₆H₄ |
| 3 | H | CH₃ | CH(CH₃)(CH₂)₄ | C₆H₅ |
| 3 | CH₃ | CH₃ | OCH(CH₃)(CH₂)₆ | 4-FC₆H₄ |
| 3 | i-C₃H₇ | CH₃ | (CH₂)₁₃O | C₆H₅ |
| 3 | n-C₅H₁₁ | CH₃ | C(CH₃)₂(CH₂)₂ | H |
| 3 | (CH₂)₃C₆H₅ | CH₃ | (CH₂)₁₀O(CH₂)₂ | H |
| 1 | n-C₅H₁₁ | CH₃ | CH(CH₃)(CH₂)₃ | 4-pyridyl |
| 1 | H | CH₃ | OCH(CH₃)(CH₂)₃ | 4-pyridyl |
| 1 | n-C₆H₁₃ | CH₃ | (CH₂)₁₃ | 4-pyridyl |
| 0 | i-C₃H₇ | CH₃ | CH(CH₃)(CH₂)₃ | 3-pyridyl |
| 0 | CH₂C₆H₅ | CH₃ | (CH₂)₇ | 4-pyridyl |
| 2 | (CH₂)₃C₆H₅ | CH₃ | (CH₂)₂ | 4-pyridyl |
| 2 | i-CH₃H₇ | CH₃ | O(CH₂)₈ | 2-pyridyl |
| 3 | H | CH₃ | (CH₂)₄O | 3-pyridyl |
| 3 | n-C₆H₁₃ | CH₃ | (CH₂)₁₃ | 4-pyridyl |
| 1 | CH₂C₆H₅ | CH₃ | OCH(CH₃)(CH₂)₃ | C₆H₅ |
| 1 | C₆H₅ | CH₃ | C(CH₃)₂(CH₂)₆ | H |
| 0 | C₆H₅ | CH₃ | C(CH₃)₂(CH₂)₆ | H |
| 2 | C₆H₅ | CH₃ | OCH(CH₃)(CH₂)₃ | 4-pyridyl |
| 3 | C₆H₅ | CH₃ | CH(CH₃)CH(CH₃)(CH₂)₃ | H |
| 1 | C₆H₅ | CH₃ | O(CH₂)₄ | C₆H₅ |

Catalytic hydrogenation of the above compounds according to the procedure of Example 2 affords the corresponding phenolic compounds.

EXAMPLE 17

3-[4-(1,1-Dimethylheptyl)-2-hydroxyphenyl]-2-cyclohexenol

To a −30° C. solution of 1.00 g. (3.18 mmole) of 3-[4-(1,1-dimethylheptyl)-2-hydroxyphenyl]-2-cyclohexenone in 60 ml. of ether was added dropwise 6.3 ml. of a 1 M (in toluene) diisobutylaluminum hydride solution. The reaction was stirred 30 min. longer at −30° C. and then added to 1.5 l. water. The quenched solution was extracted with three 400 ml. portions of ether and the combined extracts washed twice with 125 ml. of saturated sodium chloride and dried over magnesium sulfate. After evaporation the crude product was purified via column chromatography on 50 g. of florial eluted with ether to yield an oil. Crystallization of the oil from pentane gave 256 mg. (25%) of the title product.

M.P.: 87°–88° C.

MS: m/e 316 (M+), 298, 231 and 213.

PMR: $\delta_{CDCl_3}^{TMS}$ 0.83 (m, terminal methyl), 4.37 (m, carbinol methine), 5.90 (m, vinyl H), 6.37 (b, OH) and 6.87 (m, ArH).

Analysis: Calc'd for $C_{21}H_{32}O_2$: C, 79.70; H, 10.19% Found: C, 79.68; H, 9.96%.

The phenolic compounds of Examples 15 and 16 are reduced according to the procedure of Example 11 to provide the compounds shown below wherein the variables have the meaning given in Examples 15 and 16. The broken line represents a double bond (Example 15 products) in which case R₃ is not present.

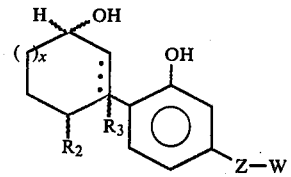

EXAMPLE 18

3-[4-(1,1-Dimethylheptyl)-2-hydroxyphenyl]-3-cyclohexenone ethylene ketal

A solution of 500 mg. (1.59 mmole) of 3-[4-(1,1-dimethylheptyl)-2-hydroxyphenyl]-2-cyclohexenone, 7.8 g. (127 mmole) of ethylene glycol, 375 mg. (3.18 mmole) of hydroquinone and 50 mg. (0.263 mmole) of p-toluenesulfonic acid monohydrate in 50 ml of benzene was heated at reflux for 12 hours using a Dean-Stark condensor filled with 3 A molecular sieves. The reaction was cooled and added to 500 ml. saturated sodium bicarbonate. The quenched mixture was extracted with three 150 ml. portions of ether, dried over magnesium sulfate and evaporated to a solid. This solid was purified via column chromatography on 50 g. of silica gel eluted with 50% etherpetroleum ether to yield (after crystallization from pentane) 393 mg. (69%) of the title product.

M.P.: 97°–98° C.

MS: m/e 358 (M+), 297, 273, 245 and 229.

PMR: $\delta_{CDCl_3}^{TMS}$ 0.88 (m, terminal methyl), 1.29 (s, gem dimethyl), 1.85 (m, methylene), 2.50 (m, two methylenes), 4.03 (s, ethylene ketal), 5.62 (s, OH), 5.84 (m, vinyl H). 6.83 (m, ArH) and 7.02 (d, J=8 Hz, ArH).

Analysis: Calc'd for $C_{23}H_{34}O_3$: C, 77.05; H, 9.56% Found: C, 76.98; H, 9.42%

Repetition of this procedure using the cycloalk-2-enones of Examples 5, 7, 15 and 45, and ethylene, propylene or butylene glycol affords and corresponding cycloalkl-3-enone alkylene ketals of said compounds.

EXAMPLE 19

3-[4-(1,1-Dimethylheptyl)-2-hydroxyphenyl)-4-methyl-cyclohex-3-enone

A mixture of 4.08 g. (0.1 mol.) of 3-[4-(1,1-dimethylheptyl)-2-hydroxyphenyl]-4-methyl-cyclohex-3-enone ethylene ketal, 50 ml. of 2 N oxalic acid and 50 ml. of methanol was stirred at 25° C. for 6 hours. The reaction mixture was added to 500 ml. of water-250 ml. of ether. The ether extract was washed once with 250 ml. of saturated sodium bicarbonate, once with 250 ml. of saturated sodium chloride, dried over magnesium sulfate and evaporated. The residue was purified via column chromatography on 400 g. of silica gel eluted with 50% ether-pentane to yield the title compound.

The remaining ketals of Example 18 are converted to the ketonic form in the like manner.

EXAMPLE 20

3-[4-(1,1-Dimethylheptyl)-2-hydroxyphenyl]-cyclohex-3-ene-1-ol

To a −18° C. solution of 17.5 g (50 mmol) of 3-[4-(1,1-dimethylheptyl)-2-hydroxyphenyl]-cyclohex-3-enone in 50 ml of methanol is added 1.9 g (50 mmol) of sodium borohydride. The reaction mixture is stirred for 30 minutes and then added to 250 ml of saturated sodium chloride-250 ml of ether. The ether extract is washed once with 250 ml of saturated sodium chloride, dried over magnesium sulfate and evaporated. The residue is purified via column chromatography on 400 g of silica gel eluted with 50% ether-pentane to yield the title compound.

Similarly, reduction of the remaining ketones of Example 19 affords the corresponding cycloalk-3-ene-1-ols.

EXAMPLE 21

3-[4-(1,1-Dimethylhexyl)-2-hydroxyphenyl]-cyclohex-2-ene-1-ol

To a −18° C. solution of 70.0 g (0.20 mol) of 3-[4-(1,1-dimethylheptyl)-2-hydroxyphenyl]-cyclohex-2-enone in 200 ml of methanol is added 7.6 g (0.20 mol) of sodium borohydride. The reaction mixture is stirred for 30 minutes and then added to one liter of saturated sodium chloride-one liter of ether. The ether extract is washed once with 500 ml of saturated sodium chloride, dried over magnesium sulfate and evaporated. The residue is purified via column chromatography on 500 g of silica gel eluted with 50% ether-pentane to yield the title compound.

Similarly, reduction of the 3-[4-(Z-W)-2-hydroxyphenyl]cycloalk-2-enones of Examples 7 and 15 affords compounds having the formula

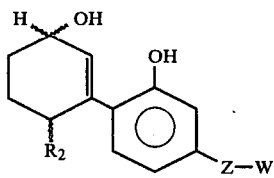

wherein X, $R_2$, Z and W are as defined in said examples.

EXAMPLE 22

The procedure of Examples 18–20 are repeated but using appropriate 3-[4-(Z-W)-2-hydroxyphenyl]-cycloalkyl-2-enones of Examples 15 and 46 to provide compounds having the formula below wherein x, $R_2$, Z and W are as defined therein.

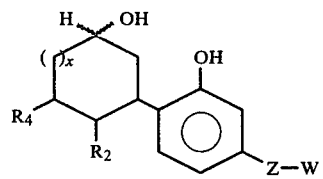

EXAMPLE 23

3-[2-Acetoxy-4-(1,1-dimethylheptyl)phenyl]-cyclohexanone

A solution of 2.0 g of 3-[2-hydroxy-4-(1,1-dimethylheptyl)phenyl]cyclohexanone in 15 ml of pyridine is treated at 10° C. with 10 ml acetic anhydride and the mixture stirred for 18 hours under nitrogen. It is then poured onto ice/water and acidified with dilute hydrochloric acid. The acidified mixture is extracted with ethyl acetate (2×100 ml), the extracts combined, washed with brine and dried ($MgSO_4$). Evaporation under reduced pressure give the title product as an oil.

Similarly, the remaining phenolic compounds of this invention of formula IA–ID are converted to their monoacetoxy esters (of the phenolic hydroxy group) and by substitution of anhydrides of propionic, butyric and valeric acid for acetic anhydride, to the corresponding ester derivatives.

EXAMPLE 24

1-Acetoxy-3-[2-acetoxy-4-(2-(5-phenyl)pentyloxy)-phenyl]cyclohexane

To a solution of 2.0 g of 3-[2-hydroxy-4-(2-(5-phenyl)pentyloxy)phenyl]cyclohexanol in 20 ml of pyridine at 10° C. was added 20 ml of acetic anhydride and the mixture stirred under nitrogen for 18 hours. It is then poured onto ice/water and acidified with dilute hydrochloric acid. The product was isolated by extraction with ethyl acetate (2×100 ml). The combined extracts are washed with brine, dried ($MgSO_4$) and evaporated to give the diacetyl derivative as an oil.

In like manner, the compounds of formulae IA–ID wherein B is hydroxy or hydroxymethyl and $R_1$ is hydrogen are converted to their diacyl derivatives. Replacement of acetic anhydride by propionic, butyric or valeric acid anhydrides affords the corresponding diacyl derivatives.

EXAMPLE 25

3-[2-(4-morpholinobutyryloxy)-4-(1,1-dimethylheptyl)-phenyl]cyclohexanol

Dicyclohexylcarbodiimide (0.227 g, 1.1 mmole) and 4-N-piperidyl-butyric acid hydrochloride (0.222 g, 1.0 mmole) are added to a solution of 3-[2-hydroxy-4-1,1-dimethylheptyl)phenyl]cyclohexanone (0.300 g, 1.0 mmole) in methylene chloride (25 ml) at room temperature. The mixture is stirred for 18 hours and is then cooled to 0° C. and filtered. Evaporation of the filtrate affords the title product as its hydrochloride salt.

Similarly, the reactant of this example and the remaining phenolic compounds of this invention are converted to the basic esters of the phenolic hydroxy group by reaction with the appropriate basic acid reagent. Esters wherein the $R_1$ moiety has the following values are thus prepared:

—$COCH_2NH_2$
—$CO(CH_2)_2N(C_4H_9)_2$
—$CO(CH_2)_2$-N-(methyl)piperazino
—$COC(CH_3)_2(CH_2)_2$-piperidino
—$CO(CH_2)_3N(C_2H_5)_2$
—$COCH(CH_3)(CH_2)_2$-morpholino
—$CO(CH_2)_3$-pyrrolo
—$CO(CH_2)_3$-pyrrolidino
—$COCH_2$-pyrrolo
—$CO(CH_2)_3$-piperidino
—$CO(CH_2)_4NH_2$
—$CO(CH_2)_3NH(C_3H_7)$
—$CO(CH_2)_2$-N-butylpiperazino Careful neutralization of the hydrochloride salts affords the free basic esters which are converted to other acid addition salts according to the procedure of Example 53. In this manner, the hydrobromide, sulfate, acetate, malonate, citrate, glycolate, gluconate, succinate, sulfosalicylate and tartrate salts are prepared.

EXAMPLE 26

3-[2-Hydroxy-4-(1,1-dimethylheptyl)phenyl]-1-methylenecyclohexane

To 50% sodium hydride/mineral oil (2.28 g, 48 mmoles), (washed 3×25 ml portions of pentane) is added 90 ml of dry dimethylsulfoxide and the mixture heated at 70° C. for 0.75 hour. 17.79 g (51 mmoles) of methyl triphenylphosphonium bromide is then added in one portion. The yellow solution is stirred for 30 minutes at 25° C. and then 2.26 g (6.3 mmoles) of 3-[2-acetoxy-4-(1,1-dimethylheptyl)phenyl]cyclohexanone dissolved in 90 ml of dimethylsulfoxide is added all at once and the mixture heated at 63°–65° C. for an additional 1.5 hours. The reaction is then poured onto 150 ml ice water/25 g NaHCO$_3$ and extracted 3×50 ml with ether. The combined ether extracts are dried over MgSO$_4$, decolorized with charcoal and filtered through a bed of silica gel to afford a colorless oil which is chromatographed on 75 g silica gel (eluting solvent cyclohexane). A non-polar impurity is eluted first, then the polarity of the solvent is increased to ether/cyclohexane (1:10) thus affording the title product as a colorless oil.

In like manner, the cycloalkanone and cycloalkenone compounds described herein are converted to their corresponding methylene derivatives.

EXAMPLE 27

3-[2-Hydroxy-4-(1,1-dimethylheptyl)phenyl]-1-hydroxymethylcyclohexane

A solution of 1.03 g of 3-[2-hydroxy-4-(1,1-dimethylheptyl)phenyl]-1-methylenecyclohexane (3 mmoles) dissolved in 25 ml of dry tetrahydrofuran is cooled to 0° C. in an ice/water bath. Borane-tetrahydrofuran complex (4.5 ml, 4.5 mmoles, 1 M solution) is added and the colorless solution allowed to stir overnight at ambient temperature (18 hours). The mixture is cooled in ice and 8 ml of water added to decompose the excess reagent. It is stirred for 15 minutes and then 3 ml (9 mmoles) of 3 N sodium acetate followed by 3 ml 30% hydrogen peroxide added. It is stirred at 0° C. for 15 minutes then allowed to warm to room temperature and stirred overnight (24 hours). The reaction mixture is poured onto 100 ml ice/water and then extracted with 3×50 ml ether. The combined ether extracts are washed with sodium sulfite until negative to starch KI test, dried over MgSO$_4$ and evaporated to dryness to yield a pale yellow oil which is chromatographed on 50 g silica gel (eluting solvent cyclohexane/ether 3:1) to afford the produce as a colorless foam.

Similarly, the remaining methylene cycloalkanones and cycloalkenones of Example 26 are converted to the corresponding hydroxymethyl derivatives.

EXAMPLE 28 trans-4-[2-Benzyloxy-4-(1,1-dimethylheptyl)-phenyl]-3-buten-2-one

A solution of 2-benzyloxy-4-(1,1-dimethylheptyl)benzaldehyde (65.2 g, 0.193 mole) and of 1-triphenylphosphoranylidene-2-propanone (62.0 g, 0.195 mole) in dichloromethane (195 ml) was heated at reflux for 20 hous. Another portion of 15.5 g yield (15.5 g, 0.047 mole) was added and heating at reflux continued for 24 hours. The reaction mixture was cooled, evaporated and diluted with ether. The resulting precipitate of triphenylphosphine oxide was removed by filtration. The crude oil was purified via column chromatography on 1.5 kg of silica gel eluted with 20% etherhexane to yield 53.9 g (74%) of the title compound as an oil.

IR: (CHCl$_3$) 1681, 1621 and 1575 cm$^{-1}$.

MS: (m/e) 378 (M+), 364, 337, 293, 271, 251 and 91.

PMR: $\delta_{CDCl_3}{}^{TMS}$ 0.83 (m, terminal methyl), 1.22 (s, gem dimethyl, 2.32 (S, MeCO), 5.17 (s, benzylic methylene), 6.70 (d, J=16 Hz, vinyl H), 6.95 (m, two ArH), 7.38 (m, Ph and ArH) and 7.90 (d, J=16 Hz, vinyl H).

The remaining 2-benzyloxy-4-(Z-W)benzaldehydes of Preparation Z are reacted in like manner to produce the corresponding compounds having the formula

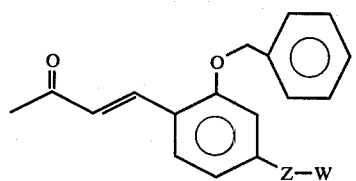

wherein Z and W are as defined in said preparation.

EXAMPLE 29

5-[2-Benzyloxy-4-(1,1-dimethylheptyl)phenyl]-4-carbomethoxy-1,3-cyclohexanedione To a solution of sodium methoxide (0.67 g, 12.4 mmole) and dimethyl malonate (1.86 g, 14.1 mmole) in methanol (4.75 ml) was slowly added a solution of trans-4-[2-benzyloxy-4-(1,1-dimethylheptyl)phenyl]-3-butene-2-one (3.75 g, 9.92 mmole) in methanol (4 ml). The reaction mixture was heated at reflux for 3 hours, then cooled and evaporated under reduced pressure. The residue was diluted with ether and saturated sodium chloride and acidified with 1N hydrochloric acid. The ether extract was washed twice with 500 ml saturated sodium chloride (500 ml), dried over magnesium sulfate and evaporated to 4.71 g (99%) of the title compound.

MP: 108°–109° C. (from petroleum ether-ether).

IR: (CHCl$_3$) 1742, 1709, 1612 and 1577 cm$^{-1}$.

MS: (m/e) 478 (M+), 446, 419, 393, 387 and 91.

PMR: $\delta_{CDCl_3}{}^{TMS}$ 0.82 (m, terminal methyl), 1.19 (s, gem dimethyl), 2.6–3.1 (m), 3.2–4.2 (m), 5.05 (m, benzylic methylene), 5.57 (s, enolic vinyl H), 6.8 (m, ArH) and 7.35 (m, Ph and ArH).

Analysis: Calculated for C$_{30}$H$_{38}$O$_5$: C, 75.28; H, 8.00%. Found: C, 75.05; H, 7.97%.

Repetition of this procedure but using the buten-2-ones of Example 28 affords compounds having the formula shown below wherein Z and W are as defined in Example 28.

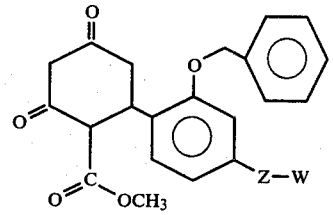

EXAMPLE 30

5-[2-Benzyloxy-4-(1,1-dimethylheptyl)phenyl]-1,3-cyclohexanedione

A mixture of 5-[2-benzyloxy-4-(1,1-dimethylheptyl)-phenyl]-4-carbomethoxy-1,3-cyclohexanedione (20.8 g, 43.5 mmole), dioxane (40 ml) and 20% sodium hydroxide (40 ml) was heated at 100° C. for 2.5 hours. It was cooled in an ice bath and acidified with concentrated hydrochloric acid. This mixture was heated for one hour at 100° C., cooled to 0° C. and then neutralized with sodium bicarbonate. The resultant mixture was added to saturated sodium bicarbonate and ether. The ether extract was dried over magnesium sulfate and evaporated to an oil. Purification of this oil via column chromatography on one kg of silic gel eluted with 10% acetone-ether gave 10.9 g (60%) of the title compound.

MP: 102°–103° C. (from pentane ether).

IR: (CHCl$_3$) 3636–2222 (broad), 1739, 1712, 1613 (broad) and 1577 (shoulder).

MS: m/e 420 (M+), 335, 329 and 91.

PMR: $\delta_{CDCl_3}^{TMS}$ 0.8 (m, terminal methyl), 1.20 (s, gem dimethyl), 2.70 (bdd, J=10 and 8 Hz, methylenes), 3.33 (bs, COCH$_2$CO), 3.6 (m, benzylic methine), 5.0 (s, benzylic methylene), 5.58 (s, enolic vinyl H), 6.8 (m, ArH), 7.22 (bs, Ph) and 8.83 (bs, enolic OH).

Analysis: Calculated for C$_{28}$H$_{36}$O$_3$: C, 79.96; H, 8.63%. Found: C, 79.87; H, 8.54%.

The remaining 4-carbomethoxy cycloalkanediones of Example 29 are decarboxylated in like manner to provide compounds having the formula shown below wherein Z and W are as defined in said example.

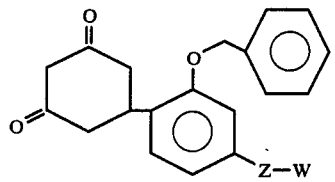

EXAMPLE 31

5-[2-Benzyloxy-4-(1,1-dimethylheptyl)phenyl]-3-methoxy-2-cyclohexene-1-one

A solution of (5.0 g, 11.9 mmole) of 5-[2-benzyloxy-4-(1,1-dimethylheptyl)phenyl]-1,3-cyclohexanedione and p-toluene-sulfonic acid (200 mg) in methanol (250 ml) in a flask connected to a soxhlet condenser containing 3 A molecular sieves was heated at reflux for 30 minutes. The reaction was cooled, concentrated under reduced pressure and the residue diluted with saturated sodium bicarbonate and ether. The ether extract was washed successively with saturated sodium bicarbonate, saturated sodium chloride, dried over magnesium sulfate and evaporated to 5.15 g (99%) of the title compound as an oil.

IR: (CHCl$_3$) 1644, 1612, 1503, 1460 and 1379 cm$^{-1}$.

MS: (m/e) 434 (M+), 349, 343 and 91.

PMR: $\delta_{CDCl_3}^{TMS}$ 0.81 (m, terminal methyl), 1.25 (s, gem dimethyl), 2.49 (d, methylenes), 3.66 (s, OMe), 5.05 (s, vinyl H) and 7.28 (s, Ph).

Similarly, the remaining compounds of Example 30 are transformed to compounds of the formula

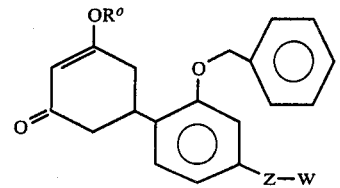

wherein Z and W are as defined in Example 30 and R$^o$ is methyl. Replacement of methanol by ethanol, isobutanol or propanol affords the corresponding alkoxy derivative.

EXAMPLE 32

5-(2-Benzyloxy-4-(1,1-dimethylheptyl)phenyl]-2-cyclohexen-1-one

To a 0° C. solution of the title compound of Example 31, 5-[2-benzyloxy-4-(1,1-dimethylheptyl)phenyl]-3-methoxy-2-cyclohexen-1-one (500 mg, 1.15 mmole), in ether (20 ml) was added lithium aluminum hydride (20 mg, 0.53 mmole). The reaction mixture was stirred for 30 minutes at 0° C., acidified with 1 N hydrochloric acid and stirred for 2 hours at room temperature. The ether phase was removed, washed successively with saturated sodium bicarbonate, saturated sodium chloride, dried over magnesium sulfate and evaporated. The crude oil was purified via column chromatography on 100 g of silica gel eluted with 50% ether-pentane to yield 353 mg (76%) of the title compound as an oil.

IR: (CHCl$_3$) 1681, 1672, 1613, 1575 and 1479 cm$^{-1}$.

MS: (m/e) 404 (M+), 319, 313 and 91.

PMR: $\delta_{CDCl_3}^{TMS}$ 0.86 (m, terminal methyl), 1.30 (s, gem dimethyl), 2.43–2.86 (m, methylenes), 3.70 (m, benzylic methine), 5.07 (s, benzylic methylene), 6.06 (bd, J=5 Hz, vinyl H), 6.8–7.3 (m, ArH and vinyl H) and 7.36 (s, Ph).

By means of this procedure, the remaining compounds of Example 31 are converted to compounds of the formula

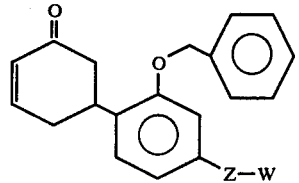

wherein Z and W are as defined in said example.

EXAMPLE 33

5-[2-Benzyloxy-4-(1,1-dimethylheptyl)phenyl]-3-methyl-2-cyclohexen-1-one

To a 0° C. solution of methylmagnesium iodide (11 ml of 2.9 M in ether) and tetrahydrofuran (10 ml) was added dropwise a solution of 5-[2-benzyloxy-4-(1,1-dimethylheptyl)phenyl]-3-methoxy-2-cyclohexen-1-one (3.45 g, 7.95 mmole) in tetrahydrofuran (10 ml). The reaction mixture was then warmed and stirred at room temperature for 2 hours followed by addition to ice cold 1 N hydrochloric acid. After being stirred 20 minutes the hydrolysis mixture was extracted with ether. The ether extract was washed with saturated sodium bicarbonte, saturated sodium chloride, dried over magnesium sulfate and evaporated. The crude product was purified via column chromatography on 100 g of silica gel eluted with 25% ether-pentane to yield 3.08 g (93%) of the title compound.

MP: 60°-61° C. (from pentane).

MS: (m/e) 418 (M+), 333, 327 and 91.

PMR: $\delta_{CDCl_3}^{TMS}$ 0.83 (n, terminal methyl), 1.25 (s, gem dimethyl), 1.96 (s, vinyl methyl), 3.68 (n, benzylic methine), 5.13 (s, benzylic methylene), 5.98 (bs, vinyl H), 6.90 (m, ArH), 7.12 (d, J=8 Hz, ArH) and 7.33 (s, Ph).

In like manner, the following compounds were prepared from appropriate reactants:

5-[2-Benzyloxy-4-(1,1-dimethylheptyl)phenyl]-3-ethyl-2-cyclohexen-1-one (2.83 g, 82%) as an oil from 5-[2-benzyloxy-4-(1,1-dimethylheptyl)phenyl]-3-methoxy-2-cyclohexen-1-one (3.46 g, 7.97 mmole) and 10.8 ml of 2.94 M ethylmagnesium bromide (in ether).

IR: (CHCl₃) 1698, 1666, 1623 and 1582 cm⁻¹.

MS: (m/e) 432 (M+), 341 and 91.

PMR: $\delta_{CDCl_3}^{TMS}$ 0.83 (n, terminal methyl), 1.02 (t, J=7 Hz, methyl), 1.27 (s, gem dimethyl), 2.26 (g, J=7 Hz, methylene of vinyl ethyl), 2.58 (n, two methylenes), 3.65 (n, benzylic methine), 5.12 (s, benzylic methylene), 5.94 (bs, vinyl H), 6.9 (n, ArH), 7.12 (d, J=8 Hz, ArH) and 7.39 (s, Ph). 5-[2-Benzyloxy-4-(1,1-dimethylheptyl)phenyl]-3-n-propyl-2-cyclohexen-1-one (3.48 g, 85%) as an oil from 5-[2-benzyloxy-4-(1,1-dimethylheptyl)phenyl]-3-methoxy-2-cyclohexen-1-one (4.00 g, 9.21 mmole) and n-propylmagnesium bromide (36.8 mmole).

IR: (CHCl₃) 1661, 1631, 1612 and 1575 cm⁻¹.

MS: (m/e) 446 (M+), 335 and 91.

PMR: $\delta_{CDCl_3}^{TMS}$ 0.85 (m, terminal methyl), 0.95 (t, J=7 Hz, methyl of propyl), 1.29 (s, gem dimethyl), 2.22 (m, two methylenes), 2.62 (n, two methylenes), 3.67 (n, benzylic methine), 5.14 (s, benzylic methylene), 5.95 (bs, vinyl H), 6.95 (n, ArH), 7.13 (d, J=8 Hz, ArH) and 7.40 (s, Ph).

5-[2-Benzyloxy-4-(1,1-dimethylheptyl)phenyl]-3-n-hexyl-2-cyclohexene-1-one (4.11 g, 92%) as an oil from 5-[2-benzyloxy-4-(1,1-dimethylheptyl)phenyl]-3-methoxy-2-cyclohexene-1-one (4.00 g, 9.21 mmole) and 7.37 ml of 2.5 M n-hexylmagnesium bromide (in ether).

IR: (CHCl₃) 1678, 1661, 1633, 1618 and 1582 cm⁻¹.

MS: (m/e) 488 (M+), 403, 397 and 91.

PMR: $\delta_{CDCl_3}^{TMS}$ 0.90 (n, two terminal methyls), 1.31 (s, gem dimethyl), 2.28 (n, methylene), 2.61 (n, methylene), 3.70 (n, benzylic methine), 5.20 (s, benzylic methylene), 6.00 (bs, vinyl H), 7.00 (n, ArH), 7.20 (d, J=8 Hz, ArH), and 7.46 (s, Ph).

EXAMPLE 34

Compounds having the formula shown below are prepared from the compounds of Example 32 according to the procedure of Example 33. In the formula Z and W are as defined in Example 32 and R₄ is methyl, ethyl, n-propyl sec-butyl or n-hexyl:

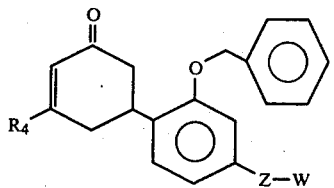

EXAMPLE 35 cis-3-[2-Benzyloxy-4-(1,1-dimethylheptyl)phenyl]-5-methyl-cyclohexanone

A mixture of 5-[2-benzyloxy-4-(1,1-dimethylheptyl)-phenyl]-3-methyl-2-cyclohexen-1-one (1.00 g, 2.39 mmole) and 500 mg of 5% palladium on carbon-50% water was stirred under one atmosphere of hydrogen for one hour. A second 500 mg portion of catalyst was added and stirring continued for 30 minutes. A third 500 mg portion of catalyst was added and stirring continued for 13 minutes. The reaction mixture was then filtered through sodium bicarbonate and magnesium sulfate and the filtrate evaporated. The residue was purified via column chromatography on 140 g of silica gel eluted with 10% ether-petroleum ether to yield 323 mg (32%) of the title compound as an oil.

MS: (m/e) 420 (M+), 402, 363, 335, 329 and 91.

PMR: $\delta_{CDCl_3}^{TMS}$ 0.86 (n, terminal methyl), 1.28 (s, gem dimethyl), 4.06 (C-5 methyl), 3.40 (n, benzylic methine), 5.16 (s, benzylic methylene), 6.95 (d, J=2 Hz, ArH), 6.95 (dd, J=8 and 2 Hz, ArH), 7.43 (s, Ph).

Similarly, the remaining compounds of Examples 33 and 34 are reduced to the corresponding 5-R₄ substituted cyclohexanones.

EXAMPLE 36 cis-3-[4-(1,1-Dimethylheptyl)-2-hydroxyphenyl]-5-methyl-cyclohexanone

A mixture of 5-[2-benzyloxy-4-(1,1-dimethyl)heptyl)-phenyl]-3-methyl-2-cyclohexen-1-one (2.83 g, 6.77 mmole), 1.5 g of 5% palladium on carbon-50% water and sodium bicarbonate (2.8 g) in methanol (30 ml) was stirred under one atmosphere of hydrogen for 45 minutes. The reaction mixture was filtered through diatomaceous earth and the filtrate evaporated under reduced pressure. The residue was dissolved in ether, dried with magnesium sulfate and evaporated. Crystallization of the residue with pentane gave 1.15 g (52%) of the title compound.

MP: 95°-98° C.

PMR: $\delta_{CDCl_3}^{TMS}$ 0.87 (n, terminal methyl), 1.1 (C-5 methyl), 1.28 (s, gem dimethyl), 3.25 (n, benzylic methine), 5.62 (s, OH), 6.85 (m, ArH), 7.10 (d, J=8 Hz, ArH).

Analysis: Calculated for $C_{22}H_{34}O_2$: C, 79.95; H, 10.37%. Found: C, 80.22; H, 10.28%.

Following the above procedure, the compounds listed below were prepared from appropriate reactants of Examples 33 and 34.

cis-3-[4-(1,1-Dimethylheptyl)-2-hydroxyphenyl]-5-ethylcyclohexanone (1.34 g, 60%) from 5-[2-benzyloxy-4-(1,1-dimethylheptyl)phenyl]-3-ethyl-2-cyclohexen-1-one (2.83 g, 6.55 mmole).

MP: 106°-107° C.

IR: (CHCl₃) 3597, 3333, 1709, 1626 and 1585 cm⁻¹.

MS: (m/e) 344 (M+), 326, 315, 297, 273 and 259.

PMR: $\delta_{CDCl_3}^{TMS}$ 0.83 (n, terminal methyl), 0.95 (t, J=7 Hz, methyl), 1.25 (s, gem dimethyl), 3.25 (n, benzylic methine), 5.98 (s, OH), 6.90 (n, ArH) and 7.16 (d, J=8 Hz, ArH).

Analysis: Calculated for $C_{23}H_{36}O_2$: C, 80.18; H, 10.53%. Found: C, 80.27; H, 10.39%.

cis-3[4-(1,1-Dimethylheptyl)-2-hydroxyphenyl]-5-propylcyclohexanone (1.66 g, 61%) from 5-[2-benzyloxy-4-(1,1-dimethylheptyl)phenyl]-3-propyl-2-cyclohexen-1-one (3.40 g, 7.62 mmole).

MP: 86.5°–90.5° C.
IR: (CHCl$_3$) 3533, 3289, 1700, 1618 and 1577 cm$^{-1}$.
MS: (m/e) 358 (M+), 340, 315, 297 and 273.
PMR: $\delta_{CDCl_3}{}^{TMS}$ 0.90 (n, terminal methyls), 1.22 (s, gem dimethyl, 3.25 (n, benzylic methine), 5.95 (s, CH), 6.85 (n, ArH) and 7.14 (d, J=8 Hz, ArH).
Analysis: Calculated for C$_{24}$H$_{38}$O$_2$: C, 80.39; H, 10.68%. Found: C, 80.16; H, 10.57%.

cis-3-[4-(1,1-Dimethylheptyl)-2-hydroxyphenyl]-5-hexylcyclohexanone (3.06 g, 93%) from 5-[2-benzyloxy-4-(1,1-dimethylheptyl)phenyl]-3-hexyl-2-cyclohexen-1-one (4.00 g, 8.2 mmole).
MP: 84°–85° C. (from pentane).
IR: (CHCl$_3$) 3571, 3333, 1703, 1623 and 1582 cm$^{-1}$.
MS: (m/e) 400 (M+), 382 and 315.
PMR: $\delta_{CDCl_3}{}^{TMS}$ 0.90 (n, terminal methyls), 1.21 (s, gem dimethyl) 3.20 (n, benzylic methine), 5.80 (s, OH), 6.85 (n, ArH) and 7.10 (d, J=8 Hz).
Analysis: Calculated for C$_{27}$H$_{44}$O$_2$: C, 80.94; H, 11.07%. Found: C, 80.97; H, 10.94%.

EXAMPLE 37

The compounds of Example 34 are catalytically hydrogenated according to the procedure of Example 36 to give the products shown below wherein Z, W and R$_4$ are as defined in Example 34.

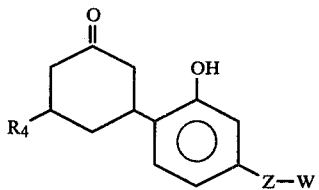

EXAMPLE 38 trans-3-[2-Benzyloxy-4-(1,1-dimethylheptyl)-phenyl]-5-methyl-cyclohexanone

To a 0° C. solution of dimethyl copper lithium (2.47 mmole) in ether (3 ml) and hexane (2 ml) was added dropwise a solution of 5-[2-benzyloxy-4-(1,1-dimethylheptyl)phenyl]-2-cyclohexen-1-one (500 mg, 1.24 mmole) in ether (1.5 ml). The reaction mixture was stirred for 15 minutes and then poured into saturated aqueous ammonium cloride (300 ml). The quenched reaction was extracted with three 50 ml portions of ether, the combined ether extracts washed with water, saturated sodium chloride, dried over magnesium sulfate and evaporated to yield 475 mg (92%) of the title compound as an oil.
IR: (CHCl$_3$) 1704, 1613 and 1577 cm$^{-1}$.
MS: (m/e) 420 (M+), 402, 363, 335 and 329.
PMR: $\delta_{CDCl_3}{}^{TMS}$ 0.85 (n, terminal methyl), 0.96 (d, J=6 Hz, C-5 methyl), 1.22 (s, gem dimethyl), 3.76 (n, benzylic methine), 5.08 (s, benzylic methylene), 6.72–7.05 (m, ArH) and 7.33 (bs, Ph).

EXAMPLE 39 trans-3-[4-(1,1-Dimethylheptyl)-2-hydroxyphenyl]-5-methyl-cyclohexanone

A mixture of trans-3-[2-benzyloxy-4-(1,1-dimethylheptyl)phenyl]-5-methylcyclohexanone (175 mg, 0.417 mmole) and 175 mg of 5% palladium on carbon-50% water in methanol (8 ml) was stirred under one atmosphere of hydrogen gas until hydrogen uptake ceased. The reaction mixture was filtered through diatomaceous earth and the filtrate evaporated under reduced pressure. Crystallization of the residue in pentane gave 89 mg (64%) of the title compound.
MP: 99°–102° C.
MS: m/e 330 (M+), 312, 273 and 245.

EXAMPLE 40 cis-3-[2-Benzyloxy-4-(1,1-dimethylheptyl)phenyl]-trans-5-methylcyclohexanol and the trans, cis isomer To a −78° C. solution of trans-3-[2-benzyloxy-4-(1,1-dimethylheptyl)phenyl]-5-methylcyclohexanone (300 mg, 10.714 mmole) in methanol (15 ml) - tetrahydrofuran (5 ml) was added sodium borohydride (216 mg, 5.68 mmole) during a one hour period. The reaction mixture was stirred for 2 hours longer at −78° C., warmed to room temperature and evaporated in vacuo. The residue was acidified with dilute hydrochloric acid and extracted with ether. The extract was dried over magnesium sulfate, evaporated and the residue purified via column chromatography on 50 g of silica gel eluted with 30% ether-pentane to yield in order of elution 232 mg (77%) of the trans, cis isomer and 45.9 mg (15%) of the cis, trans isomer.

trans, cis:
MS: (m/e) 422 (M+), 337, 314, 229 and 91.
PMR: $\delta_{CDCl_3}{}^{TMS}$ 0.86 (n, terminal methyl), 1.05 (d, J=7 Hz, C-5 methyl), 1.26 (s, gem dimethyl), 3.70 (n, benzylic methine), 4.05 (n, carbinol methine), 5.13 (s, benzylic methylene), 6.8–7.0 (n, ArH) and 7.1–7.6 (n, ArH and Ph).

cis trans:
MS: (m/e) 422 (M+), 337, 314, 229, 206 and 91.
PMR: $\delta_{CDCl_3}{}^{TMS}$ 0.9 (n, terminal methyl), 1.05 (d, J=7 Hz, C-5 methyl), 3.1–4.3 (n, benzylic and carbinol methines), 5.13 (s, benzylic methylene), 5.40 (s, OH) and 6.8–7.7 (n, Ph and ArH).

EXAMPLE 41 cis-3-[2-Benzyloxy-4-(1,1-dimethylheptyl)phenyl]-cis-5-methylcyclohexanol and the trans, trans isomer To a −78° C. solution of cis-3-[2-benzyloxy-4-(1,1-dimethylheptyl)phenyl]-5-methylcyclohexanone (228 mg, 0.543 mmole) in methanol (10 ml) was added sodium borohydride (160 mg, 4.21 mmole) over a 2 hour period. The reaction mixture was allowed to warm to room temperature and was then added to ether-saturated sodium chloride. The ether extract was dried over magnesium sulfate and evaporated under reduced pressure. The residue was purified via preparative layer chromatography on five 20 cm×20 cm×0.5 mm silica gel plates eluted with 50% ether-pentane to yield 36 mg (16%) of the trans, trans isomer (R$_f$0.25, silica gel, 33% ether-petroleum ether) and 168 mg (R$_f$0.17, silica gel, 33% ether-petroleum ether) of the cis, cis isomer.

EXAMPLE 42 cis-3-[4-1,1-Dimethylheptyl)-2-hydroxyphenyl]-cis-5-methylcyclohexanol

To a −78° C. solution of cis-3-[4-(1,1-dimethylheptyl)-2-hydroxyphenyl]-5-methylcyclohexanone (896 mg, 2.13 mmole) in methanol (30 ml) is added sodium borohydride (805 mg, 21.8 mmole). The reaction mixture was stirred for one hour at −78° C., warmed to room temperature and added to ether and saturated sodium chloride. The ether extract was dried over magnesium sulfate and evaporated to yield an oil. Crystallization from pentane yields 589 mg (65%) of the title compound:
MP: 113°–114° C.
IR: (CHCl$_3$) 3636, 3390, 1631 and 1592 cm$^{-1}$.
MS: (m/e) 332 (M+), 314, 247, 229 and 95.
PMR: $\delta_{CDCl_3}{}^{TMS}$ (m, C-5 and terminal methyl), 1.21 (s, gem dimethyl), 2.95 (n, benzylic methine), 3.82 (n, carbinol methine), 5.62 (s, OH), 6.82 (n, ArH) and 7.12 (d, J=8 Hz, ArH).
Analysis: Calculated for C$_{22}$H$_{36}$O$_2$: C, 79.46; H, 10.91%. Found: C, 79.79; H, 10.62%.
The following compounds were prepared from appropriate reactants in like manner:
cis-3-[4-(1,1-Dimethylheptyl)-2-hydroxyphenyl]-cis-5-ethylcyclohexanol (0.74 g, 74%) from cis-3-[4-(1,1-dimethylheptyl)-2-hydroxyphenyl]-5-ethylcyclohexanone (1.00 g, 2.30 mmole).
MP: 110°–111° C.
IR: (CHCl$_3$) 3636, 3367, 1631 and 1587 cm$^{-1}$.
PMR: $\delta_{CDCl_3}{}^{TMS}$ 0.90 (n, terminal methyls), 1.22 (s, gem dimethyls), 2.95 (n, benzylic methine), 3.85 (n, carbinol methine), 5.59 (s, OH), 6.85 (n, ArH) and 7.10 (d, J=8 Hz, ArH).
Analysis: Calculated for C$_{23}$H$_{38}$O$_2$: C, 79.71; H, 11.05%. Found: C, 79.41; H, 10.71%.
cis-3-[4-(1,1-Dimethylheptyl)-2-hydroxyphenyl]-cis-5-n-propylcyclohexanol (0.954 g, 71%) from cis-3-[4-(1,1-dimethylheptyl)-2-hydroxyphenyl]-5-n-propylcyclohexanone (1.34 g, 3.74 mmole).
MP: 103°–104° C. (from pentane).
IR: (CHCl$_3$) 3636, 3378, 1626 and 1587 cm$^{-1}$.
MS: (m/e) 360 (M+), 342, 275, 257 and 161.
PMR: $\delta_{CDCl_3}{}^{TMS}$ 0.90 (n, terminal methyls), 1.22 (s, gem dimethyls), 2.95 (n, benzylic methine), 3.82 (n, carbinol methine), 5.42 (s, OH), 6.85 (n, ArH) and 7.08 (d, J=8 Hz, ArH).
Analysis: Calculated for C$_{24}$H$_{40}$O$_2$: C, 79.94; H, 11.18%. Found: C, 79.88; H, 11.22%.
cis-3-[4-(1,1-Dimethylheptyl)-2-hydroxyphenyl]-cis-5-n-hexylcyclohexanol, after purification on 120 g of silica gel eluted with 50% ether-pentane, a quantitative yield as an oil containing a trace of the trans, trans isomer, cis-3-[4-(1,1-dimethylheptyl)-2-hydroxyphenyl]-5-n-hexylcyclohexanone (1.20 g, 3.00 mmole).
IR: (CHCl$_3$) 3623, 3355, 1626 and 1585 cm$^{-1}$.
MS: (m/e) 402 (M+), 384, 317 and 299.
PMR: $\delta_{CDCl_3}{}^{TMS}$ 0.90 (n, terminal methyls), 1.22 (s, gem dimethyls), 2.97 (n, benzylic methine), 3.85 (n, carbinol methine), 4.32 (n, carbinol methine of trans, trans isomer), 5.58 (bs, OH), 6.85 (n, ArH) and 7.09 (d, J=8 Hz, ArN).

EXAMPLE 43 trans-3-[4-(1,1-Dimethylheptyl)-2-hydroxyphenyl]-cis-5-methylcyclohexanol

A mixture of trans-3-[2-benzyloxy-4-(1,1-dimethylheptyl)phenyl]-cis-5-methylcyclohexanol (220 mg, 0.521 mmole) and 220 mg of 5% palladium on carbon-50% water in methanol (8 ml) was stirred under one atmosphere of hydrogen for 3 hours. The reaction mixture was filtered through diatomaceous earth and the filtrate evaporated. Crystallization of the residue with petroleum ether gave 91 mg (53%) of the title compound.
MP: 111°–112° C.
IR: (CHCl$_3$) 3571, 3333, 1629 and 1572 cm$^{-1}$.
MS: (m/e) 332 (M+), 314, 246 and 229.
PMR: $\delta_{CDCl_3}{}^{TMS}$ 0.85 (n, terminal methyl), 1.13 (d, J=7 Hz, C-5 methyl), 1.26 (s, gem dimethyl), 3.55 (n, benzylic methine), 4.15 (n, carbinol methine), 5.90 (bs, OH), 6.90 (n, ArH) and 7.20 (d, J=8 Hz, ArH).
Similarly, the following compounds were prepared in like manner from appropriate reactants:
cis-3-[4-(1,1-Dimethylheptyl)-2-hydroxyphenyl]-trans-5-methylcyclohexanol (20.0 mg, 56%) as an oil from cis-3-[2-benzyloxy-4-(1,1-dimethylheptyl)phenyl]-trans-5-methylcyclohexanol (45 mg, 0.107 mmole) as an oil.
High resolution MS: (m/e) 332.2698 (M+, C$_{22}$H$_{36}$O$_2$), 314.2635, 247.1657 and 229.1600.
trans-3-[4-(1,1-Dimethylheptyl)-2-hydroxypehnyl]-trans-5-methylcyclohexanol (28 mg quantitative yield) from trans-3-[2-benzyloxy-4-(1,1-dimethylheptyl)-phenyl]-trans-5-methylcyclohexanol (36 mg, 0.0853 mmole) gives the product as an oil.
R$_f$=0.35 (silica gel, 50% ether-pentane).
cis-3-[4-(1,1-Dimethylheptyl)-2-hydroxyphenyl]-cis-5-methylcyclohexanol in quantititative yield from cis-3-[2-benzyloxy-4-(1,1-dimethylheptyl)phenyl]-cis-5-methylcyclohexanol (168 mg, 0.398 mmole). It was identical to the product of Example 42.

EXAMPLE 44

3-[2-Benzyloxy-4-(Z-W)phenyl]-5-R$_4$-cycloheptenones and cyclooctenones

Following the procedure of Example 5, the compounds tabulated below are prepared from appropriate 3-alkoxy-2-cycloalken-1-ones and 2-bromo-5-(Z-W)phenol benzyl ethers:

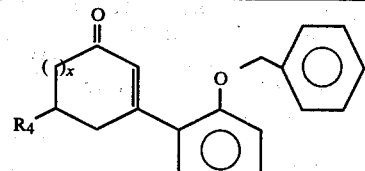

| X | R$_4$ | Z | W | X | R$_4$ | Z | W |
|---|---|---|---|---|---|---|---|
| 2 | CH$_3$ | C(CH$_3$)$_2$(CH$_2$)$_6$ | H | 2 | C$_2$H$_5$ | O(CH$_2$)$_4$ | C$_6$H$_5$ |
| 2 | C$_2$H$_5$ | C(CH$_3$)$_2$(CH$_2$)$_6$ | H | 2 | i-C$_3$H$_7$ | O(CH$_2$)$_{13}$ | H |
| 2 | n-C$_6$H$_{13}$ | C(CH$_3$)$_2$(CH$_2$)$_6$ | H | 2 | CH$_3$ | O(CH$_2$)$_{10}$ | 4-ClC$_6$H$_4$ |
| 2 | i-C$_3$H$_7$ | C(CH$_3$)$_2$(CH$_2$)$_6$ | H | 2 | CH$_3$ | OCH(CH$_3$)$_3$(CH$_2$)$_6$ | 4-FC$_6$H$_4$ |
| 2 | CH$_3$ | CH$_2$ | H | 2 | n-C$_5$H$_{11}$ | OC(CH$_3$)(CH$_2$)$_2$ | C$_6$H$_5$ |
| 2 | n-C$_3$H$_7$ | (CH$_2$)$_5$ | H | 2 | CH$_3$ | CH(CH$_3$)(CH$_2$)$_3$ | 4-pyridyl |
| 2 | n-C$_5$H$_{11}$ | CH(CH$_3$)(CH$_2$)$_3$ | C$_6$H$_5$ | 2 | CH$_3$ | (CH$_2$)$_{10}$ | 4-pyridyl |
| 2 | CH$_3$ | (CH$_2$)$_{11}$ | | 2 | C$_2$H$_5$ | (CH$_2$)$_3$ | 2-pyridyl |

-continued

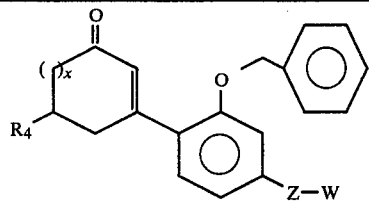

| X | R4 | Z | W | X | R4 | Z-W | W |
|---|---|---|---|---|---|---|---|
| 2 | C₂H₅ | (CH₂)₁₃ | H | 2 | n-C₄H₉ | (CH₂)₆O | C₆H₅ |
| 2 | CH₃ | CH(CH₃)CH(CH₃)(CH₂)₅ | H | 2 | i-C₄H₉ | (CH₂)₆O | 4-FC₆H₄ |
| 2 | n-C₄H₉ | C(CH₃)₂ | CH₃ | 2 | CH₃ | (CH₂)₁₃O | 4-FC₆H₄ |
| 2 | C₆H₅ | C(CH₃)₂(CH₂)₇ | H | 2 | n-C₅H₁₁ | (CH₂)₆OCH₂ | 4-ClC₆H₄ |
| 2 | n-C₆H₁₃ | C(CH₃)₂(CH₂)₃ | H | 2 | CH₃ | (CH₂)₄O(CH₂)₅ | 4-pyridyl |
| 2 | CH₃ | OCH(CH₃)(CH₂)₃ | C₆H₅ | 2 | CH₃ | (CH₂)₈O(CH₂)₅ | 4-pyridyl |
| 3 | CH₃ | C(CH₃)₂(CH₂)₆ | H | | | | |
| 3 | C₂H₅ | C(CH₃)₂(CH₂)₆ | H | | | | |
| 3 | n-C₅H₁₁ | C(CH₃)₂(CH₂)₆ | H | | | | |
| 3 | i-C₃H₇ | C(CH₃)₂(CH₂)₆ | H | | | | |
| 3 | CH₃ | C(CH₃)₂(CH₂)₇ | H | | | | |
| 3 | n-C₃H₇ | C(CH₃)₂(CH₂)₇ | H | | | | |
| 3 | n-C₆H₁₃ | CH(CH₃)(CH₂)₄ | H | | | | |
| 3 | CH₃ | (CH₂)₅ | H | | | | |
| 3 | i-C₃H₇ | (CH₂)₅ | H | | | | |
| 3 | n-C₆H₁₃ | (CH₂)₉ | H | | | | |
| 3 | CH₃ | (CH₂)₁₃ | H | | | | |
| 3 | C₂H₅ | CH(CH₃)(CH₂)₂ | C₆H₅ | | | | |
| 3 | CH₃ | CH(CH₃)(CH₂)₃ | 4-FC₆H₄ | | | | |
| 3 | CH₃ | CH(C₂H₅)(CH₂)₂ | 4-ClC₆H₄ | | | | |
| 3 | CH₃ | OCH(CH₃)(CH₂)₃ | C₆H₅ | | | | |
| 3 | CH₃ | OCH(CH₃)(CH₂)₆ | 4-FC₆H₄ | | | | |
| 3 | C₂H₅ | O(CH₂)₄ | C₆H₅ | | | | |
| 3 | CH₃ | O(CH₂)₁₀ | 4-ClC₆H₄ | | | | |
| 3 | n-C₄H₉ | OCH(CH₃)(CH₂)₃ | 4-pyridyl | | | | |
| 3 | CH₃ | O(CH₂)₅ | 3-pyridyl | | | | |
| 3 | CH₃ | CH₂O(CH₂)₅ | 4-FC₆H₄ | | | | |
| 3 | C₂H₅ | CH(CH₃)CH₂OCH₂ | 4-ClC₆H₄ | | | | |
| 3 | n-C₅H₁₁ | (CH₂)₈O(CH₂)₅ | 4-pyridyl | | | | |
| 3 | CH₃ | (CH₂)₃ | 2-pyridyl | | | | |
| 3 | CH₃ | (CH₂)₃O | 4-pyridyl | | | | |

Catalytic hydrogenation of the above compounds according to the procedure of Example 2 affords the corresponding phenolic compounds.

EXAMPLE 45 trans-3-[4-(1,1-Dimethylheptyl)-2-hydroxyphenyl]-cis-4-(2-propenyl)cyclohexanol

A solution of trans-3-[2-benzyloxy-4-(1,1-dimethylheptyl)phenyl]-cis-4-(2-propenyl)cyclohexanol (900 mg, 2.01 mmole) and 2.74 ml of 2.2 M n-butyllithium (in hexane) in ether (3 ml) was stirred for 2 days at room temperature. A second 2.0 mmole portion of n-butyllithium was added and the reaction mixture stirred for another 2 days. The reaction mixture was added to saturated ammonium chloride (250 ml) and the mixture extracted with ether. The ether extract was dried over magnesium sulfate and evaporated. The residue was purified via column chromatography on 20 g of silica gel eluted with 50% ether-pentane to yield 631 mg (88%) of the title compound:

MP: 85°–91° C.
IR: (CHCl₃) 3311, 1639, 1618 and 1567 cm$^{-1}$.
MS: (m/e) 358 (M+), 343, 340, 316, 299, 273 and 255.
PMR: $\delta_{CDCl_3}^{TMS}$ 0.82 (n, terminal methyl), 1.28 (s, gem dimethyl), 3.02 (n, benzylic methine), 4.23 (n, carbinol methine), 4.6–5.0 and 5.4–6.0 (n, vinyl H), 6.81 (d, J=2 Hz, ArH), 6.82 (dd, J=8 and 2 Hz, ArH) and 7.05 (d, J=8 Hz, ArH).

By means of this procedure is prepared:
cis-3-[4-(1,1-Dimethylhepty)-2-hydroxyphenyl]-trans-4-(2-propenyl)cyclohexanol (241 mg, 60%) from cis-3-[2-benzyloxy-4-(1,1-dimethylheptyl)phenyl]-trans-4-(2-propenyl)cyclohexanol (500 mg, 1.12 mmole).

MP: 124°–125° C. (from pentane).
IR: (CHCl₃) 3571, 3333, 1642, 1618 and 1580.
MS: (m/e) 358 (M+), 340, 298, 286, 273 and 255.
PMR: $\delta_{CDCl_3}^{TMS}$ 0.83 (n, terminal methyl), 1.23 (s, gem dimethyl), 3.70 (n, carbinol methine), 4.6–5.1 and 5.2–6.0 (n, vinyl H), 6.70 (d, J=2 Hz, ArH), 6.82 (dd, J=8 and 2 Hz, ArH) and 7.05 (d, J=8 Hz, ArH).

Analysis: Calculated for C₂₄H₃₈O₂: C, 80.39; H, 10.68%. Found: C, 80.52; H, 10.57%.

EXAMPLE 46 trans-3-[4-(1,1-Dimethylheptyl)-2-hydroxyphenyl]-4-(2-propenyl)cyclohexanone

To a solution of 3-[4-(1,1-dimethylheptyl)-2-hydroxyphenyl]-4-(2-propenyl)cyclohexanol (2.15 g, 6.03 mmole) (mixture of isomers) in dichloromethane (15 ml) was added pyridinium chlorochromate (2.59 g, 12.1 mmole). The reaction mixture was stirred for 2 hours at room temperature, diluted with ether, diatomaceous earth added and the mixture filtered through magnesium sulfate. The evaporated filtrate was purified via column chromatography on 200 g of silica gel eluted with 20% ether-pentane to yield 250 mg of crude title compound. This was further purified via preparative layer chromatography on two 20 cm×20 cm×2 mm silica gel plates eluted twice with 20% ether-pentane to yield 200 mg (9.3%) of the title compound as an oil.

IR: (CHCl$_3$) 3571, 3390, 1718, 1650, 1626 and 1577 cm$^{-1}$.

MS: (m/e) 356 (M+), 341, 338, 314, 288, 271, 257, 253 and 229.

PMR: $\delta_{CDCl_3}{}^{TMS}$ 0.79 (n, terminal methyl), 1.22 (s, gem dimethyl), 4.8–5.2 and 5.4–6.1 (n, vinyl H), 6.7 (n, ArH) and 6.82 (d, J=8 Hz, ArH).

Analysis: Calculated for C$_{24}$H$_{36}$O$_2$: C, 80.85; H, 10.18%. Found: C, 80.92; H, 9.86%.

EXAMPLE 47 trans-3-[2-Benzyloxy-4-(1,1-dimethylheptyl)phenyl]-4-(2-(propenyl)-cyclohexanone ethylene ketal A mixture of trans-3-[2-benzyloxy-4-(1,1-dimethylheptyl)phenyl]-4-(2-propenyl)cyclohexanone (17.0 g, 38.1 mmole), ethylene glycol (47.2 g, 0.762 mole) and p-toluenesulfonic acid monohydrate (250 mg) in benzene (200 ml) was heated at reflux for 3 hours with a Dean-Stark trap. The reaction mixture was cooled and added to a mixture of 1 N sodium hydroxide (200 ml), ether (100 ml) and pentane (100 ml). The organic extract was washed twice with 200 ml portions of water, twice with 200 ml portions of saturated sodium chloride, dried over magnesium sulfate and evaporated to give a quantitative yield of the title compound.

IR: (CHCl$_3$) 1656, 1626 and 1587 cm$^{-1}$.

MS: (m/e) 490 (M+), 475, 450, 449, 448, 446, 407, 405, 399, 383 and 91.

PMR: $\delta_{CDCl_3}{}^{TMS}$ 0.82 (n, terminal methyl), 1.22 (s, gem dimethyl), 3.1 (n, benzylic methine), 3.90 (s, ethylene ketal), 4.6–5.0 and 5.2–6.0 (n, vinyl H), 5.07 (s, benzylic methylene), 6.81 (d, J=2 Hz, ArH), 6.81 (dd, J=8 and 2 Hz, ArH) and 7.07 (d, J=8 Hz, ArH).

EXAMPLE 48 trans-3-[2-Benzyloxy-4-(1,1-dimethylheptyl)phenyl]-4-(2-butenyl)cyclohexanone

A mixture of trans-3-[2-benzyloxy-4-(1,1-dimethylheptyl)phenyl]-4-(2-butenyl)cyclohexanone ethylene ketal (700 mg, 1.38 mmole), dioxane (20 ml) and 2 N hydrochloric acid (20 ml) was heated at reflux for 1.5 hours. The reaction mixture was cooled, poured into ice water (500 ml) and extracted with ether (300 ml). The ether extract was washed with two 200 ml portions of saturated sodium bicarbonate, dried over magnesium sulfate and evaporated to give a quantitative yield of the title compound as an oil.

IR: (CHCl$_3$) 1715, 1616 and 1575 cm$^{-1}$.

MS: (m/e) 460 (M+), 403, 375, 369, 363, 313, 273, 271 and 91.

R$_f$: 0.43 (silica gel, 25% ether-pentane).

In like manner was prepared:

trans-3-[2-Benzyloxy-4-(1,1-dimethylheptyl)phenyl]-4-(2-pentenyl)cyclohexanone in quantitative yield as an oil from trans-3-[2-benzyloxy-4-(1,1-dimethylheptyl)phenyl]-4-(2-pentenyl)cyclohexanone ethylene ketal (540 mg, 1.04 mmole).

R$_f$: 0.57 (silica gel, 33% ether-pentane).

EXAMPLE 49

By means of the procedures of Examples 1, 3, 4, 47–49, compounds having the following formula are prepared wherein Z-W is as defined herein and R$_2$' is 2-propenyl, propyl, 2-butenyl, butyl and pentyl.

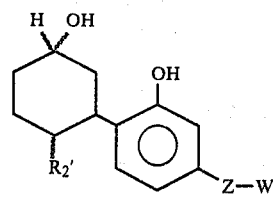

EXAMPLE 50 cis-3-[4-(1,1-Dimethylheptyl)-2-hydroxyphenyl]-cis-4-methyl-cyclohexanol and
cis-3-[4-(1,1-Dimethylheptyl)-2-hydroxyphenyl]-4-methylcyclohexanone A mixture of 3-[2-benzyloxy-4-(1,1-dimethylheptyl)phenyl]-4-methylcyclohex-2-enone and 391 mg of 5% Pd in carbon-50% water in methanol (15 ml) was stirred under one atmosphere of hydrogen until gas uptake ceased. The reaction was filtered through diatomaceous earth with ethyl acetate and evaporated. The residue was purified via column chromatography on silica gel eluted (200 g) with 50% ether-hexane to yield, in order of elution, 758 mg of a mixture of ketones and 820 mg (53%) of the title alcohol crystallized from cyclohexane. The mixture of ketones was further purified via preparative layer chromatography on five 20 cm×20 cm×2 mm silica gel plates eluted four times with dichloromethane to yield 112 mg (7.2%) of the title ketone as an oil.

Title alcohol
MP: 134°–135° C.
IR: (CHCl$_3$) 3623, 3333, 1626 and 1585 cm$^{-1}$.
MS: (m/e) 332 (M+), 314, 247 and 229.
PMR: $\delta_{CDCl_3}{}^{TMS}$ 0.69 (d, J=7 Hz, C-4 methyl), 0.85 (n, terminal methyl), 1.26 (s, gem dimethyl), 3.2 (n, benzylic methine), 3.8 (n, carbinol methine), 5.05 (s, OH) and 6.7–7.1 (n, ArH).

Analysis: Calculated for C$_{22}$H$_{36}$O$_2$: C, 79.46; H, 10.92%. Found: C, 79.40; H, 10.72%.

Title ketone
IR: (CHCl$_3$) 3623, 3390, 1634 and 1582 cm$^{-1}$.
MS: (m/e) 330 (M+), 315, 312, 288, 273, 271 and 245.
PMR: $\delta_{CDCl_3}{}^{TMS}$ 0.82 (n, terminal methyl), 0.88 (d, J=7 Hz, C-4 methyl), 1.26 (s, gem dimethyl) and 6.83 (s, all ArH).

EXAMPLE 51

5-(2-Benzyloxy-4-(1,1-dimethylheptyl)phenyl)-3-methoxy-6-methyl-2-cyclohexen-1-one To a −78° C. solution of 0.5 mole of lithiodiisopropylamide in 500 ml of tetrahydrofuran (from 50.5 g, 0.5 mole diisopropylamine and 417 ml of 1.2 M n-butyllithium in hexane) is added dropwise (30 mm) a solution of 217 g (0.5 mole) of 5-(2-benzyloxy-4-(1,1-dimethylheptyl)phenyl)-3-methoxy-2-cyclohexen-1-one in 250 ml of tetrahydrofuran. The reaction is stirred 30 minutes longer at −78° C. followed by the addition of 179 g (1.0 mole) of hexamethylphosphoramide and 78.1 g (0.55 mole) of methyl iodide. The reaction is allowed to slowly warm to room temperature, stirred one hour and quenched by the addition of 10 ml of water. The reaction is evaporated under reduced pressure to remove the tetrahydrofuran and added to one liter ice water-one liter ether. The ether extract is washed with three one liter portions of water, dried over magnesium sulfate and evaporated to yield the title compound in nearly pure form. The title compound is purified via column chromatography on 2 kg of silica gel eluted with ether-pentane.

Repetition of the procedure of this Example but using the appropriate $R_2'I$ and the appropriate 5-[2-benzyloxy-4-(Z-W)phenyl]-3-alkoxy-2-cyclohexen-1-one of Example 31 affords compounds having the formula

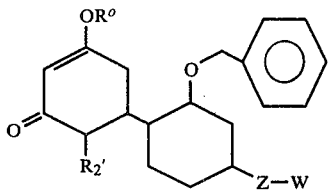

wherein $R^o$, Z and W are as defined in Example 31 and $R_2'$ is methyl, n-propyl, n-hexyl, benzyl, phenethyl, 4-phenylketyl, 2-propenyl, 2-butenyl, 5-hexenyl, 3-butenyl.

EXAMPLE 52

5-[2-Benzyloxy-4-(1,1-dimethylheptyl)phenyl]-3,4-dimethyl-2-cyclohexen-1-one

Following the procedure of Example 1, 5-[2-benzyloxy-4-(1,1-dimethylheptyl)phenyl]-3-methoxy-6-methyl-2-cyclohexen-1-one is reacted via the Grignard reaction with methyl magnesium iodide to give the title compound.

Debenzylation of the product according to the procedure of Example 2 affords the corresponding phenol.

The following compounds are thus prepared from appropriate compounds of Example 51 and appropriate Grignard reagents $R_4 Mg I$.

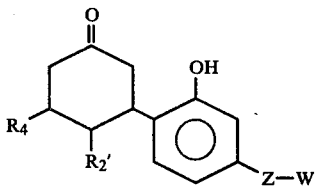

wherein $R_2'$, Z and W are as defined in Example 51 and $R_4$ is methyl ethyl, n-propyl, i-propyl and n-hexyl.

EXAMPLE 53

3-[2-Hydroxy-4-(1,1-dimethylheptyl)phenyl]-4,5-dimethylcyclohexanol

The bebenzylated compound of Example 52 is reduced with sodium borohydride according to the procedure of Example 11 to give the title compound.

Similarly the remaining compounds of Example 52 are reduced to the corresponding cyclohexanol derivative.

EXAMPLE 54

3-[2-Benzyloxy-4-(1,1-dimethylheptyl)phenyl]-4,5-dimethylcycloheptanone

To a $-78°$ C. solution of 17.4 g (0.10 mole) of dibromomethane and 21.7 g (0.050 mole) of 3-[2-benzyloxy-4-(1,1-dimethylheptyl)phenyl]-4,5-dimethylcyclohexanone in 100 ml of tetrahydrofuran is added dropwise over a period of 2 hours a solution of lithium dicyclohexylamide (0.10 mole) in 100 ml of tetrahydrofuran. The reaction is stirred one hour longer at $-78°$ C. and quenched by addition of 2 ml (0.11 mole) of water. The reaction is added to 300 ml ether and 200 ml water. The ether extract is dried over magnesium sulfate and evaporated. The crude product is purified via column chromatography on 500 g of silica gel eluted with ether-pentane to give pure 3-[2-benzyloxy-4-(1,1-dimethylheptyl)phenyl]-1-dibromomethyl-4,5-dimethylcyclohexanol.

To a $-78°$ C. solution of 30.4 g (0.050 mole) of 3-[2-benzyloxy-4-(1,1-dimethylheptyl)phenyl]-1-dibromomethyl-4,5-dimethylcyclohexanol in 150 ml of tetrahydrofuran is slowly added over a period of 2 hours 47.7 ml (0.105 mole) of n-butyllithium (2.2 M in hexane). The reaction solution is stirred 2 hours longer at $-78°$ C. and 10 minutes at $0°$ C. and then quenched by pouring into 300 ml of ice cold 1 N hydrochloric acid. The quenched reaction is extracted with two 250 ml portions of ether, the combined extract washed with 250 ml of saturated sodium chloride, dried over magnesium sulfate and evaporated. The residue is purified via column chromatography on 500 g of silica gel eluted with ether-pentane to yield the title compound.

Similarly, the remaining 3-[2-benzyloxy-4-(Z-W)phenyl]cyclohexanones described herein are converted to the corresponding cycloheptanone derivatives.

Reduction of the compounds thus produced by the procedures of Examples 3 and 4 affords the corresponding 3-[2-hydroxy-4-(Z-W)phenyl]cycloheptanols.

EXAMPLE 55

The products of Example 54 are subjected to the ring expansion procedure of said Example to give the corresponding 3-[2-benzyloxy-4-(Z-W)phenyl]cyclooctanones which are then reduced by the procedures of Examples 3 and 4 to the corresponding cyclooctanols having the formula shown below wherein the variables are as defined in the Examples:

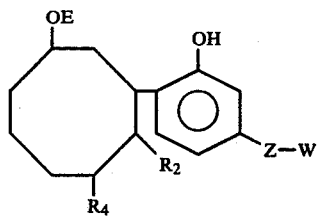

EXAMPLE 56

General Hydrochloride Salt Formation

Excess hydrogen chloride is passed into a solution of the appropriate compound of formula IA-ID having a pyridyl group and the resulting precipitate separated and recrystallized from an appropriate solvent, e.g. methanol-ether (1:10).

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts are prepared.

EXAMPLE 57 cis-3-[4-(1,1-Dimethylheptyl)-2-hydroxyphenyl]cyclohexanol 2'-O-hemisuccinate ester sodium salt To a 0° C. solution of 1.00 g (3.14 mmoles) of cis-3-[4-(1,1-dimethylheptyl)-2-hydroxyphenyl]cyclohexanol in 3 ml of dichloromethane is added 0.383 g (3.14 mmoles) of 4-N,N-dimethylaminopyridine. To the resultant solution is slowly added 0.314 g (3.14 mmoles) of succinic anhydride in one ml of dichloromethane. The reaction mixture is stirred for 4 hours at 0° C. and then 3.14 ml of 1 N hydrochloric acid is slowly added. The reaction mixture is stirred 5 minutes longer and then added to 100 ml water-100 ml dichloromethane. The dichloromethane extract is dried over magnesium sulfate and evaporated. The residue is dissolved in 5 ml of ethanol and 3.14 ml of 1 N sodium hydroxide in ethanol added. Addition of ether causes crystallization. Recrystallization from ethanol-ether yields the title compound.

Replacement of sodium hydroxide by potassium hydroxide in the above procedure affords the potassium salt.

By means of this procedure, the remaining compounds described herein are converted to their hemisuccinate esters.

EXAMPLE 58 cis-3-[4-(1,1-dimethylheptyl)-2-hydroxyphenyl]cyclohexanol 2'-O-phosphate ester monosodium salt To a 0° C. slurry of 0.126 g (3.14 mmoles) of potassium hydride in 3 ml of dimethylformamide is added a solution of 1.00 g (3.14 mmoles) of cis-3-[4-(1,1-dimethylheptyl)-2-hydroxyphenyl]cyclohexanol in 3 ml of dimethylformamide. After gas evolution ceases (~10 minutes) 0.932 g (3.14 mmoles) of dibenzylphosphorochloridate is slowly added. The reaction mixture is stirred for one hour and then added to 200 ml ether-100 ml water. The ether extract is washed with two 100 ml portions of water, dried over magnesium sulfate and evaporated to a residue. The residue is mixed with 1.0 g of 5% platinum on carbon and 25 ml of ethanol and stirred under one atmosphere of hydrogen for 3 hours. The reaction mixture is filtered through diatomaceous earth and 3.14 ml of 1 N sodium hydroxide in ethanol slowly added to the filtrate. Addition of ether causes crystallization of the product. Recrystallization from ethanol then yields the title compound.

Similarly, the remaining compounds described herein are converted to their phosphate ester mono sodium salts and, by replacement of sodium hydroxide with potassium hydroxide, to their corresponding potassium salts.

EXAMPLE 59

One hundred mg of 3-[4-(1,1-dimethylheptyl)-2-hydroxyphenyl]cyclohexanol are intimately mixed and ground with 900 mg of starch. The mixture is then loaded into telescoping gelatin capsules such that each capsule contains 10 mg of drug and 90 mg of starch.

EXAMPLE 60

A tablet base is prepared by blending the ingredients listed below:
Sucrose: 80.3 parts
Tapioca starch: 13.2 parts
Magnesium stearate: 6.5 parts
Sufficient trans-3-[2-hydroxy-4-(2-(5-phenylpentyloxy))phenyl]cyclohexanol is blended into this base to provide tablets containing 0.1, 0.5, 1, 5, 10 and 25 mg of drug.

EXAMPLE 61

Suspensions of 3-[4-(1,1-dimethylheptyl)-2-hydroxyphenyl]cyclohexanone are prepared by adding sufficient amounts of drug to 0.5% methylcellulose to provide suspensions having 0.05, 0.1, 0.5, 1, 5 and 10 mg of drug per ml.

PREPARATION A 2-(3-Benzyloxyphenyl)-2-methylpropionitrile

To a solution of 1500 ml. of dimethylsulfoxide saturated with methyl bromide was simultaneously added a solution of 295 g. (1.32 mole) of 2-(3-benzyloxyphenyl)acetonitrile in 200 ml. dimethyl sulfoxide and a solution of 420 ml. of 50% aqueous sodium hydroxide. Methyl bromide was continuously bubbled through the reaction mixture during the above addition (30 minutes) and then for 1.5 hours longer while the reaction temperature was maintained at $\leq 50°$ C. with ice cooling. The reaction mixture was added to 2 liters of water—2 kg. ice and the resultant mixture extracted four times with 1 liter of ether. The combined ether extracts were washed twice with one liter of water, once with one liter of saturated sodium chloride, dried over magnesium sulfate and evaporated to yield 325 g. (98%) of product as an oil.

PMR: $\delta_{CDCl_3}^{TMS}$ 1.70 (s, methyl), 5.12 (s, methylene), 6.8–7.5 (m, ArH) and 7.45 (s, PhH).
IR: (CHCl$_3$) 2247, 1616 and 1603 cm$^{-1}$.
MS: m/e 251 (M+), 236, 160 and 91.

PREPARATION B 2-(3-Benzyloxyphenyl)-2-methylpropionaldehyde

To a 15° C. solution of 325 g. (1.25 mole of 2-(3-benzyloxyphenyl)-2-methylpropionitrile in 1.85 liters of tetrahydrofuran was added 1.6 moles of diisobutylaluminum hydride as a 1.3 M solution in hexane (reaction temperature is maintained at 15°–18° C.). The reaction mixture was allowed to warm to room temperature and was stirred 2 hours longer. It was then quenched by addition to a solution of 170 ml. of concentrated sulfuric acid in 670 ml. of water (temperature $\leq 30°$ C.). The resultant mixture was allowed to warm to room temperature and was then stirred an additional 2 hours. The organic layer was separated and the aqueous phase extracted once with one liter of ether. The combined organic phase was washed with 500 ml. of water and 500 ml. of saturated sodium chloride, dried over magnesium sulfate and evaporated to yield 315 g. (99%) of the title product.

PMR: $\delta_{CDCl_3}^{TMS}$ 1.43 (s, methyls), 5.08 (s, methylenes), 6.8–7.5 (m, ArH), 7.4 (s, PhH) and 9.55 (s, aldehyde).
IR: (CHCl$_3$) 1742 and 1613 cm$^{-1}$.
MS: 254 (M+), 259 and 91.

PREPARATION C

1-Benzyloxy-3-(1,1-dimethyl-2-heptenyl)benzene

To a 15° C. solution of 1.8 moles of dimsyl sodium (from sodium hydride and dimethyl sulfoxide) in 2 liters of dimethyl sulfoxide was added, portion-wise, 768 g. (1.8 moles) of pentyltriphenylphosphonium bromide. The resultant slurry was stirred 15 minutes at 15°–20° C. and then 315 g. (1.24 moles) of 2-(3-benzyloxyphenyl)-

2-methylpropionaldehyde was slowly added (reaction temperature ≦30° C.). The resultant mixture was stirred for 4 hours at room temperature and was then added to 6 liters of ice water. The quenched reaction was extracted four times with one liter portions of 50% ether-pentane. The combined extract was washed twice with one liter of water and once with one liter of saturated sodium chloride and was then dried over magnesium sulfate and evaporated to yield an oil. Crystallization of this oil is 50% ether-pentane (to remove triphenylphosphine oxide), filtration and evaporation of the filtrate gave 559 g. of oil. The crude oil was purified via column chromatography on 2 kg. of silica gel eluted with 20% hexane-dichloromethane to yield 217 g. (57%) of product as an oil.

PMR: $\delta_{CDCl_3}^{TMS}$ 0.75 (bt, J=6 Hz, terminal methyl), 1.1 (m, two side-chain methylenes), 1.43 (s, gem dimethyl), 1.60 (m, allylic methylene), 5.09 (s, benzylic methylene), 5.28 (dt, J=12 and 6 Hz, vinyl H), 5.70 (dd, J=12 and 1 Hz, vinyl H), 6.7-7.5 (m, ArH) and 7.42 (s, PhH).

IR: (CHCl$_3$) 1610 and 1587 cm$^{-1}$.

MS: m/e 308 (M+), 293, 274, 265, 251, 239, 225, 217 and 91.

Similarly, 1-benzyloxy-3-(1,1-dimethyloct-2-enyl)benzene (13.5 g., 70%) was prepared from 15.75 g. (0.062 mol.) of 2-(3-benzyloxyphenyl)-2-methyl-propionaldehyde and 37.5 g. (0.0899 mol.) of hexyltriphenylphosphonium bromide. The product was an oil.

PMR: $\delta_{CDCl_3}^{TMS}$ 0.78 (m, terminal sidechain methyl), 1.40 (s, gem dimethyl), 4.97 (s, benzyl ether methylene), 5.23 (m, vinyl H), 5.57 (d, J=11 Hz, vinyl H) and 6.6-7.4 (m, ArH and PhH).

IR: (CHCl$_3$) 1608 and 1582 cm$^{-1}$.

MS: m/e 322 (M+), 307, 279, 274, 265 and 231.

1-benzyloxy-3-(1,1-dimethyl-2-propenyl)benzene as an oil (23.0 g., 91%) from 2-(3-benzyloxyphenyl)-2-methylpropionaldehyde (25.5 g., 0.10 mole) and methyltriphenylphosphonium bromide (40.3 g., 0.113 mole).

PMR: $\delta_{CDCl_3}^{TMS}$ 1.40 (s, gem dimethyl), 4.90 (dd, J=18 and 2 Hz, vinyl H), 4.90 (dd, J=10 and 2 Hz, vinyl H), 5.05 (s, benzyl ether methylene), 6.03 (dd, J=18 and 10 Hz, vinyl H) and 6.7-7.6 (m, ArH and PhH).

IR: (CHCl$_3$) 1650, 1608 and 1587 cm$^{-1}$.

MS: m/e 252 (M+), 237, 183, 161 and 91.

1-benzyloxy-3-(1,1-dimethyl-2-butenyl)benzene as an oil (37.3 g., 77%) from 2-(3-benzyloxyphenyl)-2-methylpropionaldehyde (46.2 g., 0.182 mole) and ethyltriphenylphoxphonium bromide (75.0 g., 0.202 mole).

PMR: $\delta_{CDCl_3}^{TMS}$ 1.22 (d, J=6 Hz, vinyl methyl), 1.41 (s, gem dimethyl), 5.03 (s, benzyl ether methylene), 5.0-5.8 (m, vinyl H), 6.6-7.5 (m, ArH and PhH).

IR: (CHCl$_3$) 1661, 1626, 1621, 1608 and 1587 cm$^{-1}$.

MS: m/e 266 M+), 251, 226, 183, 175 and 91.

1-benzyloxy-3-(1,1-dimethyl-2-pentenyl)benzene as an oil (31 g., 74%) from 2-(3-benzyloxyphenyl)-2-methylpropionaldehyde (40.0 g., 0.157 mole) and propyltriphenylphosphonium bromide (66.7 g., 0.173 mole).

IR: (CHCl$_3$) 1626 and 1600 cm$^{-1}$.

MS: (m/e) 280 (M+), 265, 251, 237, 225, 211, 189, 147 and 91.

PMR: $\delta_{CDCl_3}^{TMS}$ 0.62 (t, J=7 Hz, methyl), 1.40 s, gem dimethyl), 5.00 (s, benzylic methylene), 0.20 (dt, J=11 and 7 Hz, vinyl H), 5.59 (dt, J=11 and 1 Hz, vinyl H) and 6.6-7.4 (m, ArH).

1-Benzyloxy-3-(1,1-dimethyl-2-hexenyl)benzene as an oil (35 g., 76%) from 2-(3-benzyloxyphenyl)-2-methylpropionaldehyde (40.0 g., 0.157 mole) and butyltriphenylphosphonium bromide (69.0 l., 0.173 mole).

IR (CHCl$_3$) 1623 and 1600 cm$^1$.

MS: (m/e) 294 (M+), 279, 265, 251, 255 and 91.

PMR: $\delta_{CDCl_3}^{TMS}$ 0.69 (m, terminal methyl), 1.42 (s, gemdimethyl), 5.09 (s, benzylic methylene), 5.4 (m, vinyl H), 5.77 (d, J=12 Hz, vinyl H) and 6.75-7.7 (m, ArH).

1-benzyloxy-3-(1,1-dimethyl-2-nonenyl)benzene as an oil (34.5 g., 75%) from 2-(3-benzyloxyphenyl)-2-methylpropionaldehyde (40.0 g., 0.157) and heptyltriphenylphosphonium bromide (60.0 l g., 0.138 mole).

R$_f$: 0.72 (silica gel, 33% ether-cyclohexane).

1-benzyloxy-3-(1,1-dimethyl-2-decenyl)benzene an an oil (43 g., 78%) from 2-(3-benzyloxyphenyl)-2-methylpropionaldehyde (40.0 g., 0.157 mole) and octyltriphenylphosphonium bromide (81.0 g., 0.178 mole).

IR: (CHCl$_3$) 1621 and 1600 cm$^{-1}$.

MS: (m/e) 350 (M+), 335, 308, 281, 263, 251 and 91.

PMR: $\delta_{CDCl_3}^{TMS}$ 0.83 (m, terminal methyl), 1.37 (s, gem dimethyl), 5.03 (s, benzylic methylene), 5.23 (dt, J=11 and 7 Hz, vinyl H), 5.54 (bd, J=11 Hz, vinyl H) and 6.65-7.55 (m, ArH).

1-benzyloxy-3-(1,1-dimethyl-2-undecenyl)benzene as an oil (36 l g., 63%) from 2-(3-benzyloxyphenyl)-2-methylpropionaldehyde (40.0 g., 0.157 mole) and nonyltriphenylphosphonium bromide (81.1 g., 0.173 mole).

IR: (CHCl$_3$) 1613 and 1592 cm$^{-1}$.

MS: (m/e) 364 (M+), 349, 321, 295, 273, 251 and 91.

PMR: $\delta_{CDCl_3}^{TMS}$ 0.87 (m, terminal methyl), 1.38 (s, gem dimethyl), 5.03 (s, benzylic methylene), 5.25 (dt, J=12 and 6 Hz, vinyl H), 5.65 (bd, J=12 Hz, vinyl H) and 6.65-7.6 (m, ArH).

PREPARATION D

3-(1,1-Dimethylheptyl)phenol

A mixture of 65 g. (0.211 mole) of 2-(3-benzyloxyphenyl)-2-methyl-cis-oct-3-ene and 7.5 g. of 10% palladium-on-carbon in 100 ml. of ethanol was hydrogenated for one hour on a Parr apparatus at 50 p.s.i. hydrogen pressure. Additional 7.5 g. portions of 10% palladium-on-carbon were added after one and two hours of reaction and the reaction continued for 12 more hours. The reaction mixture was filtered through diatomaceous earth with ethanol and the filtrate evaporated to an oil. The oil was purified via column chromatography on one kg. of silica gel eluted with 50% hexane-dichloromethane to yield 105 g. (78%) of product as an oil.

PMR: $\delta_{CDCl_3}^{TMS}$ 0.85 (bt, terminal methyl), 1-1.9 (m, methylenes), 1.29 (s, gem dimethyl), 4.98 (s, phenol H) and 6.6-7.4 (m, ArH).

IR: (CHCl$_3$) 3571, 3311 and 1592 cm$^{-1}$.

MS: m/e 220 (M+), 205 and 135.

In the like manner, 3-(1,1-dimethyloctyl)phenol was prepared in 82% (7.8 g.) yield from 13.0 g. (0.0406 mol.) of 1-benzyloxy-3-(1,1-dimethyl-oct-2-enyl)benzene. It was obtained as an oil having the characteristics:

PMR: $\delta_{CDCl_3}^{TMS}$ 0.85 (m, terminal methyl), 1.27 (s, gem dimethyl), 5.25 (bs, OH) and 6.6-7.4 (m, ArH).

IR: (CHCl$_3$) 3571, 3279, 1563 and 1527$^{-1}$.

MS: m/e 234 (M+), 219, 191, 178, 164, 149, 135 and 121.

3-(1,1-dimethylpropyl)phenol as an oil (11.7 g., 78%) from 1-benzyloxy-3-(1,1-dimethyl-2-propenyl)benzene (23.0 g., 0.0912 mole).

PMR: $\delta_{CDCl_3}^{TMS}$ 0.67 (t, J=7 Hz, terminal methyl), 1.23 (s, gem dimethyl), 1.58 (q, J=7 Hz, methylene), 6.03 (s, OH) and 6.6–7.4 (m, ArH).

IR: (CHCl$_3$) 3534, 3300, 1613 and 1587 cm$^{-1}$.

MS: m/e 164 (M+), 149, 135 and 108.

3-(1,1-dimethylbutyl)phenol as an oil (21.0 g., 84%) from 1-benzyloxy-3-(1,1-dimethyl-2-butenyl)benzene (37.3 g., 0.140 mole).

PMR: $\delta_{CDCl_3}^{TMS}$ 0.85 (m, terminal methyl), 1.18 (s, gem dimethyl), 5.42 (bs, OH) and 6.5–7.3 (m, ArH).

IR: (CHCl$_3$) 3623, 3448 and 1613 cm$^{-1}$.

MS: m/e 178 (M+), 163, 135, 121 and 107.

3-(1,1-Dimethylpentyl)phenol as an oil (16 g., 75% from 1-benzyloxy-3-(1,1-dimethyl-2-pentenyl)benzene (31.0 1 g., 0.111 mole).

IR: (CHCl$_3$) 3636, 3390, 1634, 1623 and 1605 cm$^{-1}$.

MS: (m/e) 192 (M+), 135 and 108.

PMR: $\delta_{CDCl_3}^{TMS}$ 0.82 (m, methyl), 1.26 (s, gem dimethyl) and 6.5–7.4 (m, ArH).

3-(1,1-Dimethylhexyl)phenol as an oil (18 g., 74%) from 1-benzyloxy-3-(1,1-dimethyl-2-hexenyl)benzene (35.0 g., 0.119 mole).

IR: (CHCl$_3$) 3650, 3390 and 1626 (broad) cm$^{-1}$.

MS: (m/e) 206 (M+), 191, 177, 163, 149 and 135.

PMR: $\delta_{CHCl_3}^{TMS}$ 0.80 (m, methyl), 1.22 (s, gem dimethyl) and 6.5–7.3 (m, ArH).

3-(1,1-Dimethylnonyl)phenol as an oil (20.6 g., 86%) from 1-benzyloxy-3-(1,1-dimethyl-2-nonenyl)benzene (34.5 g., 0.103 mole).

IR: (CHCl$_3$) 3636, 3378 and 1613 (broad) cm$^{-1}$.

MS: (m/e) 248 (M+), 233, 192, 178 and 135.

PMR: $\delta_{CDCl_3}^{TMS}$ 0.86 (m, terminal methyl), 1.22 (s, gem dimethyl), 5.37 (S, OH) and 6.5–7.3 (M, ArH).

3-(1,1-Dimethyldecyl)phenol as an oil (21.0 g., (65%) from 1-benzyloxy-3-(1,1-dimethyl-2-decenyl)benzene (43.0 g., 0.123 mole).

IR: (CHCl$_3$) 3636, 3333 and 1613 (broad) cm$^{-1}$.

MS: (m/e) 262 (M+), 247, 206, 191, 178, 166, 155 and 135.

PMR: $\delta_{CDCl_3}^{TMS}$ 0.88 (m, terminal methyl), 1.23 (s, gem dimethyl) and 6.5–7.4 (m, ArH).

3-(1,1-Dimethylundecyl)phenol as an oil (21 g., 77%) from 1-benzyloxy-3-(1,1-dimethyl-2-undecenyl)benzene (36 g., 0.099 mole).

IR: (CHCl$_3$) 3534, 3279 and 1597 cm$^{-1}$.

MS: (m/e) 276 (M+), 261, 220, 184 and 135.

PMR: $\delta_{CDCl_3}^{TMS}$ 0.87 (m, terminal methyl), 1.22 (s, gem dimethyl), 5.1 (broad, OH) and 6.5–7.3 (m, ArH).

PREPARATION E

2-(4-Bromo-3-hydroxyphenyl)-2-methyloctane

To a 0° C. solution of 110 g. (0.50 mole) of 2-(3-hydroxyphenyl)-2-methyloctane in 200 ml. of carbon tetrachloride was added dropwise a solution of 80 g. (0.50 mole) of bromine in 90 ml. of carbon tetrachloride (reaction temperature ≦30° C. with cooling). The reaction mixture was stirred an additional 15 minutes and was then evaporated to yield 150 g. (100%) of product as an oil.

PMR: $\delta_{CDCl_3}^{TMS}$ 0.85 (bt, terminal methyl), 0.8–1.9 (m, methylenes), 1.28 (s, gem dimethyl), 5.4 (bs, phenolic H), 6.78 (dd, J=8 and 2 Hz, C-6 ArH), 7.02 (d, J=2 Hz, C-2 ArH) and 7.37 (d, J=8 Hz, C-5 ArH.

IR: (CHCl$_3$) 3559, 3289 and 1585 cm$^{-1}$.

MS: m/e 300, 289 (M+), 215, 213, 201, 199, 187 and 185.

In like manner, 2-(4-bromo-3-hydroxyphenyl)-2-methylnonane was prepared in 82% (8.5 g.) yield as an oil from 7.8 g. (0.033 mol.) of 2-(3-hydroxyphenyl)-2-methylnonane:

PMR: $\delta_{CDCl_3}^{TMS}$ 0.86 (m, terminal methyl), 1.27 (s, gem dimethyl), 5.50 (bs, OH), 6.83 (dd, J=8 and 2 Hz, ArH), 7.08 (d, J=2 Hz, ArH) and 7.43 (d, J=8 Hz, ArH).

IR: (CHCl$_3$) 3279, 1613, and 1587 cm$^{-1}$.

MS: m/e 314, 312 (M+), 212, 210, 185 and 187.

2-(4-bromo-3-hydroxyphenyl)-2-methylbutane as an oil (12.7 g., 98%) from 2-(3-hydroxyphenyl)-2-methylbutane (9.50 g., 0.0579 mole).

PMR: $\delta_{CDCl_3}^{TMS}$ 0.67 (t, J=7 Hz, terminal methyl), 1.23 (s, gem dimethyl), 1.56 (q, J=7 Hz, methylene), 5.2 (bs, OH), 6.84 (dd, J=8 Hz, ArH).

IR: (CHCl$_3$) 3521, 3279, 1608, 1600 and 1577 cm$^{-1}$.

MS: m/e 244, 242 (M+), 229, 227, 215, 213, 187 and 185;

2-(4-bromo-3-hydroxyphenyl)-2-methylpentane as an oil (29.9 g., 99%) from 2-(3-hydroxyphenyl-2-methylpentane (21.0 g., 0.118 mole).

PMR: $\delta_{CDCl_3}^{TMS}$ 0.83 (m, terminal methyl), 1.22 (s, gem dimethyl), 5.42 (bs, OH), 6.75 (dd, J=8 and 2 Hz, ArH), 6.98 (d, J=2 Hz, ArH) and 7.32 (d, J=8 Hz, ArH).

IR: (CHCl$_3$) 3610, 3333, 1618 and 1600 cm$^{-1}$.

MS: m/e 258, 256 (M+), 243, 241, 215, 213, 201, 199, 187 and 185.

2-(4-bromo-3-hydroxyphenyl)-2-methylhexane as an oil (22.8 g., 100%) from 2-(3-hydroxyphenyl)-2-methylhexane (16.0 g., 0.0833 mole).

IR: (CHCl$_3$) 3610, 3333 and 1600 cm$^{-1}$.

MS: (m/e) 272 and 270 (M+), 215, 213, 187.

2-(4-bromo-3-hydroxyphenyl)-2-methylheptane as an oil (quantitative) from 2-(3-hydroxyphenyl)-2-methylheptane (20.0 g., 0.971 mole).

IR: (CHCl$_3$) 3584, 3333 and 1600 cm$^{-1}$.

MS: (m/e) 286 and 284 (M+), 215, 213, 187 and 185.

PMR: $\delta_{CDCl_3}^{TMS}$ 0.87 (m, terminal methyl) 1.30 (s, gem dimethyl), 5.49 (bs, OH), 683 (dd, J=8 and 2 Hz, ArH), 7.07 (d, J=2 Hz, ArH) and 7.42 (d, J=8 Hz, ArH).

2-(4-bromo-3-hydroxyphenyl)-2-methyldecane as an oil (23.2 g., 85%) from 2-(3-hydroxyphenyl)-2-methyldecane (20.6 g., 0.0831 mole).

IR: (CHCl$_3$) 3571, 3333 and 1661 cm$^{-1}$.

MS: (m/e) 356 and 354 (M+), 340, 338, 215 and 213.

PMR: $\delta_{CDCl_3}^{TMS}$ 0.82 (m, terminal methyl), 1.30 (s, gem dimethyl), 5.49 (s, OH), 6.82 (dd, J=8 and 2 Hz, ArH), 7.07 (d, J=2 Hz, ArH) and 7.41 (d, J=8 Hz, ArH).

2-(4-bromo-3-hydroxyphenyl)-2-methylundecane as an oil (quantitative) from 2-(3-hydroxyphenyl)-2-methylhendecane (21.0 g., 0.0802 mole).

IR: (CHCl$_3$) 3571, 3333 and 1600 (broad) cm$^{-1}$.

MS: (m/e) 342 and 340 (M+), 215, 213, 187 and 185.

PMR: $\delta_{CDCl_3}^{TMS}$ 0.86 (m, terminal methyls), 1.22 (s, gem dimethyl), 5.45 (bs, OH), 6.74 (dd, J=8 and 2 Hz, ArH), 6.99 (d, J=2 Hz, ArH) and 7.33 (d, J=8 Hz, ArH).

2-(4-bromo-3-hydroxyphenyl)-2-methyldodecane as an oil (22.0 g., 81%) from 2-(3-hydroxyphenyl)-2-methyldodecane (21.0 1 g., 0.0761 mole).

IR: (CHCl$_3$) 3597, 3333, 1613 and 1592 cm$^{-1}$.

MS: (m/e) 356 and 354 (M+), 340, 338, 215 and 213.

PMR: $\delta_{CDCl_3}{}^{TMS}$ 0.92 (m, terminal methyl), 1.29 (s, gem dimethyl), 5.47 (bs, OH), 6.81 (dd, J=8 and 2 Hz, ArH), 7.06 (d, J=2 Hz, ArH) and 7.41 (d, J=8 Hz, ArH).

PREPARATION F

2-(3-Benzyloxy-4-bromophenyl)-2-methyloctane

To a −18° C. slurry of 23.0 g. (0.575 mole) of potassium hydride in 400 ml. of N,N-dimethylformamide was added over a 45 minute period a solution of 150 g. (0.5 mole) of 2-(4-bromo-3-hydroxyphenyl)-2-methyloctane in 400 ml. of N,N-dimethylformamide (reaction temperature ≦−15° C.). The reaction mixture was stirred 15 minutes longer after which a solution of 98.3 g. (0.575 mole) of benzyl bromide in 200 ml. of N,N-dimethylformamide was added. The mixture was then warmed to room temperature and stirred 30 minutes longer. It was quenched by addition to 6 liters of ice water. The quenched mixture was extracted six times with 500 ml. of ether. The combined extract was washed twice with one liter portions of water and once with one liter of saturated sodium chloride, dried over magnesium sulfate and evaporated to a quantitative yield of the title product.

PMR: $\delta_{CDCl_3}{}^{TMS}$ 0.85 (bt, terminal methyl), 0.8–2.0 (m, methylenes), 1.22 (s, gem dimethyl), 5.17 (s, benzylic methylene) and 6.7–7.6 (two multiplets, ArH and PhH).

IR: (CHCl₃) 1592 and 1575 cm⁻¹.

MS: m/e 390, 388 (M+), 375, 373, 354, 352, 305, 303 and 91.

2-(3-benzyloxy-4-bromophenyl)-2-methyl-nonane was prepared in 95% (10.4 g.) yield from 2-(3-hydroxy-4-bromophenyl)-2-methylnonane (8.5 g., 0.027 mol.), sodium hydride (0.744 g., 0.031 mol.) and benzyl bromide (5.3 g., 0.031 mol.) as an oil.

PMR: $\delta_{CDCl_3}{}^{TMS}$ 0.87 (terminal methyl), 1.23 (s, gem dimethyl), 5.18 (s, benzyl ether methylene), 6.8 (dd, J=8 and 2 Hz, ArH), 6.97 (d, J=2 Hz, ArH) and 7.43 (m, ArH and PhH).

IR: (CHCl₃) 1600 and 1575 cm⁻¹.

MS: m/e 404, 402 (M+), 305, 303, 91;

2-(3-benzyloxy-4-bromophenyl)-2-methylpropane (46.5 g., 88%) from 2-(4-bromo-3-hydroxyphenyl)-2-methylpropane (38.0 g., 0.166 mole).

MP: 52°–54° C. (from pentane)

PMR: $\delta_{CDCl_3}{}^{TMS}$ 1.25 (s, t-butyl), 5.18 (s, benzyl ether methylene), 6.7–7.0 (m, two ArH) and 7.2–7.6 (m, one ArH and PhH).

IR: (CHCl₃) 1600 and 1585 cm⁻¹.

MS: m/e 320, 318 (M+), 305, 303, 239 and 223.

2-(3-benzyloxy-4-bromophenyl)-2-methylbutane as an oil (24.9 g., 99%) 2-(4-bromo-3-hydroxyphenyl)-2-methylbutane (17.3 g., 0.0777 mole).

IR: (CHCl₃) 1600 and 1585 cm⁻¹.

MS: m/e 334, 332 (M+), 319, 317, 309, 303, 253, 223 and 91.

2-(3-benzyloxy-4-bromophenyl)-2-methylpentane as an oil (34.3 g., 99%) from 2-(4-bromo-3-hydroxyphenyl)-2-methylpentane (25.7 g., 0.100 mole).

PMR: $\delta_{CDCl_3}{}^{TMS}$ 0.80 (m, terminal methyl), 1.23 (s, gem dimethyl), 5.12 (s, benzyl ether methylene, 6.6–6.9 (m, two ArH) and 7.1–7.5 (m, ArH and PhH).

IR: (CHCl₃) 1610 and 1595 cm⁻¹.

MS: m/e 348, 346 (M+), 333, 331, 305, 303, and 91.

2-(3-benzyloxy-4-bromophenyl)-2-methylhexane as an oil (30 g., 98%) from 2-(4-bromo-3-hydroxyphenyl)-2-methylhexane (22.7 g., 0.0831 mole).

IR: (CHCl₃) 1605 and 1592 cm⁻¹.

MS: (m/e) 363 and 361 (M+), 305 and 303.

PMR: $\delta_{CDCl_3}{}^{TMS}$ 0.78 (m, terminal methyl), 1.18 (s, gem dimethyl), 5.12 (s, benzylic methylene), 6.65–6.9 (m, ArH) and 7.15–7.6 (m, ArH and Ph). 2-(3-benzyloxy-4-bromophenyl)-2-methylheptane as an oil (quantitative) from 2-(4-bromo-3-hydroxyphenyl)-2-methylheptane (23.0 g., 0.0806 mole).

IR: (CHCl₃) 1600 and 1582 cm⁻¹.

MS: (m/e) 376 and 374 (M+), 305, 303, 215 and 213.

PMR: $\delta_{CDCl_3}{}^{TMS}$ 0.80 (m, terminal methyl), 1.19 (s, gem dimethyl), 5.12 (s, benzylic methylene), 6.65–6.95 (m, ArH), 7.15–7.6 (M, ArH and Ph).

2-(3-benzyloxy-4-(bromophenyl)-2-methyldecane as an oil (quantitative) from 2-(4-bromo-3-hydroxyphenyl)-2-methyldecane (23.2 g., 0.0712 mole).

IR: (CHCl₃) 1600 and 1585 cm⁻¹.

MS: (m/e) 418 and 416 (M+), 305, 303, 215 and 213.

PMR: $\delta_{CDCl_3}{}^{TMS}$ 0.91 (m, terminal methyl), 1.26 (s, gem dimethyl), 5.19 (s, benzylic methylene), 6.7–7.0 (m, ArH) and 7.25–7.65 (m, ArH and Ph).

2-(3-benzyloxy-4-bromophenyl)-2-methylundecane as an oil (40.0 g., 82%) from 2-(4-bromo-3-hydroxyphenyl)-2-methylhendecane (27.3 g., 0.113 mole).

IR: (CHCl₃) 1605 and 1587 cm⁻¹.

MS: (m/e) 432 and 430 (M+), 305, 303, 215 and 213.

PMR: $\delta_{CDCl_3}{}^{TMS}$ 0.90 (m, terminal methyl), 1.24 (s, gem dimethyl), 5.18 (s, benzylic methylene), 6.7–7.0 (m, ArH) and 7.2–7.6 (m, ArH and Ph).

2-(3-benzyloxy-4-bromophenyl)-2-methyldodecane as an oil (27.5 g., 100%) from 2-(4-bromo-3-hydroxyphenyl)-2-methyldodecane (22.0 g., 0.0620 mole).

IR: (CHCl₃) 1605 and 1592 cm⁻¹.

MS: (m/e) 446 and 444 (M+), 305 and 303.

PMR: $\delta_{CDCl_3}{}^{TMS}$ 0.86 (m, terminal methyl), 1.21 (s, gem dimethyl), 5.13 (s, benzylic methylene), 6.7–6.95 (m, ArH) and 7.2–7.55 (m, ArH and Ph).

The compounds tabulated below are prepared according to the procedures of Preparations C–F from appropriate reactants:

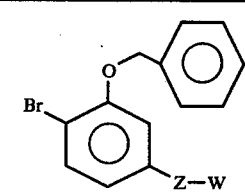

| Z | W |
|---|---|
| C(CH₃)₂(CH₂)₄ | C₆H₅ |
| C(CH₃)₂(CH₂)₄ | 4-pyridyl |
| C(CH₃)₂(CH₂)₃ | 2-pyridyl |
| C(CH₃)₂(CH₂)₁₀ | C₆H₅ |
| CH(CH₃)(CH₂)₂ | C₆H₅ |
| CH(C₂H₅)(CH₂)₂ | 4-ClC₆H₄ |
| CH(C₂H₅)(CH₂)₄ | 4-FC₆H₄ |
| (CH₂)₅ | H |
| (CH₂)₁₁ | H |
| (CH₂)₁₃ | H |
| (CH₂)₄ | C₆H₅ |
| (CH₂)₈ | H |

PREPARATION G

3-Benzyloxy-4-bromophenol

To a 0° C. slurry of 1.7 g. (42.5 mmoles) of potassium hydride in 35 ml. of N,N-dimethylformamide was slowly added a solution of 7.22 g. (38.2 mmoles) of 4-bromoresorcinol. The resultant mixture was stirred for 30 minutes and then 4.54 ml. (38.2 mmoles) of benzyl bromide was slowly added. The reaction mixture was stirred 3 hours longer at 0° C. and then added to 200 ml. of cold water and 200 ml. of ether. The ether extract was washed twice with 200 ml. portions of water, dried over magnesium sulfate and evaporated to an oil. The crude oil was purified via column chromatography on 400 g. of silica gel eluted with 25% ether-pentane to yield (in order of elution) 2.2 g. (16%) of 2,4-dibenzyloxybromobenzene, 0.21 g. (2%) of 5-benzyloxy-2-bromophenol and 3.52 g. (33%) of 3-benzyloxy-4-bromophenol.

5-Benzyloxy-2-bromophenol:

PMR: $\delta_{CDCl_3}^{TMS}$ 4.98 (s, benzyl ether), 5.46 (bs, OH), 6.40 (dd, J=8 and 2 Hz, ArH), 6.60 (d, J=2 Hz, ArH), 7.17 (d, j=8 Hz, ArH) and 7.33 (s, PhH).

IR: (CHCl$_3$) 3521, 3221, 1610 and 1600 cm$^{-1}$.

MS: m/e 280, 278 (M+), 189, 187 and 91.

3-Benzyloxy-4-bromophenol:

PMR: $\delta_{CDCl_3}^{TMS}$ 5.00 (s, benzyl ether methylene), 5.33 (bs, OH), 6.21 1 (dd, J=8 and 2 Hz, ArH), 6.38 (d, J=2 Hz, ArH) and 7.30 (m, ArH and PhH).

IR: (CHCl$_3$) 3546, 3257, 1603 and 1585 cm$^{-1}$.

MS: m/e 280, 278 (M+) and 91.

PREPARATION H

2-Benzyloxy-4-[2-(5-phenylpentyloxy)]bromobenzene

A mixture of 3.50 g. (12.5 mmoles) of 3-benzyloxy-4-bromophenol, 3.48 g. (14.4 mmoles) of 2-(5-phenylpentyl)methanesulfonate and 5.17 g. (37.5 mmoles) of anhydrous potassium carbonate in 20 ml. of N,N-dimethylformamide was heated at 85° C. for 6 hours. It was then cooled and added to 200 ml. of water and 200 ml. of ether. The organic extract was washed twice with 150 ml. portions of water, dried over magnesium sulfate and evaporated to an oil. The oil was purified via column chromatography on 400 g. of silica gel eluted with 2:1 pentane:methylene chloride to yield 4.39 g. (82%) of the desired product as an oil.

PMR: $\delta_{CDCl_3}^{TMS}$ 1.21 (d, J=6 Hz, sidechain methyl), 1.7 (m, sidechain methylenes), 2.60 (m, sidechain benzyl methylene), 4.25 (m, sidechain methine), 5.00 (s, benzyl ether methylene), 6.22 (dd, J=8 and 2 Hz, C-5 ArH), 6.39 (d, J=2 Hz, C-3 ArH) and 7.30 (m, PhH and C-6 ArH).

IR: (CHCl$_3$) 1587 cm$^{-1}$.

MS: 426, 424, (M+), 280, 278 and 91.

The following compounds are similarly prepared from the appropriate mesylate CH$_3$SO$_3$—Z—W.

| (alk$_2$) | W |
|---|---|
| (CH$_2$)$_4$ | 4-FC$_6$H$_4$ |
| (CH$_2$)$_8$ | C$_6$H$_5$ |
| (CH$_2$)$_{10}$ | 4-ClC$_6$H$_4$ |
| CH(CH$_3$)(CH$_2$)$_8$ | C$_6$H$_5$ |
| CH(CH$_3$)CH$_2$ | 4-FC$_6$H$_4$ |
| C(CH$_3$)$_2$(CH$_2$)$_3$ | C$_6$H$_5$ |
| CH$_2$CH(CH$_3$)CH$_2$ | C$_6$H$_5$ |
| CH(CH$_3$)(CH$_2$)$_{10}$ | H |
| C(CH$_3$)$_2$(CH$_2$)$_5$ | H |
| C(CH$_3$)$_2$(CH$_2$)$_7$ | H |
| (CH$_2$)$_{13}$ | H |
| (CH$_2$)$_{13}$ | C$_6$H$_5$ |
| CH(CH$_3$)(CH$_2$)$_6$ | 4-FC$_6$H$_4$ |
| C(CH$_3$)$_2$(CH$_2$)$_{10}$ | 4-FC$_6$H$_4$ |
| (CH$_2$)$_{12}$ | C$_6$H$_5$ |
| CH(C$_2$H$_5$)(CH$_2$)$_3$ | 4-ClC$_6$H$_4$ |
| C(CH$_3$)$_2$(CH$_2$)$_6$ | H |
| (CH$_2$)$_2$C(CH$_3$)$_2$(CH$_2$)$_2$ | H |
| (CH$_2$)$_6$ | C$_6$H$_5$ |
| (CH$_2$)$_{12}$ | H |
| CH(CH$_3$)(CH$_2$)$_3$ | 4-pyridyl |
| (CH$_2$)$_2$ | 4-pyridyl |
| CH(CH$_3$)(CH$_2$)$_3$ | 2-pyridyl |
| (CH$_2$)$_5$ | 3-pyridyl |
| (CH$_2$)$_{10}$ | 2-pyridyl |
| CH(C$_2$H$_5$)(CH$_2$)$_2$ | 4-pyridyl |

PREPARATION I

1-Bromo-2,4-dibenzyloxybenzene

A mixture of 75.0 g. (0.397 mol.) of 4-bromoresorcinol, 95.1 ml. (0.80 mol.) of benzylbromide and 331 g. (2.4 mol.) of anhydrous potassium carbonate in 400 ml. of N,N-dimethylformamide was stirred for 12 hours at 25° C. and for 4 hours at 85° C. The reaction mixture was cooled and added to one liter of ice—200 ml. pentane—100 ml. ether. The organic phase was washed with three 500 ml. portions of water, dried over magnesium sulfate and evaporated to an oil. The oil was rapidly chromatographed on 400 g. of silica gel eluted with 20% ether-pentane to yield 80 g. of oil. The chromatographed oil was crystallized from pentane at 0° C. to yield 45.0 g. (30%) of the title compound, M.P. 37°–38° C.

PMR: $\delta_{CDCl_3}^{TMS}$ 5.0 (s, C-4 benzylether methylene), 5.08 (s, C-2 benzylether methylene), 6.45 (dd, J=8 and 2 Hz, C-5H), 6.63 (d, J-2 Hz, C-3H), 7.2–7.6 (m, PhH and ArH).

IR: (CHCl$_3$) 1605 and 1590 cm$^{-1}$.

MS: m/e 370 (M+), 368 and 91.

Analysis: Anal. Calc'd. for C$_{20}$H$_{17}$BrO$_2$: C, 65.03; H, 4.64; Br, 21.65. Found: C, 64.95; H, 4.55; Br, 21.48.

PREPARATION J 2-(3-Methoxyphenyl)-5-phenylpentane

A solution of 1-bromopropylbenzene (51.7 g.) in ether (234 ml.) is added dropwise over a 2-hour period to a refluxing mixture of magnesium (7.32 g.) in ether (78 ml.). The reaction mixture is refluxed for 30 minutes longer and then a solution of 3-methoxy-acetophenone (41.6 g.) in ether (78 ml.) is added dropwise and the mixture heated to reflux for 1.5 hours. The reaction is quenched by addition of saturated ammonium chloride (234 ml.), the ether layer is separated and the aqueous phase extracted with ether (3×200 ml.). The combined ether extracts are dried over magnesium sulfate and concentrated under vacuum to yield an oil. The oil is hydrogenated in a mixture containing ethanol (300 ml.), concentrated hydrochloric acid (2 ml.) and 5% palladium-on-carbon (5 g.). The catalyst is filtered off and the ethanol removed under vacuum. The residue is distilled under vacuum to give the title product.

PREPARATION K 2-(3-Hydroxyphenyl)-5-phenylpentane

A mixture of 2-(3-methoxyphenyl)-5-phenylpentane (18.4 g.) and pyridine hydrochloride (94 g.) under nitrogen is heated to 190° C. for 2 hours with vigorous stirring. The reaction mixture is cooled, dissolved in 6 N hydrochloric acid (200 ml.) and diluted with water to 600 ml. The aqueous solution is extracted with ethyl acetate (4×100 ml.), the ethyl acetate extracts dried over sodium sulfate and concentrated under vacuum to yield the crude product. The product is purified by silica gel chromatography.

The following compounds are prepared from appropriate reactant by the method of Preparation J and that of the above preparation:

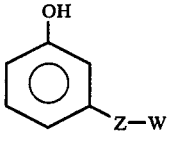

| Z | W |
|---|---|
| CH(CH₃)(CH₂)₂ | C₆H₅ |
| CH(C₂H₅)(CH₂)₂ | 4-ClC₆H₄ |
| CH(C₂H₅)(CH₂)₄ | 4-FC₆H₄ |
| (CH₂)₅ | H |
| (CH₂)₁₁ | H |
| (CH₂)₁₃ | H |
| (CH₂)₄ | C₆H₅ |
| (CH₂)₈ | H |

Bromination of the above compounds according to the procedure of Preparation E affords the corresponding 4-bromo derivatives, e.g. 2-(4-bromo-3-hydroxyphenyl)-5-phenylpentane.

PREPARATION L

Ethyl 3-(3-Benzyloxyphenyl)crotonate (Wittig Reaction)

A mixture of 3-benzyloxyacetophenone (29.4 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of tripheynyl phosphine oxide removed by filtration. The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives the product as an oily residue.

PREPARATION M 3-(3-Benzyloxyphenyl)butyl Tosylate

A solution of ethyl 3-(3-Benzyloxyphenyl)crotonate (17.8 g., 60 mmole) in ether (250 ml.) is added to a mixture of lithium aluminum hydride (3.42 g., 90 mmole) and ether (250 ml.). Aluminum chloride (0.18 g., 1.35 mmole) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the 3-(3-benzyloxyphenyl)butanol as an oil.

Tosyl chloride (11.1 g., 58.1 mmole) is added to a solution of 3-(3-benzyloxyphenyl)-1-butanol (14.5 g., 57 mmole) in pyridine (90 ml.) at −45° C. The reaction mixture is held at −35° C. for 18 hours and is then diluted with cold 2 N hydrochloric acid (1500 ml.) and extracted with ether (5×200 ml.). The combined extracts are washed with saturated sodium chloride solution (4×250 ml.) and then dried (Na₂SO₄). Concentration of the dried extract affords the product as an oil.

PREPARATION N 3-(3-Benxyloxyphenyl)-1-phenoxybutane

A solution of phenol (4.56 g., 48.6 mmole) in dimethylformamide (40 ml.) is added under a nitrogen atmosphere to a suspension of sodium hydride (2.32 g., 48.6 mmole) of 50% previously washed with pentane) in dimethylformamide (70 ml.) at 60° C. The reaction mixture is stirred for one hour at 60°–70° C., after which a solution of 3-(3-benzyloxyphenyl)butyl tosylate (18.9 g., 46 mmole) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and then dried (Na₂SO₄). Removal of the solvent under reduced pressure affords the product as an oil. The oily residue is dissolved in benzene and filtered through silica gel (100 g.). Concentration of the filtrate under reduced pressure gives the product as an oil.

Repetition of Preparation L through N but using the 3-benzyloxy derivatives of benzaldehyde, acetophenone or propiophenone, the appropriate carbethoxy (or carbomethoxy) alklidenetriphenylphosphorane, and the appropriate alcohol or phenol affords the following compounds.

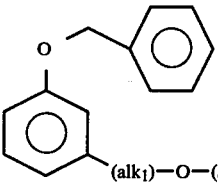

| (alk₁) | n | (alk₂) | W |
|---|---|---|---|
| (CH₂)₃ | 1 | (CH₂)₃ | H |
| (CH₂)₃ | 1 | (CH₂)₅ | H |
| (CH₂)₅ | 1 | (CH₂)₈ | H |
| (CH₂)₆ | 1 | (CH₂)₇ | H |
| (CH₂)₃ | 1 | (CH₂)₇ | H |
| (CH₂)₃ | 1 | (CH₂)₁₀ | H |
| (CH₂)₁₀ | 1 | (CH₂)₂ | H |
| C(CH₃)₂(CH₂)₂ | 1 | (CH₂)₄ | H |
| (CH₂)₄ | 1 | CH₂ | C₆H₅ |
| (CH₂)₆ | 0 | — | C₆H₅ |
| (CH₂)₁₃ | 0 | — | H |
| (CH₂)₆ | 0 | — | H |
| (CH₂)₆ | 1 | CH₂ | 4-ClC₆H₄ |
| (CH₂)₆ | 0 | — | 4-FC₆H₄ |
| CH(CH₃) (CH₂)₂ | 0 | — | C₆H₅ |
| CH(CH₃) (CH₂)₃ | 0 | — | C₆H₅ |
| CH(CH₃) (CH₂)₆ | 0 | — | H |
| (CH₂)₃ | 0 | — | 4-pyridyl |
| (CH₂)₃ | 0 | — | 3-pyridyl |
| (CH₂)₃ | 1 | CH(CH₃) | 2-pyridyl |
| CH(CH₃) (CH₂)₂ | 1 | (CH₂)₄ | 4-pyridyl |
| CH(C₂H₅) (CH₂)₂ | 1 | CH(CH₃) | 2-pyridyl |

-continued

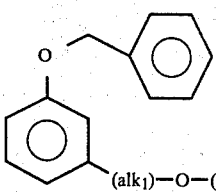

| (alk₁) | n | (alk₂) | W |
|---|---|---|---|
| (CH₂)₄ | 1 | (CH₂)₅ | 4-pyridyl |
| (CH₂)₈ | 1 | (CH₂)₅ | 4-pyridyl |

Debenzylation of the products according to the procedure of Preparation E affords the corresponding 2-bromo-5-[(alk₁)-O-(alk₂)ₙ-W]phenolbenzyl ethers which are brominated via the procedure of Preparation E. Benzylation of the thus produced bromophenols by the procedure of Example F affords the benzyl ether of the 2-bromo-5-[(alk₁)-O-(alk₂)ₘ-W] phenols.

PREPARATION O

4-(3-hydroxyphenyl)-1-(4-pyridyl)pentane

A mixture of 3-(3-methoxyphenyl)butyl triphenylphosphonium bromide (17.5 g., 35.4 mmoles) in dimethylsulfoxide (50 ml.) is added to 4-pyridine-carboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°-5° C. and then concentrated under reduced pressure. The concentrate is diluted with water (200 ml.) and then acidified with 6 N HCl. The aqueous acid solution is extracted with benzene (4×50 ml.). It is then made basic and extracted with benzene (3×50 ml.). Evaporation of the combined extracts after drying (MgSO₄) affords 4-(3-methoxyphenyl)-1-(4-pyridyl)-1-pentene as an oil.

Catalytic hydrogenation of the thus-produced pentene derivative in ethanol at 45 p.s.i. in the presence of Pd/C (1 g. of 10%) and concentrated HCl (1 ml.) affords the title product.

The pentane derivative thus obtained is demethylated by heating a mixture of the compound (25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel using as eluting agents 5% ethanol/benzene (4 liters), 10% ethanol/benzene (1 liter), 13% ethanol/benzene (1 liter) and 16% ethanol/benzene (5 liters). The product is isolated by concentration of appropriate fractions of the eluate.

The 3-(3-methoxyphenyl)butyltriphenylphosphonium bromide is prepared by refluxing a mixture of 1-bromo-3-(3-methoxyphenyl)butane (78.5 mmoles) and triphenyl phosphine (78.5 mmoles) in xylene (60 ml.) for 18 hours. The reaction mixture is then cooled to room temperature and filtered. The filter cake is washed with ether and the product dried in a vacuum desiccator.

Repetition of this procedure but using the appropriate bromo-(3-methoxyphenyl)alkane and the appropriate aldehyde or ketone affords the following compounds.

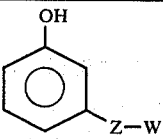

| Z | W |
|---|---|
| (CH₂)₃ | 2-pyridyl |
| (CH₂)₄ | 4-pyridyl |
| CH(CH₃)CH(CH₃)CH₂ | 3-pyridyl |
| CH(CH₃)CH(CH₃)CH₂ | 4-pyridyl |
| CH(C₂H₅)(CH₂)₂ | 4-pyridyl |
| (CH₂)₁₀ | 4-pyridyl |

Bromination of the above compounds according to the method of Preparation E gives the corresponding 2-bromo-5-(Z-W)-phenols.

PREPARATION P

3-Methoxy-α-methylstyrene Oxide

To a solution of dimethylsulfoxonium methylide (69.4 mmoles) in dimethyl sulfoxide (65 ml.) at room temperature is added solid 3-dimethoxyacetophenone (8.33 g., 55.5 mmoles). The reaction mixture is stirred for one hour at 25° C., for one-half hour at 50° C. and is then cooled. The mixture is diluted with water (50 ml.) and added to a mixture of ice water (200 ml.)—ether (250 ml.)—low boiling petroleum ether (25 ml.). The organic extract is washed twice with water (250 ml.), dried (MgSO₄) and evaporated to an oil which is fractionally distilled.

PREPARATION Q

2-(3-Methoxyphenyl)-2-hydroxypropyl-2-phenylethyl Ether

A mixture of dry 2-phenylethanol (30 ml., 250 mmoles) and sodium metal (690 mg., 30 mmoles) is heated at 110° C. for 30 minutes. The resulting 1 M solution of sodium 2-phenylethoxide is cooled to 60° C., 3-methoxy-α-methylstyrene oxide (1.69 g., 10.3 mmoles) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. ~65° C., 0.1 mm.). The residue is purified via column chromatography on silica gel 60 (300 g.) and eluted in 15 ml. fractions with 60% ether-pentane.

PREPARATION R

2-(3-Methoxyphenyl)propyl 2-Phenylethyl Ether

To a 0° C. solution of 2-(3-methoxyphenyl)-2-hydroxypropyl 2-phenylethyl ether (498 mg. 1.74 mmole) in pyridine (2 ml.) is added dropwise phosphorous oxychloride (477 μl., 5.22 mmole). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3×50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases the reaction is filtered through diatomaceous earth and the filtrate evaporated to an oil. The oil is purified via preparative layer chromatography on silica gel plates, eluted twice with 6:1 pentane:ether to yield the title compound.

PREPARATION S

2-(3-Hydroxyphenyl)propyl 2-Phenylethyl Ether

A mixture of 2-(3-methoxyphenyl)propyl 2-phenylethyl ether (176 mg., 0.65 mmole), pyridine (0.4 ml., 4.96 mmole) and dry pyridine hydrochloride (4 g., 34.5 mmole) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield the title product.

The following compounds are prepared from appropriate alkanols by the methods of Procedures Q and R:

| (alk$_2$) | W |
|---|---|
| —(CH$_2$)$_7$— | H |
| —(CH$_2$)$_6$— | C$_6$H$_5$ |
| —(CH$_2$)$_5$— | H |
| —CH(CH$_3$)CH$_2$ | H |
| —CH(CH$_3$)(CH$_2$)$_5$ | H |
| —(CH$_2$)— | 4-FC$_6$H$_4$ |
| —(CH$_2$)$_2$— | 4-pyridyl |
| —(CH$_2$)$_2$— | 4-ClC$_6$H$_4$ |
| —(CH$_2$)$_2$CH(CH$_3$)(CH$_2$)$_3$— | H |
| —CH(CH$_3$)CH$_2$— | H |
| —C(CH$_3$)$_2$CH$_2$— | H |
| —(CH$_2$)$_{10}$— | H |
| —CH$_2$— | C$_6$H$_5$ |

PREPARATION T

3-Methoxy-β-methylstyrene Oxide

To a —78° C. solution of diphenylsulfonium ethylide (1.0 mole) in tetrahydrofuran (one liter) is slowly added 3-methoxybenzaldehyde (1.0 mole). The reaction mixture is stirred at —78° C. for 3 hours and then allowed to warm to room temperature. It is then added to ether-water and the ether phase separated. The ether phase is washed with water, dried (MgSO$_4$) and evaporated. Fractional distillation of the residue gives the title product.

PREPARATION U

3-(3-Hydroxyphenyl)-2-propylbutyl Ether

To a solution of sodium butoxide in butanol (0.5 liters of 1 M) is added 3-methoxy-β-methylstyrene oxide (6.33 mole). The mixture is heated for 18 hours at 70° C. and is then cooled and added to a mixture of ether-water. The ether solution is separated, dried (MgSO$_4$) and evaporated to give the crude product 2-(3-methoxyphenyl)-3-hydroxy-2-propylbutyl ether. It is purified by column chromatography on silica gel with ether-pentane elution.

By means of the procedure of Preparation R the title product is produced.

Similarly, the following are prepared from appropriate alcohols:

| (alk$_2$) | W |
|---|---|
| (CH$_2$)$_2$ | H |
| (CH$_2$)$_7$ | H |
| (CH$_2$)$_3$ | C$_6$H$_5$ |
| (CH$_2$)$_2$ | 4-FC$_6$H$_4$ |
| (CH$_2$)$_2$ | 4-pyridyl |
| CH(CH$_3$) (CH$_2$)$_2$ | H |
| CH(C$_2$H$_5$) (CH$_2$)$_3$ | H |
| CH(CH$_3$)CH$_2$ | C$_6$H$_5$ |
| CH$_2$ | H |
| (CH$_2$)$_2$ | 4-ClC$_6$H$_4$ |

PREPARATION V

1-Bromo-3-(3-methoxyphenyl)butane

A solution of phosphorous tribromide (5.7 ml., 0.06 mole) in ether (30 ml.) is added to a solution of 3-(3-methoxyphenyl)-1-butanol (30.0 g., 0.143 mole) in ether (20 ml.) at —5° C. to —10° C. and the reaction mixture stirred at —5° C. to —10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried (Na$_2$SO$_4$). Removal of the ether and vacuum distillation of the residue affords the title product.

The following compounds are prepared from 3-methoxybenzaldehyde, 3-methoxyacetophenone and 3-methoxypropionphenone and the appropriate carbethoxyalkylidene triphenylphosphorane by the procedures of Preparations L, M and the above procedure.

| Z—Bz |
|---|
| Z |
| (CH$_2$)$_3$ |
| (CH$_2$)$_4$ |
| CH(C$_2$H$_5$)CH$_2$ |
| CH(CH$_3$CH$_2$ |
| CH(CH$_3$) (CH$_2$)$_3$ |

PREPARATION W

3-(3-Benzyloxy)benzyloxypropane

Sodium (0.2 mole) is dissolved in n-propylalchohol (1.0 mole) and the reaction mixture then cooled in an ice-bath. Then 0.2 mole of 3-benzyloxybenzyl chloride is added with constant stirring over a half-hour period. The ice-bath is removed and the temperature gradually raised to reflux. After 4 hours at reflux, the excess alcohol is removed by distillation under reduced pressure. The residue is treated with water to dissolve the salt present and then extracted with diethyl ether. The extract is washed with water, dried (MgSO4) and evaporated to give the title product.

In those instances where the alcohol reactant is not readily available or is a solid at normal temperatures, a modification of this procedure is used. The appropriate alcohol is dissolved in acetone and heated with the halide reactant in the presence of powdered potassium carbonate for 6–8 hours. The reaction mixture is then cooled, water added and the ether recovered as described above.

The following compounds are prepared in like manner from appropriate alcohols:

| (alk2) | W | (alk2) | W |
|---|---|---|---|
| (CH2)2 | H | — | C6H5 |
| (CH2)4 | H | — | 4-pyridyl |
| (CH2)12 | H | CH(CH3) (CH2)2 | C6H5 |
| (CH2) | C6H5 | CH2 | C6H5 |
| CH(CH3)CH2 | H | (CH2)5 | 4-FC6H4 |
| (CH2)2CH(CH3) | C6H5 | CH2CH(C2H5)CH2 | H |

Debenzylation of the products according to the procedure of Preparation E affords the corresponding 2-bromo-5-[(alk1)-O-(alk2)n-W]phenolbenzyl ethers which are brominated via the procedure of Preparation E. Benzylation of the thus produced bromophenols by the procedure of Example F affords the benzyl ether of the 2-bromo-5-[alk1)-O-(alk2)m-W] phenols.

PREPARATION X

6-(3-Butenyl)-3-ethoxy-2-cyclohexen-1-one

A solution of 25 g. (0.178 mole) of 3-ethoxy-2-cyclohexen-1-one in 25 ml. of tetrahydrofuran is added dropwise (30 min.) to a −78° C. solution of 0.196 mole of lithium diisopropylamide (from 27.4 ml., 0.196 mole, of diisopropylamine and 85 ml., 0.187 mole, of 2.2 M n-butyl lithium in hexane) in 125 ml. of tetrahydrofuran. The reaction is stirred 30 minutes longer and then 65 ml. (0.374 mole) of hexamethylphosphoramide is added followed by 38.9 ml. (0.383 mole) of 4-bromo-1-butene. The reaction is then allowed to warm to room temperature, stirred 1.5 hours and quenched by addition of 5 ml. (0.277 mole) of water. Most of the solvent is removed under reduced pressure and the residue diluted with one liter ice water and 500 ml. ether. The ether extract is washed with two 300 ml. portions of water, dried over magnesium sulfate and evaporated. Distillation of the crude oil yields 10.1 g. (29%) of the title product.

B.P.: 83° C. (0.02 torr).

PMR: $\delta_{CDCl_3}^{TMS}$ 1.34 (t, J=7 Hz, methyl), 1.3–2.6 (m), 3.86 (q, J=7 Hz, methylene), 4.75–5.2 and 5.45–6.2 (m, terminal olefin) and 5.26 (s, vinyl H).

Similarly, the following compounds are prepared from appropriate 3-alkoxy-2-cycloalken-1-ones and appropriate iodides, R2'I or bromides R2'Br.

| x | R° | R2' |
|---|---|---|
| 1 | CH3 | CH3 |
| 1 | C2H5 | n-C3H7 |
| 1 | C2H5 | i-C3H7 |
| 1 | i-C4H9 | n-C4H9 |
| 1 | i-C4H9 | i-C4H9 |
| 1 | C2H5 | n-C6H13 |
| 1 | C2H5 | CH2—CH=CH2 |
| 1 | CH3 | (CH2)3CH=CH2 |
| 1 | CH3 | (CH2)4CH=CH2 |
| 1 | C2H5 | CH2CH=CH—CH3 |
| 1 | C2H5 | (CH2)2CH=CH—CH2CH3 |
| 1 | CH3 | CH2C6H5 |
| 1 | CH3 | (CH2)4C6H5 |
| 2 | i-C4H9 | n-C3H7 |
| 2 | i-C4H9 | n-C6H13 |
| 2 | i-C4H9 | CH2—CH=CH2 |
| 2 | C2H5 | (CH2)3CH=CH2 |
| 2 | i-C4H9 | (CH2)3C6H5 |
| 2 | C2H5 | CH2C6H5 |
| 2 | CH3 | (CH2)2CH=CH2 |
| 3 | CH3 | CH3 |
| 3 | CH3 | n-C3H7 |
| 3 | i-C4H9 | n-C5H11 |
| 3 | i-C4H9 | i-C3H7 |
| 3 | i-C4H9 | CH2CH=CH2 |
| 3 | i-C4H9 | (CH2)2CH=CH2 |
| 3 | i-C4H9 | CH2C(CH3)=C(CH3)CH3 |
| 1 | C2H5 | CH2CH=C(CH3)2 |
| 3 | CH3 | (CH2)2C6H5 |

PREPARATION Y

4-(3-Butenyl)-2-cyclohexen-1-one

To a 0° C. slurry of 1.06 g. (26 mmole) of lithium aluminum hydride in 75 ml. of ether was added a solution of 10 g. (51 mmole) of 6-(3-butenyl)-3-ethoxy-2-cyclohexen-1-one in 25 ml. of ether. After stirring one hour the reaction was quenched by addition of 100 ml. of 2 N hydrochloric acid. The quenched mixture was stirred 30 minutes and then extracted with 300 ml. of ether. The ether extract was washed with 250 ml. saturated sodium bicarbonate, dried over magnesium sulfate and evaporated.

Distillation of the crude oil gave 5.98 g. (78%) of the title product.

B.P.: 133°–136° C. (22 torr).

PMR: $\delta_{CDCl_3}^{TMS}$ 1.3–2.7 (m), 4.9–5.4 (m, terminal olefin), 5.5–6.2 (m, terminal olefin), 6.02 (bd, J=10 Hz, C-2 vinyl H) and 6.91 (bd, J=10 Hz, C-3 vinyl H).

By means of this procedure, the compounds tabulated in Preparation X are converted to compounds having the following formula wherein R°, R2' and x are as defined in Preparation X.

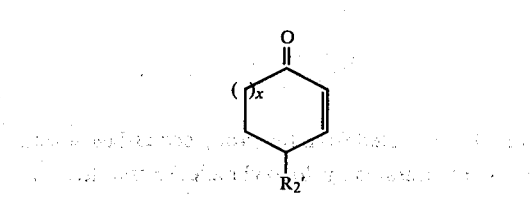

PREPARATION Z

2-Benzyloxy-4-(1,1-dimethylheptyl)benzaldehyde 2-(3-benzyloxy-4-bromophenyl)-2-methyloctane (100 g., 0.257 mole) in tetrahydrofuran (500 ml.) was slowly added to 70–80 mesh magnesium (12.3 g., 0.514 mole) at such a rate that reflux was maintained. Upon completion of addition, the reaction mixture was stirred until it cooled to room temperature. It was then further cooled to 0° C. Dimethylformamide (29.8 ml., 0.385 mole) was added dropwise to the reaction mixture over a 25 minute period (reaction temperature <10° C.). The reaction mixture was then allowed to warm and was stirred for 40 minutes at room temperature. The reaction mixture was quenched by addition to a saturated aqueous solution of cold ammonium chloride (1800 ml.) and the product extracted with ether (one liter). The ether extract was washed twice with saturated sodium chloride (1500 ml.), dried over magnesium sulfate and evaporated to a quantitative yield of the title compound as an oil.

IR: (CHCl$_3$), 1693, 1618 and 1580 cm$^{-1}$.

MS: (m/e) 338 (M+), 309, 253, 247 and 91.

PMR: $\delta_{CDCl_3}^{TMS}$ 0.82 (terminal methyl), 1.30 (s, gem dimethyl), 518 (s, benzylic methylene), 7.0 (m, two ArH), 7.39 (bs, Ph), 7.76 (d, J=8 Hz, ArH) and 10.53 (s, CHO).

By means of this procedure, the 2-benzyloxy-4-(Z-W)bromobenzenes of Preparations F, H, I, N and W are converted to the corresponding benzaldehydes having the formula

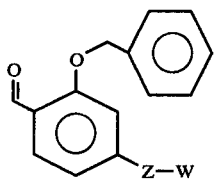

wherein Z and W are as defined in said Preparations.

What is claimed is:

1. A compound selected from the group consisting of those having the formula

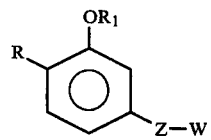

wherein R is selected from the group consisting of saturated and unsaturated cycloalkyl moieties selected from the group consisting of

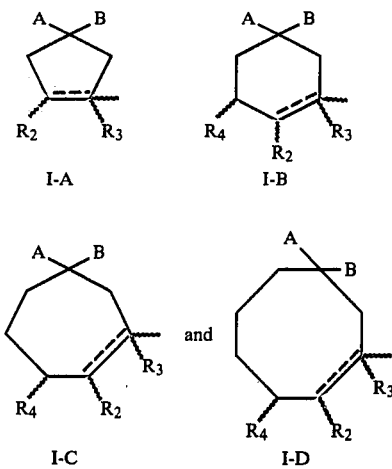

wherein
  A is hydrogen;
  B is hydroxy;
  R$_1$ is selected from the group consisting of hydrogen and benzyl;
  R$_2$ is selected from the group consisting of hydrogen, alkyl having from one to six carbon atoms and alkenyl having from three to six carbon atoms;
  R$_3$ is hydrogen;
  R$_4$ is selected from the group consisting of hydrogen and alkyl having from one to six carbon atoms;
  Z is selected from the group consisting of
    (a) alkylene having from seven to eleven carbon atoms; and
    (b) (alk$_1$)$_m$—O—(alk$_2$)$_n$— wherein each of (alk$_1$) and (alk$_2$) is alkylene having from one to eleven carbon atoms; each of m and n is 0 or 1; with the provisos that the summation of carbon atoms in (alk$_1$) plus (alk$_2$) is not less than seven or greater than eleven; and at least one of m and n is 1 and
  W is hydrogen.

2. A compound according to claim 1, wherein R is a saturated cycloalkyl moiety.

3. A compound according to claim 2 wherein B is hydroxy, R$_1$ is hydrogen and Z is alkylene.

4. A compound according to claim 3 wherein each of R$_2$ and R$_4$ is hydrogen and Z is C(CH$_3$)$_2$(CH$_2$)$_6$.

5. The compound according to claim 4 wherein R is I-B, said compound being 3-[2-hydroxy-4-(1,1-dimethylheptyl)phenyl]cyclohexanol.

6. The compound according to claim 4 wherein R is I-C, said compound being 3-[2-hydroxy-4-(1,1-dimethylheptyl)phenyl]cycloheptanol.

7. A compound according to claim 3 wherein R$_2$ is alkyl, R$_4$ is hydrogen, and Z is C(CH$_3$)$_2$(CH$_2$)$_6$.

8. The compound according to claim 7 wherein R is I-B, R$_2$ is methyl, said compound being 3-[2-hydroxy-4-(1,1-dimethylheptyl)phenyl]-4-methylcyclohexanol.

9. The compound according to claim 7 wherein R is I-B, R$_2$ is n-propyl, said compound being 3-[2-hydroxy-4-(1,1-dimethylheptyl)phenyl]-4-n-propylcyclohexanol.

10. A compound according to claim 3 wherein R is I-B, R$_2$ is alkenyl, R$_4$ is hydrogen and Z is C(CH$_3$)$_2$(CH$_2$)$_6$.

11. The compound according to claim 10 wherein R$_2$ is 2-propenyl, said compound being cis-3-[2-hydroxy-4-(1,1-dimethylheptyl)phenyl]-trans-4-(2-propenyl)cyclohexanol.

12. A compound according to claim 3 wherein R is I-B, R$_4$ is methyl, R$_2$ is hydrogen and Z is C(CH$_3$)$_2$—(CH$_2$)$_7$, said compound being cis-3-[2-hydroxy-4-(1,1-dimethyloctyl)phenyl]-cis-5-methylcyclohexanol.

* * * * *

UNITED STATES PATENT AND TRADEMARK OFFICE
CERTIFICATE OF CORRECTION

PATENT NO. : 4,306,097

DATED : December 15, 1981

INVENTOR(S) : Charles A. Harbert et al.

It is certified that error appears in the above-identified patent and that said Letters Patent are hereby corrected as shown below:

Col. 6, line 36, "0.2", second occurrence, should read -- 0.02 --.

Col. 11, lines 40 and 43, "quaiacol" should read -- guaiacol --.

Col. 23, lines 2 and 46, "$M^{30}$" should read -- $M^+$ --.

Col. 25, lines 30 and 41, "82,30" at each occurrence should read -- 82.30 --.

Col. 25, line 45, delete "b".

Col. 25, line 55, "3[2benzyloxy" should read -- 3-[2-benzyloxy --.

Col. 25, line 56, delete "b".

Col. 28, line 67, "3.0" should read -- 3.70 --.

Col. 29, line 56, "dimthyl" should read -- dimethyl --.

Col. 30, line 48, delete "MS".

Col. 37, line 35, "$ClC_6H_5$" should read -- $ClC_6H_4$ --.

Col. 37, line 43, "$CH(c_2H_5)(CH_2)_2$" should read -- $CH(C_2H_5)(CH_2)_2$ --.

Col. 42, line 34, "$M^{30}$" should read -- $M^+$ --.

Col. 44, line 44, "$(CH_2)_3XH_5$" should read -- $(CH_2)_3C_6H_5$ --.

UNITED STATES PATENT AND TRADEMARK OFFICE
CERTIFICATE OF CORRECTION

PATENT NO. : 4,306,097

DATED : December 15, 1981

INVENTOR(S) : Charles A. Harbert et al.

It is certified that error appears in the above-identified patent and that said Letters Patent are hereby corrected as shown below:

Col. 46, line 48, under headings $R_2$ and Z of the Table, "$(CH_2)_4CH=$" "$OCH_2 \atop CH_2$" should read -- $(CH_2)_4CH=CH_2$   $OCH_2$ --.

Col. 46, line 49, under headings $R_2$ and Z of the Table, "$CH_2CH=CH- \atop CH_3$" "$(CH_2)_3OCH(CH_3)$" should read -- $CH_2CH=CH-CH_3$   $(CH_2)_3OCH(CH_3)$ --.

Col. 48, line 23, "$C(CH_3)_2 2)_6$" should read -- $C(CH_3)_2(CH_2)_6$ --.

Col. 52, line 36, "morpholino" should read -- N-piperidyl --.

Col. 62, line 2, "ArN" should read -- ArH --.

Col. 71, line 66, "0.20" should read -- 5.20 --.

Col. 74, line 51, "356 and 354($M^+$), 340,338" should read -- 328 and 326($M^+$), 313,311 --.

Col. 87, line 33, "518" should read -- 5.18 --.

Signed and Sealed this

Eleventh Day of May 1982

[SEAL]

Attest:

GERALD J. MOSSINGHOFF

Attesting Officer   Commissioner of Patents and Trademarks